US009175256B2

(12) United States Patent
Chen et al.

(10) Patent No.: US 9,175,256 B2
(45) Date of Patent: Nov. 3, 2015

(54) PRODUCTION OF FATTY ACIDS AND FATTY ACID DERIVATIVES BY RECOMBINANT MICROORGANISMS EXPRESSING POLYPEPTIDES HAVING LIPOLYTIC ACTIVITY

(75) Inventors: You Chen, San Diego, CA (US); Thomas E. Wall, Austin, TX (US); Stanley Bower, San Diego, CA (US); Robert Christopher Brown, San Diego, CA (US); Jennifer Coppersmith, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 7 days.

(21) Appl. No.: 13/324,653

(22) Filed: Dec. 13, 2011

(65) Prior Publication Data
US 2012/0184003 A1 Jul. 19, 2012

Related U.S. Application Data

(60) Provisional application No. 61/426,624, filed on Dec. 23, 2010, provisional application No. 61/426,555, filed on Dec. 23, 2010, provisional application No. 61/426,568, filed on Dec. 23, 2010, provisional application No. 61/426,602, filed on Dec. 23, 2010.

(51) Int. Cl.
| C12P 7/64 | (2006.01) |
| C12N 1/20 | (2006.01) |
| C12N 1/00 | (2006.01) |
| C12N 1/12 | (2006.01) |
| C12N 15/00 | (2006.01) |
| C12N 1/38 | (2006.01) |
| C12N 9/20 | (2006.01) |
| C12N 9/80 | (2006.01) |
| C12N 9/00 | (2006.01) |

(52) U.S. Cl.
CPC .. *C12N 1/12* (2013.01); *C12N 1/38* (2013.01); *C12P 7/6409* (2013.01)

(58) Field of Classification Search
None
See application file for complete search history.

(56) References Cited

U.S. PATENT DOCUMENTS

| 5,447,858 A | 9/1995 | Key et al. ............... 435/172.3 |
| 5,639,952 A | 6/1997 | Quail et al. ................. 800/205 |
| 5,661,017 A | 8/1997 | Dunahay et al. ........... 435/172.3 |
| 5,689,044 A | 11/1997 | Ryals et al. ................. 800/205 |
| 5,750,385 A | 5/1998 | Shewmaker et al. ...... 435/172.3 |
| 5,851,796 A | 12/1998 | Schatz ......................... 435/69.1 |
| 5,928,933 A | 7/1999 | Dicosimo et al. ............ 435/280 |
| 5,990,069 A | 11/1999 | Andre et al. ................. 510/281 |
| 6,255,451 B1 | 7/2001 | Koch et al. ................... 528/490 |
| 6,365,398 B1 | 4/2002 | Bornscheuer et al. ........ 435/280 |
| 6,379,945 B1 | 4/2002 | Jepson et al. ................. 435/243 |
| 6,410,828 B1 | 6/2002 | Armstrong et al. ........... 800/287 |
| 6,486,295 B1 | 11/2002 | Gross et al. .................. 528/354 |
| 6,642,035 B2 | 11/2003 | Janda et al. .................. 435/135 |
| 7,135,290 B2 | 11/2006 | Dillon .............................. 435/6 |
| 7,205,373 B2 | 4/2007 | Brandstadt et al. ............. 528/26 |
| 7,294,506 B2 | 11/2007 | Daniell et al. .............. 435/320.1 |
| 7,455,998 B2 | 11/2008 | Brandstadt et al. ........... 435/131 |
| 7,745,696 B2 | 6/2010 | Melis et al. ................... 800/285 |
| 2007/0136892 A1 | 6/2007 | Zank et al. .................... 800/281 |
| 2009/0035842 A1 | 2/2009 | Trimbur et al. .......... 435/254.22 |
| 2009/0061493 A1 | 3/2009 | Trimbur et al. .............. 435/157 |
| 2009/0298143 A1 | 12/2009 | Roessler et al. .............. 435/134 |
| 2010/0150901 A1 | 6/2010 | Meyers et al. ............. 424/130.1 |
| 2010/0151567 A1 | 6/2010 | Franklin et al. ............. 435/320.1 |
| 2010/0251601 A1 | 10/2010 | Hu et al. .......................... 44/313 |
| 2011/0020883 A1 | 1/2011 | Roessler et al. .............. 435/134 |
| 2011/0054027 A1 | 3/2011 | Whitton et al. ............... 514/558 |
| 2011/0250659 A1 | 10/2011 | Roberts et al. ................ 435/134 |

FOREIGN PATENT DOCUMENTS

| WO | WO 96/18729 | 6/1996 | ............. C12N 9/18 |
| WO | WO 00/61740 | 10/2000 | ............. C12N 15/10 |
| WO | WO 00/62601 | 10/2000 | ............. A01H 13/00 |
| WO | WO 03/091413 | 11/2003 | |
| WO | WO 2005/005643 | 1/2005 | ............. C12N 15/82 |
| WO | WO 2007/133558 | 11/2007 | ............. E21B 37/00 |
| WO | WO 2007/136762 | 11/2007 | ............. C12N 1/00 |
| WO | WO 2008/119082 | 10/2008 | ............. C12P 7/64 |
| WO | WO 2008/151149 | 12/2008 | ............. C12N 9/00 |
| WO | WO-2009/085278 A1 | 7/2009 | |
| WO | WO 2009/085278 A1 * | 7/2009 | |
| WO | WO 2009/133351 | 11/2009 | |
| WO | WO 2009/140701 | 11/2009 | |

(Continued)

OTHER PUBLICATIONS

GenBank Accession No. Q39513, Jun. 2009, 2 pages.*
GenBank Accession No. BAA17403, May 2009, 1 page.*
Gardes et al., Standards in Genomic Sciences 3:97-107, Sep. 2010.*
GenBank Accession No. CP001978, Nov. 9, 2010, 1 page.*
GenBank Accession No. ADI78874, Sep. 2010, 1 page.*
Santiago et al., PNAS 105:5809-5814, 2008.*
GenBank Accession No. NP_010343, Dec. 2009, 2 pages.*
Wu et al., DNA Cell Biol. 17:915-920, 1998.*
UniProt Accession No. E4PGJ6, Feb. 2011, 1 page.*
Torres-Gavilán et al., J. Mol. Catal. B: Enzym. 41:136-140, 2006.*
Voet et al., "Biochemistry, Second Edition", John Wiley and Sons, Inc., New York, 1995, pp. 930-931.*
Jackowski et al., J. Biol. Chem. 269:2921-2928, 1994.*
Asada et al., Biochim. Biophys. Acta 1490:269-278.*

(Continued)

*Primary Examiner* — David J Steadman
(74) *Attorney, Agent, or Firm* — Harness, Dickey and Pierce, P.L.C.

(57) ABSTRACT

The invention provides transgenic photosynthetic microorganisms that include non-native genes encoding polypeptides having lipolytic activity for production of free fatty acids and fatty acid derivatives, and methods of producing free fatty acids and fatty acid derivatives using the transgenic microorganisms disclosed herein. The invention also provides transgenic microorganisms that include non-native genes encoding polypeptides having lipolytic activity, and novel genes encoding polypeptides demonstrating lipolytic activity.

24 Claims, No Drawings

(56) References Cited

FOREIGN PATENT DOCUMENTS

| WO | WO 2010/075483 | 1/2010 |
|----|----|----|
| WO | WO 2010/051489 | 5/2010 |
| WO | WO 2010/101665 A1 * | 9/2010 |
| WO | WO 2011/008565 | 1/2011 |
| WO | WO 2011/034863 | 3/2011 |
| WO | WO 2011/059745 | 5/2011 |
| WO | WO-2012/087675 A1 | 6/2012 |
| WO | WO-2012/092033 A1 | 7/2012 |

OTHER PUBLICATIONS

Kaczmarzyk et al., Plant Physiol. 152:1598-1610, 2010.*
Abe, J., et al. (2008), "Expression of exogenous genes under the control of endogenous HSP70 and CAB promoters in the closterium peracerosum-strigosum-littorale complex", *Plant Cell Physiol*, 49(4): 625-632.
Altschul, S., et aL, (1997), "Gapped BLAST and PSI-BLAST: a new generation of protein database search programs", *Nucleic Acids Research*, 25(17): 3389-3402.
Arpigny J., et al., (1999), "Bacterial Lipolytic Enzymes: classification and properties", *Biochem J.*, 343: 177-183.
Bateman, A., et al. (2000), "The pfam protein families database", *Nucleic Acids Research*, 28(1):263-266.
Bateman, A., et al. (2004), "The pfam protein families database", *Nucleic Acids Research*, 32: Database Issue: D138-D141.
Buikema, W., et al. (2000), "Expression of the anabaena hetR gene from a copper-regulated promoter leads to heterocyst differentiation under repressing conditions", *Proc. Natl. Acad. Sciences USA* 98(5): 2729-2734.
Côté, A., et al., (2010), "Expression and characterization of a novel heterologous moderately thermostable lipase derived from metagenomics in streptomyces lividans." *J. Ind. MicrobioL Biotechnol*. 37(9): 883-891.
D'Abusco A., et aL, (2001), "Molecular and biochemical characterization of the recombinant amidase from hyperthermophilic archaeon sulfolobus solfataricus", *Extremophiles*, 5(3): 183-192.
Du Plessis, E., et al., (2010), "Characterization of a novel thermostable esterase from *Thermus scotoductus* SA-01: evidence of a new family of lipolytic esterases", *Current Microbiology*, 60(4): 248-253.
Finn, R., et al. (2006), "Pfam: clans, web tools and services", *Nucleic Acids Research*, 34: Database Issue 34:D247-D251.
Finn, R., et al. (2010), "The pham protein families database", *Nucleic Acids Research*, 38: Database Issue 38:D211-D222.
Genbank submission CAA89087, (2005), Retrieved from the internet: <URL: http://www.ncbi.nlm.nih.gov/protein/CAA89087>.
Genbank submission NP 415027, (2010). Retrieved from the internet: <URL: http://www.ncbi.nlm.nih.gov/protein/16128478?sat=14&satkey=1834702>.
Greenway, D., et al. (1983), "Altered acyltransferase activity in *Escherichia coli* associated with mutations in acyl coenzyme a synthetase", *The Journal of Biological Chemistry*, 258(21): 13034-13042.
Gupta, R., et al., (2003), "Lipase assays for conventional and molecular screening: an overview", *Biotechnol Appl. Biochem*, 37: 63-71.
Hallmann, A., et al. (1997), "Gene replacement by homologous recombination in the multicellular green alga volvox carteri" *Proc. Natl. Acad. Sci USA*, 94:7469-7474.
Hallmann, A., et al. (2006), "Swapped green algal promoters: aphVIII-based gene constructs with chlamydomonas flanking sequences work as dominant selectable markers in volvox and vice versa", *Plant Cell Rep* 25(6): 582-591.
Ham, H., et al., (2010), "The TGL2 gene of *Saccharomyces cerevisiae* encodes an active acylglycerol lipase located in the mitochondria", *The Journal of Biological Chemistry*, 285(5): 3005-3013.
Henikoff, S., et al. (1992), "Amino acid substitution matrices from protein blocks", *Proc. Natl. Acad. Sci USA*, 89:10915-10919.

Hu, Q., et al., (2008), "Microalgal triacylglycerols as feedstocks for biofuel production: perspectives and advances", *The Plant Journal*, 54: 621-639.
Hu, Y., et al., (2010), "Novel lipolytic genes from the microbial metagenomic library of the south china sea marine sediment", *FEMS Microbiol Ecol* 72: 228-237.
Huang, B., et al. (1994), "A small, high-copy-number vector suitable for both in vitro and in vivo gene expression", *Gene* 151: 143-145.
International Search Report for PCT/US11/64657 dated May 17, 2012.
Iwai, M., et al. (2004), "Improved genetic transformation of the thermophilic cyanobacterium, thermosynechoccus elongates BP-1", *Plant Cell Physiol*. 45(2):171-175.
Kaczmarzyk, D., et al. (2010), "Fatty acid activation in cyanobacteria mediated by acyl-acyl carrier protein synthetase enables fatty acid recycling", *Plant Physiology*, 152: 1598-1610.
Karlin, S., et al., (1990), "Methods for assessing the statistical significance of molecular sequence features by using general scoring schemes", *Proc. Natl. Acad. Sci. USA*, 87: 2264-2268.
Kindle, K., et al. (1989), "Stable nuclear transformation of chlamydomonas using the chlamydomonas gene for nitrate reductase", *The Journal of Cell Biology*, 109 (6, Part 1), 2589-2601.
Lee, M., et al. (2006), "Isolation and characterization of a novel lipase from a metagenomic library of tidal flat sediments: evidence for a new family of bacterial lipases", *Applied and Environmental Microbiology*, 72(11):7406-7409.
Li, X., et al. (2007), "Large-scale biodiesel production from microalga *Chlorella protothecoides* through heterotrophic cultivation in bioreactors", *Biotechnology and Bioengineering*, 98: 764-771.
Liu, X., et al. (2009), "Nickel-inducible lysis system in synechocystis sp. PCC 6803", *Proc. Natl. Acad. Sciences USA* 106: 21550-21554.
Méndez-Alvarez, S., et al. (1994), "Transformation of chlorobium limicola by a plasmid that confers the ability to utilize thiosulfate" *Journal of Bacteriology*,176(23):7395-7397.
Metzger, J., et al. (2006), "Lipids as renewable resources: current state of chemical and biotechnological conversion and diversification", *Appl Microbiol Biotechnol*, 71: 13-22.
Ohnuma M., et al. (2008), "Polyethylene glycol (PEG)-mediated transient gene expression in a red alga, cyanidioschyzon merolae 10D", *Plant Cell Physiol*. 49(1):117-120.
Overath, P., et al. (1969), "Fatty acid degradation in *Escherichia coli*", *European Journal of Biochemistry*, 7: 559-574.
Park, S., et al. (2007), "A new esterase showing similarity to putative dienelactone hydrolase from a strict marine bacterium, vibrio sp. GMD509", *Appl Microbiol Biotechnol*, 77(1): 107-115.
Perrone, C., et al. (1998), "The chlamydomonas IDA7 locus encodes a 140 kDa dynein intermediate chain required to assemble the I1 inner arm complex", *Molecular biology of the Cell*, 9:3351-3365.
Quinn, J., et al. (2003), "Copper response element and Crr1-dependent $Ni^{2}$-responsive promoter for induced, reversible gene expression in *Chlamydomonas reinhardtii*" *Eukaryotic Cell*, 2(5): 995-1002.
Ramesh, V., et al. (2004), "A simple method for chloroplast transformation in chlamydomonas reinhardtii" *Methods in Molecular Biology*, 274:301-307.
Ravindran, C., et al. (2006), "Electroporation as a tool to transfer the plasmid pRL489 in Oscillatoria MKU 277" *Journal of Microbiological Methods*, 66:174-176.
Roh, C., et al. (2008), "Isolation of a low-temperature adapted lipolytic enzyme from uncultivated micro-organism" *Journal of Applied Microbiology*, 105: 116-123.
Schneider, S., et al. (1998), "biocatalyst engineering by assembly of fatty acid transport and oxidation activities for in vivo application of cytochrome $P-450_{BM-3}$ monooxygenase" *Applied and Environmental Microbiology*, 64(10): 3784-3790.
Schroda, M., et al. (2000), "The HSP70A promoter as a tool for improved expression of transgenes in Chlamydomonas", *The plant journal* 21(2):121-131.
Sonnhammer, E., et al. (1998), "Pfam: multiple sequence alignments and HMM-profiles of protein domains" *Nucleic Acids Research* 26(1):320-322.

(56) References Cited

OTHER PUBLICATIONS

Steinbrenner, J., et al. (2006), "Transformation of the Green Alga Haematococcus pluvialis with a phytoene Desaturase for accelerated astaxanthin biosynthesis" *Applied and Environmental Microbiology* 72(I2):7477-7484.

Sun, Y., et al. (2006), "Functional complementation of a nitrate reductase defective mutant of a green alga dunaliella viridis by introducing the nitrate reductase gene", *Gene* 377:140-149.

Tan, C., et al. (2005), "Establishment of a micro-particle bombardment transformation system for dunaliella saline", *The Journal of Microbiology*, 43:361-365.

Uniprot submission Q55826-SYNY3 (1996), Retrieved from the internet: <URL: http://www.uniprot.org/uniprot/Q55826.txt?version=47>.

Uniprot submission E0YJE9_9ZZZZ (2010), Retrieved from the internet: <URL: http://www.uniprot.org/uniprot/E0YJE9.txt?version=1>.

Uniprot submission A6F504_9ALTE (2007), Retrieved from the internet: <URL: http://www.uniprot.org/uniprot/A6F504.txt?version=9>.

Uniprot submission Q2T3A2_BURTA (2006), Retrieved from the internet: <URL: http://www.uniprot.org/uniprot/Q2T3A2.txt?version=27>.

Van Heusden, P., et al. (1998), "The *Saccharomyces cerevisiae* TGL2 gene encodes a protein and lipolytic activity and can complement an *Escherichia coli* diacylglycerol kinase disruptant", 14: 225-232.

Xiong, et al. (2008), "High-density fermentation of microalga Chlorella protothecoides in bioreactor for microbio-diesel production", *Biotechnological Products and Process Engineering*, 78:29-36.

Walker, T., et al., (2005), "Characterisation of the *Dunaliella tertiolecta* RbcS genes and their promoter activity in *Chlamydomonas reinhardtii*", *Plant Cell Rep*, 23: 727-735.

Extended European Search Report dated Mar. 26, 2014 issued in EP Application No. 11 85 0617.

Liu, X., et al. (2010) "Production and secretion of fatty acids in genetically engineered cyanobacteria", *PNAS*, pp. 1-6.

Lu, X., (2010) "A perspective: Photosynthetic production of fatty acid-based biofuels in genetically engineered cyanobacteria", *Biotechnology Advances*, 28:742-746.

Michinaka, Y., et al. (2003) "Extracellular secretion of free fatty acids by disruption of a fatty acit Acyl-CoA synthetase gene in *Saccharomyces cerevisiae*", *Journal of Bioscience and Bioengineering*, 95(5):435-440.

Scharnewski, M., et al. (2008) "Mutants of *Saccharomyces cerevisiae* deficient in Acyl-CoA synthetases secrete fatty acids due to interrupted fatty acid recycling", *FEBS Journal*, 247:2765-2778.

UNIPROT Database submission B8Y559 (2009) "Full=Lypolytic enzyme", retrieved from EBI accession No. UNIPROT:B8Y559.

UNIPROT Database submission E4PGJ6 (2011) "Full=Amidase signature enzyme", retrieved from EBI accession No. UNIPROT:E4PGJ6.

\* cited by examiner

PRODUCTION OF FATTY ACIDS AND FATTY ACID DERIVATIVES BY RECOMBINANT MICROORGANISMS EXPRESSING POLYPEPTIDES HAVING LIPOLYTIC ACTIVITY

CROSS-REFERENCE TO RELATED APPLICATIONS

This application claims benefit of priority to (I) U.S. Provisional application 61/426,624 filed Dec. 23, 2010 entitled "Lipase-Mediated Production of Free Fatty Acids by Recombinant Microorganisms", (2) U.S. Provisional application 61/426,555 filed Dec. 23, 2010 entitled "Prokaryotic Acyl-ACP Thioesterases for Producing Fatty Acids in Genetically Engineered Microorganisms", (3) U.S. provisional patent application 61/426,568 filed Dec. 23, 2010 entitled "Genetically Engineered Microorganisms Comprising 4-Hydroxybenzoyl-CoA Thioesterases and Methods of Using the Same for Producing Fatty Acids and Fatty Acid Derivatives", and (4) U.S. provisional patent application 61/426,602 filed Dec. 23, 2010 entitled "Culturing a Microorganism with an Elevated Level of a Carboxylate Counterion Source", each of which is hereby incorporated by reference in its entirety.

REFERENCE TO A SEQUENCE LISTING

This application contains references to amino acid sequences and/or nucleic acid sequences which have been submitted concurrently herewith as the sequence listing text file "2010EM386 (PM0012)_ST25.TXT", file size 98.7 KiloBytes (KB), created on Dec. 12, 2011. The aforementioned sequence listing is hereby incorporated by reference in its entirety pursuant to 37 C.F.R. §1.52(e)(5).

TECHNICAL FIELD

The present invention relates, in some embodiments, to recombinant microorganisms that include at least one non-native gene encoding a polypeptide having lipolytic activity, whose expression results in the production of free fatty acids or fatty acid derivatives, and to methods of producing free fatty acids and/or fatty acid derivatives using the recombinant microorganisms. The invention also relates to novel genes encoding polypeptides having lipolytic activity.

BACKGROUND

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years.

Fossil fuel, also known as mineral fuel, is used synonymously with other hydrocarbon-containing natural resources such as coal, oil and natural gas. The utilization of fossil fuels has enabled large-scale industrial development and largely supplanted water driven mills, as well as the combustion of wood or peat for heat. Fossil fuels are a finite, non-renewable resource.

When generating electricity, energy from the combustion of fossil fuels is often used to power a turbine. Older generations often used steam generated by the burning of the fuel to turn the turbine, but in newer power plants, the gases produced by burning of the fuel turn a gas turbine directly. With global modernization in the 20th and 21st centuries, the thirst for energy from fossil fuels, especially gasoline derived from oil, is one of the causes of major regional and global conflicts.

The burning of fossil fuels by humans is the largest source of emissions of carbon dioxide, which is one of the greenhouse gases that allows radiative forcing and contributes to global warming. In the United States, more than 90% of greenhouse gas emissions come from the combustion of fossil fuels. In addition, other air pollutants, such as nitrogen oxides, sulfur dioxide, volatile organic compounds (VOCs) and heavy metals are produced.

Human activity raises levels of greenhouse gases primarily by releasing carbon dioxide from fossil fuel combustion, but other gases, e.g., methane, are not negligible. The concentrations of several greenhouse gases have increased over time due to human activities, such as burning of fossil fuels and deforestation leading to higher carbon dioxide concentrations. According to the global warming hypothesis, greenhouse gases from industry and agriculture have played a major role in the recently observed global warming.

Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Cost-effective alternatives to current sources of supply could help mitigate the upward pressure on energy and these raw material costs.

Algal fermentation for the production of biodiesel (fatty acid alkyl esters) is described in Li et al. (2007) Biotechnology and Bioengineering 98: 764-771; and in Xiong et al. (2008) Biotechnological Products and Process Engineering 78:29-36. These papers describe the growth of the green alga *Chlorella protothecoides* under heterotrophic conditions, the isolation of lipids from the harvested cells, and the production of biodiesel from the extracted lipids by transesterification using an immobilized lipase from *Candida* sp. 99-125. PCT Publication No. WO2008/151149 discloses microbial strains for the production of various biofuel components, including algal strains genetically engineered for the production of lipid. In some disclosed embodiments, the engineered microorganism includes a lipase gene, in which the expressed lipase acts as a transacylase to convert lipids (triacylglycerols) to biodiesel (fatty acid alkyl esters). The disclosure provides that the expression of the lipase gene can be delayed until after the growth period or can be expressed in an intracellular compartment, where it remains separate from the majority of the microalgal lipid (the lipase substrate) until transesterification, preferably after water has been substantially removed from the cells and/or an excess of alcohol has been added to the cells.

PCT Publication Nos. WO2007/136762 and WO2008/119082 disclose compositions and methods for producing biofuels that include recombinant microorganisms engineered for the fermentative production of fatty acid derivatives, such as, inter alia, fatty alcohols and wax esters. The host strain can include a plasmid that includes one or more fatty acid biosynthesis genes and can further include a lipase gene. PCT Publication No. WO2009/133351 discloses the use of plant cells grown in suspension tissue culture for the production of oil that can be used to make biodiesel. In some embodiments a lipase is added to the culture to reduce the glyceration level of the fatty acids produced by the cells.

SUMMARY OF THE INVENTION

The invention provides a recombinant microorganism that includes a nucleic acid molecule that comprises a sequence encoding a polypeptide for producing and/or mediating production of a fatty acid, e.g., a polypeptide having lipolytic activity, operably linked to a heterologous promoter, in which the microorganism thus produces a free fatty acid and/or a fatty acid derivative. In some embodiments, the nucleic acid molecule encoding a lipase or other polypeptide that promotes or participates in the production of a fatty acid or fatty acid derivative can comprise an endogenous gene, in which the heterologous promoter can be introduced into the cell and targeted to a locus of the genome for regulating the lipase or other gene encoding a polypeptide having lipolytic activity. Additionally or alternately, the nucleic acid molecule encoding polypeptide having lipolytic activity can comprise an exogenous gene (e.g., either heterologous or homologous with respect to the host microorganism), in which the exogenous gene can be operably linked to a heterologous promoter when introduced into the microorganism. Still further additionally or alternately, the recombinant microorganisms disclosed herein can include one or more of the following: a non-native nucleic acid molecule that encodes a lipase that is a member of a pfam belonging to the AB Hydrolase pfam clan (CL0028); an exogenous nucleic acid molecule that encodes a lipase that includes a LipA domain identified as conserved protein domain COG1075, or is included in the protein family Pfam PF01674 (Lipase 2); a non-native nucleic acid molecule that encodes a lipase that includes a Lipase 3 domain identified as conserved protein domain COG3675, or is included in the protein family Pfam PF01764 (Lipase 3); a non-native nucleic acid molecule that encodes a lipase that is included in the protein family Pfam PF07819 (PGAP1); or a non-native nucleic acid molecule that encodes a polypeptide that is included in any of the protein families Pfam PF03583, Pfam PF00151 (Lipase), Pfam PF00561 (Ab hydrolase 1), Pfam PF02230 (Ab hydrolase 2), Pfam PF07859 (Ab hydrolase 3), Pfam PF08386 (Ab hydrolase 4), Pfam PF12695 (Ab hydrolase 5), Pfam PF12697 (Ab hydrolase 6), Pfam PF12715 (Ab hydrolase 7), Pfam PF04083 (Abhydro lipase), or Pfam PF01425 (Amidase). Independently or in combination with other embodiments, the exogenous nucleic acid molecule can encode a polypeptide with lipolytic activity comprising an amino acid sequence having at least about 50%, 55%, 60%, 65%, 70%, 75%, 80%, 85%, 90%, 95%, 96%, 97%, 98%, 99%, or about 100% sequence identity to SEQ ID NO:2, SEQ ID NO:4, SEQ ID NO:6; SEQ ID NO:38, SEQ ID NO:40, and/or SEQ ID NO:47; and/or that is codon-optimized for expression in the recombinant microorganism. The nucleic acid sequence that encodes a polypeptide having lipolytic activity can be under the control of a heterologous promoter which can be a constitutive promoter, or can be under the control of an inducible promoter, such as an isopropyl 0-D-1-thiogalactopyranoside (IPTG)-inducible promoter.

The genetically engineered microorganism that includes a non-native gene encoding a polypeptide having lipolytic activity can be any microorganism, such as, for example, a *eubacterium*, archaebacterium, fungus, yeast, heterokont, *cyanobacterium*, or alga. In some embodiments, the recombinant microorganism is a photosynthetic microorganism, such as a microalga or a *cyanobacterium*. Microalgae can include, for example, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox* species. Cyanobacteria can include, for example, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus* species.

In preferred embodiments, a polypeptide having lipolytic activity, such as, for example, a lipase or amidase, can be active within the cells of the microorganism, e.g., during at least a portion of the growth period and/or prior to cell harvesting and/or disruption. Optionally but preferably, at least a portion of the free fatty acid or fatty acid derivative(s) produced by the microorganism can be released into the culture medium by the microorganism. In some embodiments, the recombinant microorganism that includes a recombinant lipase gene may not accumulate triacylglycerols. For example, in, the host microorganism can be a species of microorganism that does not accumulate triacylglycerol molecules when the microorganism does not include any exogenous genes.

Additionally or alternately, the microorganism that includes a non-native gene encoding a polypeptide demonstrating lipolytic activity can comprise at least one endogenous gene whose expression is attenuated and/or disrupted. Some embodiments of the attenuated and/or disrupted endogenous gene can include, but are not necessarily limited to, a gene encoding an acyl-CoA synthetase, acyl-ACP synthetase, acyl-CoA dehydrogenase, acyltransferase, glycerol-3-phosphate dehydrogenase, acetaldehyde-CoA dehydrogenase, pyruvate dehydrogenase, acetate kinase, or the like, or a combination thereof.

Additionally or alternately, a recombinant microorganism that includes a non-native nucleic acid molecule encoding a polypeptide having lipolytic activity can further comprise at least one non-native gene that encodes a polypeptide that participates in the production of fatty acids. For example, the host microorganism can include one or more exogenous genes, and/or one or more engineered endogenous genes, encoding one or more of an acyl beta-ketoacyl synthetase, an acetyl-CoA carboxylase, a malonyl-CoA:ACP transacylase, an acyl-ACP synthetase, or an acyl carrier protein. Additionally or alternately, the recombinant microorganism can comprise at least one non-native gene that encodes a thioesterase, such as, for example, an acyl-ACP thioesterase, an acyl-CoA thioesterase, or a 4-hydroxybenzoyl thioesterase.

Further, a recombinant microorganism that includes a gene encoding a polypeptide having lipolytic activity operably linked to a heterologous promoter can additionally or alternatively include one or more additional non-native genes for the production of fatty acid derivatives, such as fatty alcohols, wax esters, alkanes, or alkenes. For example, a recombinant microorganism can include, in addition to a non-native gene encoding a polypeptide having lipolytic activity, one or more non-native nucleic acid molecules encoding one or more of an acyl-CoA synthetase, an acyl-CoA reductase, an acyl-ACP reductase, a carboxylic acid reductase, a fatty aldehyde reductase, a fatty aldehyde decarbonylase, a fatty acid decarboxylase, a wax synthase, and an acyltransferase.

The invention can also include a method of producing a free fatty acid or a fatty acid derivative comprising culturing a recombinant microorganism as described herein under conditions that allow expression of the non-nonative gene that encodes a polypeptide having lipolytic activity to produce at least one free fatty acid or derivative thereof. The method optionally can further include isolating at least one fatty acid or fatty acid derivative. Isolation may be from the microorganism and/or from the culture medium. The recombinant microorganism in some examples can express a non-native gene encoding a polypeptide having lipolytic activity, such as a lipase or amidase, to produce at least one free fatty acid, and at least a portion of the at least one free fatty acid that is produced can be released from the microorganism into the culture medium, where release of fatty acids is not by lysis of the cells of the microorganism. Alternatively or in addition, in some methods fatty acids and/or fatty acid derivatives can be isolated after disruption of the cells. In some methods, expression of the gene encoding the lipolytic polypeptide encoded by the non-native nucleic acid molecule can be induced. In some examples, the microorganism can be a photosynthetic microorganism and can be cultured phototrophically.

Additionally or alternately, in any of the methods herein, the amount of the fatty acid or fatty acid derivative(s) produced can be at least about 5 mg per liter of culture. Further, additionally or alternately, the level of at least one of a C12-, C14-, C16-, or C18 free fatty acid or a C11-C36 fatty acid derivative can be increased in the culture with respect to a culture of a microorganism of the same strain that does not include a nucleic acid molecule encoding a polypeptide having lipolytic activity operably linked to a heterologous promoter.

The invention can further include a method of producing a free fatty acid or fatty acid derivative, comprising culturing a recombinant microorganism that has attenuated expression of a gene encoding an acyl-ACP synthetase or an acyl-CoA synthetase and comprises at least one gene encoding a polypeptide having lipolytic activity, such as a lipase or amidase, operably linked to a heterologous promoter, wherein the microorganism produces at least one free fatty acid or at least one fatty acid derivative. For example, a recombinant microorganism having an attenuated acyl-ACP synthetase gene or acyl-CoA synthetase gene and a non-native gene encoding a polypeptide having lipolytic activity can produce at least one free fatty acid, where at least a portion of the at least one free fatty acid that is produced can be released from the microorganism into the culture medium, where release of free fatty acids does not include lysis of the cells of the microorganism. The microorganism can include at least one gene, such as a lipase gene or amidase gene, which gene is operably linked to a heterologous promoter such that expression of the recombinant gene by the microorganism advantageously produces at least one free fatty acid or fatty acid derivative, and further, for example, the microorganism can have a disrupted acyl-ACP synthetase gene. Further additionally or alternately, the gene encoding a polypeptide having lipolytic activity, which can be a lipase gene or some other gene, such as, for example, an amidase gene, can be operably linked to an inducible promoter. In some embodiments, the recombinant lipase gene or other gene encoding a polypeptide having lipolytic activity can be an endogenous gene, which can be operably linked to a heterologous promoter, such as a heterologous promoter introduced into the microorganism for induced or constitutive expression of the endogenous gene, resulting in production of a free fatty acid or fatty acid derivative. Alternately, the recombinant lipase gene or other gene encoding a polypeptide having lipolytic activity can be an exogenous gene, which can be operably linked to a heterologous promoter, such that the gene operably linked to a heterologous promoter is introduced into the microorganism for induced or constitutive expression of the gene, resulting in production of a free fatty acid or fatty acid derivative.

In aspects of the invention in which the recombinant microorganism exhibits both (a) an attenuated acyl-CoA synthetase expression or attenuated acyl-ACP synthetase expression and b) expression of a recombinant gene encoding a polypeptide having lipolytic activity, such as a lipase gene or amidase gene operably linked to a heterologous promoter, such that the expression of the gene results in the production (and optionally but preferably release) of at least one free fatty acid, at least 80% of the free fatty acid(s) produced (e.g., at least 85%, at least 90%, at least 95%, at least 96%, at least 97%, or at least 98%) can have an acyl chain length of at least 16 carbons and optionally also of no greater than 24 carbons, for example, can have an acyl chain length of 16 to 18 carbons. Alternatively or in addition, the recombinant microorganism that exhibits both (a) an attenuated acyl-CoA synthetase expression or attenuated acyl-ACP synthetase expression and b) expression of a recombinant gene encoding a polypeptide having lipolytic activity, such that the expression of the gene results in the production (and optionally but preferably release) of at least one fatty acid derivative, at least 80% of the fatty acid derivative(s) produced (e.g., at least 85%, at least 90%, at least 95%, at least 95%, at least 96%, at least 97%, or at least 98%) can have at least 15 carbons and optionally no greater than 48 carbons, for example, can be alkanes, alkenes, or fatty alcohols having from 15-18 carbons, or may, for example, be wax esters having from 32-36 carbons.

Additionally or alternately, in various methods the combination of the attenuation of the acyl-ACP synthetase gene and/or acyl-CoA synthetase gene and the expression of a gene encoding a polypeptide having lipolytic activity can produce a yield in free fatty acid or fatty acid derivative production by the recombinant microorganism that is increased by at least 50% (e.g., by at least 75%, by at least 90%, by at least 100%, by at least 110%, by at least 120%, or by at least 125%) over a production of an organism comprising and expressing only the gene encoding the polypeptide having lipolytic activity.

Also provided herein are novel genes encoding polypeptides having lipolytic activity, where the novel genes encode polypeptides comprising amino acid sequences having at least 50%, at least 55%, at least 60%, at least 65%, at least 70%, at least 75%, at least 80%, at least 85%, at least 90%, at least 95%, at least 97%, at least 99% or about 100% identity to SEQ ID NO:38, SEQ ID NO:40, or SEQ ID NO:47. A nucleic acid molecule that comprises a nucleic acid sequence having at least 55% identity to SEQ ID NO:38, SEQ ID NO:40, or SEQ ID NO:47 can be included in a vector, such as an expression vector, shuttle vector, or integration vector. Nucleic acid sequences having encoding a polypeptide comprising amino acid sequences having at least 50%, at least 55% identity to SEQ ID NO:38, SEQ ID NO:40, or SEQ ID NO:47 can be operably linked to a heterologous promoter, which can be for example, a constitutive or regulatable promoter, for example, an inducible promoter. In some examples, the novel genes encode polypeptides that are members of the pfams belonging to the AB Hydrolase clan, CL0028, for example, members of Pfam PF07859 (AB hydrolase 3) or PF12695 (AB hydrolase 5). In other examples, the novel genes encode polypeptides identified by sequence homology and/or protein family (Pfam) as amidases, for example, the polypeptides can be members of Pfam PF01425 (Amidase family). In some examples, expression in a microorganism of a gene as disclosed herein that encodes a polypeptide having lipolytic activity can result in production of a fatty acid or fatty acid derivative, for example production of at least twice as much of a fatty acid or fatty acid derivative as is produced by a microorganism identical in all respects but not expressing the gene encoding the polypeptide having lipolytic activity.

The invention further provides microorganisms that comprise non-native nucleic acid molecules encoding polypeptides comprising amino acid sequences having at least 50%, at least 55%, at least 60%, at least 65%, at least 70%, at least 75%, at least 80%, at least 85%, at least 90%, at least 95%, at least 97%, at least 99% or about 100% identity to SEQ ID NO:38, SEQ ID NO:40, or SEQ ID NO:47. The transgenic microorganisms can be used to produce a free fatty acid or fatty acid derivative, or can be used for production of the encoded polypeptides having lipolytic activity that can be isolated for use in enzymatic processes and products.

DETAILED DESCRIPTION

As described herein, in some embodiments of the present invention, the present invention provides a recombinant microorganism comprising a non-native gene encoding a polypeptide having lipolytic activity for production of free fatty acids or fatty acid derivatives. The genes, microorganisms, and methods provided herein can be used to provide renewable fuels or chemicals.

Microorganisms

The genetically engineered microorganism that includes a non-native gene gene encoding a polypeptide having lipolytic activity can be any microorganism, including without limitation, a *eubacterium*, archaebacterium, fungus, yeast, heterokont, *cyanobacterium*, alga, or the like. According to some embodiments of the present invention, the host microorganism is a photosynthetic microorganism. Photosynthetic microorganisms useful as host organisms can include, but are not limited to, any photosynthetic microorganisms that are able to convert inorganic carbon into a substrate that can, in turn, be converted to fatty acids and/or fatty acid derivatives. These photosynthetic microorganisms can include prokaryotes as well as eukaryotic organisms, such as various algae, including microalgae and diatoms.

In some embodiments, microorganisms can include eukaryotic algae and cyanobacteria (blue-green algae). Representative eukaryotic algae can include, but are not limited to, green algae (chlorophytes), yellow-green algae (xanthophytes), red algae (rhodophytes), diatoms (bacillariophytes), eustigmatophytes, prasinophytes, glaucophytes, chlorarachniophytes, euglenophytes, chromophytes and dinoflagellates. The microorganisms according to some embodiments of the present invention can include, but are not limited to, the following genera of microalgae: *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox.*

The host microorganism can be of a species that accumulates triglycerides, for example, a species that produces at least 10%, at least 15%, or at least 20% of its dry weight as triglycerides under nutrient starvation or high salt concentration, or produces at least 5%, at least 10%, at least 20%, at least 30%, at least 40%, or at least 50% of its lipids as triglycerides under nutrient replete, nutrient limited, or high salt conditions. Alternatively, a microorganism that comprises a non-native gene encoding a polypeptide having lipolytic activity can in some examples be a microorganism that does not accumulate triglycerides. For example, the microorganism can be a genetically engineered microorganism that does not substantially accumulate triglycerides, for example, does not accumulate more than 1%, more than 2%, or more than 5% of its dry weight as triglycerides. Additionally or alternatively, the microorganism can be a species that does not, in the absence of genetic engineering, substantially accumulate triacylglycerides. For example, the microorganism can be a species of microorganism that does not substantially accumulate triglycerides in the presence or absence of a particular nutrient or media component, for example, the host microorganism can be a species that contains no greater than 10%, no greater than 5%, no greater than 2%, or no greater than 1% triglycerides as a percentage of total cellular lipid, regardless of the culture conditions. For example, most prokaryotic microorganisms do not accumulate triglycerides, including cyanobacterial species (Hu et al. (2008) *The Plant Journal* 54: 621-639).

The microorganisms according to some embodiments of the present invention can include, but not limited to, the following genera of cyanobacteria: *Agmenellum, Anabaena, Anabaenopsis, Anacystis, Aphanizomenon, Arthrospira, Asterocapsa, Borzia, Calothrix, Chamaesiphon, Chloroglocopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.* For example, the recombinant photosynthetic microorganism can be a *Synechococcus, Synechocystis,* or *Thermosynechococcus* species. Alternatively, the recombinant photosynthetic microorganism can be a *Cyanobium, Cyanothece,* or *Cyanobacterium* species, or further alternatively, the recombinant photosynthetic microorganism can be a *Gloeobacter, Lyngbya* or *Leptolyngba* species. A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced.

A recombinant microorganism that includes a recombinant gene encoding a a polypeptide having lipolytic activity, such as, for example, a recombinant lipase gene or amidase gene, can produce at least one free fatty acid, such as one or more of a C6, C8, C10, C12, C14, C16, C18, C20, C22, or C24 free fatty acid or one or more fatty acid derivatives, such as one or more fatty alcohols, alkanes, alkenes, or wax esters having, e.g., from 6 to 48 carbons. The recombinant microorganism as provided herein produces, in preferred embodiments, more of at least one free fatty acid or fatty acid derivative than the same microorganism that is not genetically engineered. In some embodiments, the microorganism can produce at least one free fatty acid or fatty acid derivative during the growth of the culture, or can produce at least one free fatty acid or fatty acid derivative in the absence of disruption or lysis of the cells.

Polypeptides Having Lipolytic Activity

Lipids are a class of molecules that are typically soluble in nonpolar solvents (such as ether and chloroform) and are relatively or completely insoluble in water. Lipid molecules have these properties, because they consist largely of hydrocarbon tails which are hydrophobic in nature. Examples of lipids include fatty acids (saturated and unsaturated); glycerides or glycerolipids (such as monoglycerides (monoacylglycerides), diglycerides (diacylglycerides), triglycerides (triacylglycerides) or neutral fats, phospholipids, phosphoglycerides, glycolipids, or glycerophospholipids, or the like, or combinations thereof); nonglycerides (such as sphingolipids, sterol lipids including cholesterol and steroid hormones, prenol lipids including terpenoids, fatty alcohols, waxes, polyketides, or the like, or combinations thereof); and complex lipid derivatives (such as sugar-linked lipids, or glycolipids, protein-linked lipids, or the like, or a combination thereof). Fats are a subgroup of lipids and can include triacylglycerides.

Lipases are enzymes that catalyze the hydrolysis of ester bonds in glycerolipids, including, but not limited to, mono-, di-, and tri-acyl glycerols, as well as combinations thereof, to release free fatty acids and alcohols. Ubiquitously present in plants, animals, and microorganisms, lipases have been widely employed in food, chemical, and pharmaceutical industries for various applications.

Polypeptides having lipolytic activity are polypeptides exhibiting a capability for hydrolyzing an ester of a carboxylic acid, such as, for example, of a triglyceride, a phospholipid, or a glycolipid, to release a carboxylic acid (for example, to release a fatty acid). Polypeptides having lipolytic activity include lipases, phospholipases, esterases, and cutinases. As disclosed herein, polypeptides characterized as amidases (also called acylamide amidohydrolases) can also have lipolytic activity, where the expression by a microorganism of a polypeptide identified by sequence homology as an amidase or by membership in an amidase protein family ("Pfam"), e.g., the Amidase pfam PF01425 can result in the production of free fatty acids by the microorganism. Thus, in the context of the present invention, polypeptides having lipolytic activity can include amidases.

Assays for lipolytic activity include those provided in the Examples herein that include expression of genes encoding putative lipolytic enzymes in *E. coli* or other microbial hosts in a plate clearing assay (see also, du Plessis et al. (2010) *Curr. Microbiol.* 60: 248-253; Roh and Villatte (2008) *J. Appl. Microbiol.* 105: 116-123), as well as assays described by Gupta et al, *Biotechnol. Appl. Biochem.* (2003) 37:63-71 and U.S. Pat. No. 5,990,069 (International Publication WO 96/18729A1), which are expressly incorporated by reference herein.

The present invention describes recombinant microorganisms transformed with recombinant or heterologous genes encoding polypeptides having lipolytic activity that are capable of producing free fatty acids from membrane lipids or storage lipids, e.g., phospholipids, phosphoglycerides, glycolipids, triacylglycerol, diacylglycerol, monoacylglycerol, or the like, or combinations thereof.

The term "gene" is used broadly to refer to any segment of nucleic acid (typically DNA, but optionally RNA) associated with expression of a given RNA or protein. Thus, genes include sequences encoding expressed RNA (which can include polypeptide coding sequences) and, often, the regulatory sequences required for their expression. Genes can be obtained from a variety of sources, including cloning from a source of interest or synthesizing from known or predicted sequence information and may include sequences designed to have desired parameters.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. (A descendent of a cell that was transformed with a nucleic acid molecule is also referred to as "transformed" if it has inherited the exogenous nucleic acid molecule). The exogenous gene may be from a different species (and so "heterologous"), or from the same species (and so "homologous"), relative to the cell being transformed. An "endogenous" nucleic acid molecule, gene, or protein is the organism's own nucleic acid molecule, gene, or protein as it occurs in, or is naturally produced by, the organism.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of an exogenous or recombinant nucleic acid sequence into the organism, and includes organisms having gene knockouts, targeted mutations and gene replacement, promoter replacement, deletion, or insertion, as well as organisms having exogenous genes that have been introduced into the organism. An exogenous or recombinant nucleic acid molecule can be integrated into the recombinant/genetically engineered organism's genome or in other instances may not be integrated into the recombinant/genetically engineered organism's genome.

The term "recombinant protein" as used herein refers to a protein produced by genetic engineering.

An "expression cassette", as used herein, refers to a gene encoding a protein or functional RNA (e.g., a tRNA, a microRNAs, a ribosomal RNA, etc.) operably linked to expression control sequences, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

When referring to a gene regulatory sequence or to an auxiliary nucleic acid sequence used for maintaining or manipulating a gene sequence (e.g., a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter", even though the promoter may be derived from the same species (or, in some cases, the same organism) as the gene to which it is linked.

The present invention relates to recombinant microorganisms including at least one recombinant gene encoding a polypeptide that operates to liberate fatty acids from one or more lipids.

A gene encoding a polypeptide having lipolytic activity can be a gene encoding a lipase, where a lipase gene can be a gene encoding any lipase, e.g., that liberates a fatty acid from a glycerolipid (including a monoglyceride, a diglyceride, a triglyceride, a phospholipid, a glycolipid, a galactolipid, etc.). For example, a lipase gene can encode a polypeptide having lipase activity that recruits to a pfam that is a member of the Pfam AB Hydrolase clan, CL0028, such as but not limited to, a lipase that is a member of Pfam PF01674, Pfam PF01764, Pfam PF07819, Pfam PF03583, Pfam PF00151, Pfam PF12695, or Pfam PF07859. For example, a recombinant lipase gene of a microorganism as provided herein can encode a protein having an e-value parameter of 0.01 or less, and/or having a bit score higher than the gathering cutoff when queried using the Pfam Profile HMM search software (e.g., HMMER3 or updated version) for any of Pfam PF01674 (Lipase 2, having a gathering cutoff of 20.3), Pfam PF01764 (Lipase 3, having a gathering cutoff of 20.6), Pfam PF07819 (PGAP-1 like protein, having a gathering cutoff of 20.5), Pfam PF03583 (secretory lipase, having a gathering cutoff of 20.0), Pfam PF00151 (lipase, having a gathering cutoff of 20.1), Pfam PF12695 (Ab hydrolase 3, having a gathering cutoff of 27.0), Pfam PF00561 (Ab hydrolase 1, having a gathering cutoff of 22.8); Pfam PF02230 (Ab hydrolase 2, having a gathering cutoff of 20.5); Pfam PF07859 (Ab hydrolase 3, having a gathering cutoff of 20.7); Pfam PF08386 (Ab hydrolase 4, having a gathering cutoff of 21.0); Pfam PF12697 (Ab hydrolase 6, having a gathering cutoff of 24.8); Pfam PF12715 (Ab hydrolase 7, having a gathering cutoff of 20.7). Further, Pfam PF04083 (Abhydro lipase, having a gathering cutoff of 20.2); or an amidase having lipolytic activity, such as, for example, an amidase that is a member of protein family Pfam PF01425 (Amidase, having a gathering cutoff of 20.1).

Additionally or alternately, a lipase gene that can be used in the present invention can include, but is not limited to, the following nucleotide sequences for sll1969 (SEQ ID NO:1; Lipase from *Synechocystis*; Genbank Accession Number BAA17403; Gene ID Number 1652481), sll0482 (SEQ ID NO:3; Lipase from *Synechocystis*; Genbank Accession Number BAA10581; Gene ID Number 1001744) and TGL2 (SEQ ID NO:5; Lipase from *Saccharomyces cereviseae*; Genbank Accession Number NM_001180366; Gene ID Number 296143412), or a gene including a nucleic acid sequence having at least about 50%, at least about 55%, at least about 60%, at least about 65%, at least about 70%, at least about 75%, at least about 80%, at least about 85%, at least about 90%, or at least about 95%, identity to SEQ ID NO:1, SEQ ID NO:3, or SEQ ID NO:5. Further, the lipase gene can comprise nucleotide sequences having at least about 50%, for example, at least about 55%, at least about 60%, at least about 65%, at least about 70%, at least about 75%, at least about 80%, at least about 85%, at least about 90%, at least about 95%, or about 100% identity to SEQ ID NO:37 or SEQ ID NO:46.

Additionally, as demonstrated herein, a gene encoding a polypeptide having lipolytic activity can be a gene encoding an amidase, such as, for example, a polypeptide that is a member of the Amidase Pfam PF 01425. For example, a recombinant lipase gene of a microorganism as provided herein can encode a protein having an e-value parameter of 0.01 or less, and/or having a bit score higher than the gathering cutoff of 20.1 for Pfam PF01425 when queried using the Pfam Profile HMM. Further, the gene encoding a polypeptide having lipolytic activity can be a gene having at least about 50%, at least about 55%, at least about 60%, at least about 65%, at least about 70%, at least about 75%, at least about 80%, at least about 85%, at least about 50%, at least about 55%, at least about 60%, at least about 65%, at least about 90%, at least about 95%, at least about 97%, at least about 99%, or about 100% sequence identity to SEQ ID NO:39.

"Pfam" is a large collection of protein domains and protein families maintained by the Pfam Consortium and available at several sponsored world wide web sites, including: pfam.sanger.ac.uk/ (Welcome Trust, Sanger Institute); pfam.sbc.su.se/(Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr/. The latest release of Pfam is Pfam 25.0 (April 2011, including 12273 families) based on the UniProt protein database release 2010_05. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. (Unless otherwise specified, matches or a queried protein to a Pfam are Pfam-A matches.) All identified sequences belonging to the family are then used to automatically generate a full alignment for the family (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database, for example, using any of the above-reference websites, protein sequences can be queried against the HMMs using HMMER homology search software (e.g., HMMER3 or a further updated version, hmmer.janelia.org/). Significant matches that identify a queried protein as being in a pfam family (or as having a particular pfam domain) are those in which the bit score is greater than or equal to the gathering threshold for the Pfam domain. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

Sll1969 contains a full-length "LipA" conserved domain (COG1075 in the Conserved Domain Database (CDD; available on the world wide web at ncbi.nlm.nih.gov/cdd); 7e-34) and is observed in most cyanobacteria and other bacteria, mainly Gram+ species. Sll1969 (Accession number EDV08240.1) is a member of the lipase-2 (lipase, class 2) superfamily and is classified in Pfam PF01674, a family of sequences related to the extracellular triacylglycerol lipase from *B. subtilis* 168 (a searchable database of protein families related by sequence is available at pfam.sanger.ac.uk/, incorporated by reference herein). Additionally or alternately to sll1969, a host microorganism as provided herein can include an exogenous gene encoding a protein related to Sll1969 having a LipA domain (CDD COG1075) and/or a protein showing a match with Pfam PF01674, having a an e-value parameter of 0.01 or less, or having a bit score higher than 20.3, when queried using the Pfam Profile HMM (for example, using HMMer3). The recombinant gene encoding a lipase can be, for example, an exogenous gene, or can be an endogenous gene operably linked to a heterologous promoter. A microorganism can additionally or alternately include an exogenous or recombinant nucleic acid molecule encoding a protein having at least 50%, at least 55%, at least 60%, at least 65%, at least 70%, 75%, 80%, or 85% identity to the sequence of sll1969 (SEQ ID NO:2), including proteins having 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:2, in which the host microorganism produces at least one free fatty acid in a greater amount that the same microorganism that does not include the exogenous or recombinant lipase gene.

Examples of genes, including those of the lipase 2 superfamily, that may be used (e.g., as exogenous genes) to transform a microorganism disclosed herein can include, without limitation, genes coding *Nostoc punctiforme* lipase 2 (Genbank protein accession number YP_001864549.1), *Nodularia spumigena* protein (Genbank protein accession number ZP_01632206.1), *Cyanothece* sp lipase 2 (Genbank protein accession number YP_002378007.1), *Ralstonia solanacearum* putative lipase (Genbank protein accession number CBJ37498.1), *Ralstonia solanacearum* putative lipase (Genbank protein accession number NP_520203.1), *Prochlorococcus marinus* str lipase (Genbank protein accession number YP_001090842.1), *Synechococcus* sp lipase (Genbank protein accession number ZP_01086347.1), *Cyanothece* sp protein (Genbank protein accession number YP_001805548.1), *Crocosphaera watsonii* lipase 2 (Genbank protein accession number ZP_00515821.1), *Oscillatoria* sp lipase 2 (Genbank protein accession number ZP_07111441.1), *Oscillatoria* sp lipase 2 (Genbank protein accession number ZP_07111440.1), *Cyanothece* sp lipase 2 (Genbank protein accession number YP_003889715.1), *Cyanothece* sp protein (Genbank protein accession number ZP_01728450.1), *Anabaena variabilis* lipase 2 (Genbank protein accession number NP_485395.1), *Cyanothece* sp lipase 2 (Genbank protein accession number YP_325531.1), *Cyanothece* sp lipase 2 (Genbank protein accession number YP_002374003.1), *Cyanothece* sp lipase 2 (Genbank protein accession number YP_003139587.1), *Arthrospira platensis* str lipase 2 (Genbank protein accession number ZP_06380974.1), *Arthrospira maxima* protein (Genbank protein accession number ZP_03275202.1), *Microcoleus chthonoplastes* lipase (Genbank protein accession number ZP_05026554.1), *Chthoniobacter flavus* lipase 2 (Genbank protein accession number ZP_03130216.1), *Prochlorococcus marinus* str lipase (Genbank protein accession number YP_291223.1), *Trichodesmium erythraeum* lipase 2 (Genbank protein accession number YP_723108.1), *Synechococcus* sp lipase (Genbank protein accession number YP_001227853.1), *Synechococcus* sp lipase (Genbank protein accession number ZP_01125091.1), *Shewanella loihica* protein (Genbank protein accession number YP_001095448.1), *Shewanella violacea* protein (Genbank protein accession number YP_003555148.1), *Synechococcus* sp protein (Genbank protein accession number YP_001734688.1), *Cyanobium* sp lipase (Genbank protein accession number ZP_05043862.1), *Synechococcus* sp lipase (Genbank protein accession number ZP_01472701.1), *Synechococcus* sp lipase (Genbank protein accession number YP_376939.1), *Geodermatophilus obscurus* lipase 2 (Genbank protein accession number YP_003411352.1), *Prochlorococcus marinus* str lipase (Genbank protein accession number YP_001010973.1), *Prochlorococcus marinus* subsp *pastoris* str lipase (Genbank protein accession number NP_892710.1), *Prochlorococcus marinus* str lipase (Genbank protein accession number YP_001009041.1), *Prochlorococcus marinus* clone lipase (Genbank protein accession number ABE11053.1), *Synechococcus* sp lipase (Genbank protein accession number ZP_01086087.1), *Prochlorococcus marinus* str lipase (Genbank protein accession number ZP_05138407.1), *Prochlorococcus marinus* str lipase (Genbank protein accession number NP_894267.1), *Prochlorococcus marinus* str lipase (Genbank protein accession number YP_397089.1), *Prochlorococcus marinus* str lipase (Genbank protein accession number YP_001483875.1), *Synechococcus* sp lipase (Genbank protein accession number ZP_01468099.1), *Microcystis aeruginosa* protein (Genbank protein accession number CAO90905.1), *Microcystis aeruginosa* protein (Genbank protein accession number YP_001655811.1), *Arthrospira* sp lipase 2 (Genbank protein accession number ZP_07157510.1), *Synechococcus* sp lipase (Genbank protein accession number ZP_05035415.1), *Coraliomargarita akajimensis* lipase 2 (Genbank protein accession number YP_003547443.1), *Shewanella halifaxensis* protein (Genbank protein accession number YP_001675915.1), *Shewanella benthica* lipase (Genbank protein accession number ZP_02156501.1), *Prochlorococcus marinus* subsp *marinus* str lipase (Genbank protein accession number NP_875461.1), *Synechococcus* sp lipase (Genbank protein accession number NP_897577.1), *Saccharopolyspora erythraea* lipase (Genbank protein accession number YP_001106125.1), *Synechococcus* sp lipase (Genbank protein accession number ZP_05790353.1), *Deinococcus radiodurans* putative lipase (Genbank protein accession number NP_295801.1), *Streptomyces pristinaespiralis* lipase (Genbank protein accession number ZP_06912056.1), *Streptomyces violaceusniger* protein (Genbank protein accession number ZP_07611474.1), *Conexibacter woesei* lipase 2 (Genbank protein accession number YP_003395698.1), *Shewanella sediminis* lipase (Genbank protein accession number YP_001472444.1), *Shewanella piezotolerans* lipase 2 (Genbank protein accession number YP_002310059.1), *Shewanella pealeana* protein (Genbank protein accession number YP_001503478.1), *Synechococcus* sp lipase (Genbank protein accession number YP_381341.1), *Shewanella woodyi* protein (Genbank protein accession number YP_001762610.1), *Cyanobium* sp lipase (Genbank protein accession number ZP_05043963.1), *Synechococcus* sp lipase (Genbank protein accession number YP_001224489.1), *Prochlorococcus marinus* str lipase (Genbank protein accession number YP_001550943.1), *Corynebacterium glutamicum* protein (Genbank protein accession number NP_599333.1), *Corynebacterium glutamicum* protein (Genbank protein accession number YP_001136963.1), *Synechococcus* sp lipase (Genbank protein accession number ZP_01079891.1), *Allochromatium vinosum* lipase 2 (Genbank protein accession number YP_003456940.1), *Prochlorococcus marinus* str lipase (Genbank protein accession number YP_001017854.1), *Limnobacter* sp purative lipase (Genbank protein accession number ZP_01915078.1), *Thermobispora bispora* lipase 2 (Genbank protein accession number YP_003652691.1), *Synechocystis* sp protein (Genbank protein accession number BAA20430.1), and/or *Lyngbya* sp protein (Genbank protein accession number ZP_01623410.1), and conservative variants thereof.

Another lipase homolog specified herein, sll0482, carries a full-length "predicted lipase" domain (COG3675; 3e-85) and a "Lipase_3" domain (pfam01764; 2e-24) at its C-terminal half. The full length of sll0482 is observed in *Cyanothece* sp. ATTCC 51142, *Cyanothece* sp. PCC 8801 and *Synechococcus* sp. WH 5701, which are additionally or alternatively contemplated for use in transforming a host organism as disclosed herein. However, it's C-terminal half is observed in many other organisms, including bacteria, plants, and animals. Additionally or alternatively to sll0482, a host microorganism as provided herein can include a recombinant gene encoding a protein having a "predicted lipase" domain (CDD COG3675) and/or a protein having a match with Pfam PF01764, having an e-value parameter of 0.01 or less, and/or having a bit score higher than 20.3, when queried using the Pfam Profile HMM (for example, using HMMer3). The recombinant gene encoding a lipase can be, for example, an exogenous gene, or can be an endogenous gene operably linked to a heterologous promoter. Additionally or alternatively to sll0482 (SEQ ID NO:4), a host microorganism as provided herein can include an exogenous gene encoding a protein having at least 50%, at least 55%, at least 60%, at least 65%, at least 70%, at least 75%, at least 80%, or at least 85% identity to the sequence of sll0482, including proteins having 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:4, in which the host microorganism produces at least one free fatty acid in a greater amount that the same microorganism that does not include the heterologous lipase gene.

Further additional or alternate examples of genes that may be used to transform the microorganism disclosed herein can include, without limitation, genes encoding *Synechococcus* sp protein (Genbank protein accession number ZP_01084334.1), *Cyanothece* sp protein (Genbank protein accession number YP_001804176.1), *Cyanothece* sp lipase 3 (Genbank protein accession number YP_002372547.1), *Cyanothece* sp lipase 3 (Genbank protein accession number YP_003138136.1), and/or *Cyanothece* sp lipase (Genbank protein accession number ZP_05046560.1), and conservative variants thereof.

TGL2 encodes a mitochondria-localized triacylglycerol lipase from *Saccharomyces cerevisiae* and has been shown to be functional in both yeast and *E. coli* on triacylglycerol and diacylglycerol substrates. TGL2 (also known as lipase 2 (Accession number EDV08240.1), Tgl2p (Accession number NP_010343.1), YDR058C (Accession number AAS56017.1), or "triglyceride lipase" (Accession number AA66637)) is a member of the esterase-lipase superfamily and is classified in Pfam PF07819, a family of sequences related to the protein PGAP1, which has a catalytic serine containing motif that is believed to be conserved in a number of lipases (a searchable database of protein families related by sequence is available at pfam.sanger.ac.uk/, incorporated by reference herein). Additionally or alternatively to TGL2, a host microorganism as provided herein can include an exogenous gene encoding a protein having a match with Pfam PF01764, having an e-value parameter of 0.01 or less, or having a bit score higher than 20.5, when queried using the Pfam Profile HMM (for example, using HMMer3). The recombinant gene encoding a lipase can be, for example, an exogenous gene, or can be an endogenous gene operably linked to a heterologous promoter. Additionally or alternatively to TGL2, a host microorganism as provided herein can include an exogenous gene encoding a protein having at least 50%, at least 55%, at least 60%, at least 65%, at least 70%, at least 75%, at least 80%, or at least 85% identity to the sequence of TGL2 (SEQ ID NO:6), including proteins having 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:6, in which the host microorganism produces at least one free fatty acid in a greater amount that the same microorganism that does not include the heterologous lipase gene.

Examples of genes of the esterase-lipase superfamily that may be used to transform a microorganism can include, without limitation, genes coding *Zygosaccharomyces rouxii* lipase 2 (Genbank protein accession number XP_002497907), *Synechococcus* sp lipase 2 (Genbank protein accession number EDV08240.1), *Saccharomyces cerevisiae* protein (Genbank protein accession number AAS56017.1), *Saccharomyces cerevisiae* lipase (Genbank protein accession number CAA66637.1), *Saccharomyces cerevisiae* protein (Genbank protein accession number CAY78566.1), *Cryptococcus neoformans* var. *neoformans* protein (Genbank protein accession number XP_776364.1), *Kluyveromyces lactis* protein (Genbank protein accession number XP_452319.1), *Candida tropicalis* protein (Genbank protein accession number XP_002550262.1), *Vanderwaltozyma polyspora* protein (Genbank protein accession number XP_001646938.1), *Schizophyllum commune* protein (Genbank protein accession number XP_003037459.1), *Debaryomyces hansenii* protein (Genbank protein accession number XP_459944.1), *Clavispora lusitaniae* protein (Genbank protein accession number XP_002616197.1), *Pichia pastoris* protein (Genbank protein accession number XP_002491732.1), *Podospora anserina* protein (Genbank protein accession number XP_001903948.1), *Ashbya gossypii* protein (Genbank protein accession number NP_986198.1), *Nectria haematococca* protein (Genbank protein accession number XP_003050716.1), *Zygosaccharomyces rouxii* protein (Genbank protein accession number XP_002497907.1), *Candida glabrata* protein (Genbank protein accession number XP_445893.1), *Lachancea thermotolerans* protein (Genbank protein accession number XP_002554333.1), *Yarrowia lipolytica* protein (Genbank protein accession number XP_504639.1), *Gibberella zeae* protein (Genbank protein accession number XP_390196.1), *Magnaporthe grisea* lipase (Genbank protein accession number ABG79932.1), *Candida dubliniensis* lipase 2 (Genbank protein accession number XP_002416994.1), *Aspergillus clavatus* lipase (Genbank protein accession number XP_001272340.1), *Penicillium marneffei* lipase (Genbank protein accession number XP_002153153.1), *Talaromyces stipitatus* lipase (Genbank protein accession number XP_002488302.1), *Arthroderma otae* lipase (Genbank protein accession number XP_002846046.1), *Aspergillus flavus* protein (Genbank protein accession number XP_002380679.1), *Paracoccidioides brasiliensis* protein (Genbank protein accession number EEH48235.1), *Penicillium chrysogenum* protein (Genbank protein accession number XP_002568242.1), *Candida albicans* SC5314 protein (Genbank protein accession number XP_721541.1), *Ajellomyces capsulatus* lipase (Genbank protein accession number EER44477.1), *Ajellomyces capsulatus* protein (Genbank protein accession number XP_001540583.1), *Pichia guilliermondii* protein (Genbank protein accession number EDK41553.2), *Candida albicans* protein (Genbank protein accession number EEQ42820.1), *Meyerozyma guilliermondii* protein (Genbank protein accession number XP_001482631.1), *Lodderomyces elongisporus* protein (Genbank protein accession number ZP_01084334.1), *Synechococcus* sp protein (Genbank protein accession number XP_001526730.1), *Sordaria macrospora* protein (Genbank protein accession number CBI57800.1), *Ajellomyces capsulatus* lipase (Genbank protein accession number EEH10879.1), *Coprinopsis cinerea* lipase (Genbank protein accession number XP_001829084.1), *Cryptococcus neoformans* var. *neoformans* lipase (Genbank protein accession number XP_569970.1), *Aspergillus nidulans* protein (Genbank protein accession number XP_682375.1), *Aspergillus niger* protein (Genbank protein accession number XP_001395151.1), *Ajellomyces dermatitidis* lipase (Genbank protein accession number XP_002625990.1), and/or *Neurospora crassa* protein (Genbank protein accession number XP_955855.2), and conservative variants thereof.

The polypeptide encoded by the BSC1-5 ORF (SEQ ID NO:37), or amino acid sequence SEQ ID NO:38, recruits to Pfam PF12695, the Ab (alpha/beta) hydrolase 5 family (gathering cutoff 27.0) with a bit score of 30.4 and an e-value of 2.2 e-07. The BSC1-5 lipase polypeptide sequence has approximately 51% amino acid sequence identity to LipIAF1-6 (NCBI accession ADI78874; GI:298362845), a lipase of an uncultured microorganism described in Cote and Shareck (2010) *J. Ind. Microbiol. Biotechnol.* 37 (9), 883-891. Additionally or alternatively to the polypeptide encoded by the BSC1-5 ORF (SEQ ID NO:37), a host microorganism as provided herein can include an exogenous gene encoding a protein that includes an amino acid sequence having at least 50%, at least 55%, at least 60%, at least 65%, at least 70%, at least 75%, at least 80%, or at least 85% identity to SEQ ID NO:38, including proteins having amino acid sequences that have 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:38, in which the host microorganism produces at least one free fatty acid in a greater amount that the same microorganism that does not include the heterologous gene.

The polypeptide encoded by the BSC-13 ORF (SEQ ID NO:39), or amino acid sequence SEQ ID NO:40, recruits to Pfam PF01425, the Amidase family (gathering cutoff 20.1) with a bit score of 353.1 and an e-value of 1.7 e-105. The BSC-13 amidase polypeptide demonstrating lipolytic activity has approximately 84% amino acid sequence identity to an amidase signature enzyme of *Marinobacter adhaerens* HP15 (NCBI accession ADP98107; GI:311695234). It also demonstrates 75% amino acid sequence identity with an amidase of *Marinobacter algicola* DG893.1 (NCBI accession ZP_01895774; GI:149378051); 47% amino acid sequence identity with an amidase of gamma proteobacterium HdN1 (NCBI accession YP_003810088; GI:304310490); 43% amino acid sequence identity with an enantiomer selective amidase of *Streptomyces* sp. R1128 (NCBI accession AAG30199 GI:11096124); 41% amino acid sequence identity with an amidase of *Parvibaculum lavamentivorans* DS-1 (NCBI accession YP_001412078 GI:154251254); 40% amino acid sequence identity with an amidase of marine gamma proteobacterium HTCC2080 (NCBI accession ZP_01627249; GI:119505174); 40% amino acid sequence identity with a glutamyl-tRNA (Gln) amidotransferase subunit A of gamma proteobacterium NOR5-3 (NCBI accession ZP_05128598; GI:254516539); 40% amino acid sequence identity with an amidase family protein of gamma proteobacterium IMCC3088 (NCBI accession ZP_08271536; GI:329896458); and 40% amino acid sequence identity with a putative amidase of *Bradyrhizobium* sp. BTAi1 (NCBI accession YP_001241134; GI:148256549). Additionally or alternately to the polypeptide encoded by the BSC-13 ORF (SEQ ID NO:39), a host microorganism as provided herein can include an exogenous gene encoding a protein that includes an amino acid sequence having at least 50%, at least 55%, at least 60%, at least 65%, least 70%, at least 75%, at least 80%, or at least 85% identity to SEQ ID NO:40, including proteins having amino acid sequences that have 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:40, in which the host microorganism produces at least one free fatty acid in a greater amount that the same microorganism that does not include the heterologous gene.

The amino acid sequence encoded by the P500114 ORF (SEQ ID NO:46), or SEQ ID NO:47, was found to recruit to pfam PF07859, the Ab (alpha/beta) hydrolase 3 family (gathering cutoff 20.7) with a bit score of 230.6 and an e-value of 1.2 e-68. The P500114 polypeptide has 50% amino acid sequence identity to lipH of *Burkholderia thailandensis* TXDOH (NCBI accession ZP_02371858; GI:167578984); 50% amino acid sequence identity to a lipase/esterase of *Acaryochloris marina* MBIC11017 (NCBI accession YP_001514890; GI:158333718); 49% amino acid sequence identity to a hypothetical protein BthaA_17529 of *Burkholderia thailandensis* E264 (ZP_05589243; GI:257140981); 49% amino acid sequence identity to LipH of *Burkholderia thailandensis* E264 (ABC34438; GI:83650374); 49% amino acid sequence identity to a lipolytic enzyme of an uncultured bacterium (Hu et al. (2010) *FEMS Microbiol E. coli* 7: 228-

237) (ACL67843.1 GI:219957624); and 44% amino acid sequence identity to a lipase/esterase of *Candidatus Chloracidobacterium thermophilum* B (YP_004862114; GI:347754550). Additionally or alternately to the polypeptide encoded by the P500114 ORF (SEQ ID NO:46), a host microorganism as provided herein can include an exogenous gene encoding a protein that includes an amino acid sequence having at least 50%, at least 55%, at least 60%, at least 65%, least 70%, at least 75%, at least 80%, or at least 85% identity to SEQ ID NO:47, including proteins having amino acid sequences that have 85 to 87% identity, 87 to 90% identity, 90 to 92% identity, 92 to 94% identity, 94 to 95% identity, 95 to 96% identity, 96 to 97% identity, 97 to 98% identity, 98 to 99% identity, 99 to 100% identity to SEQ ID NO:47, in which the host microorganism produces at least one free fatty acid in a greater amount that the same microorganism that does not include the heterologous gene.

The provided examples of genes polypeptides having lipolytic activity are exemplary and not limiting. As provided in the examples, transformation of microorganisms with genes encoding five different types of lipase (of different protein families) from both prokaryotes and eukaryotes resulted in the production of free fatty acids, demonstrating the applicability of genes encoding a broad range of proteins with lipase function. Also considered for use in the engineered microorganisms provided herein are any members of the amidase family (recruiting to Pfam PF01425, the Amidase family, with a bit score higher than the gathering cutoff of 20.1, and preferably an e-value of less than 0.01). A recombinant lipase or amidase gene can optionally be engineered to eliminate, alter, or add a heterologous protein localization sequence, such as, for example, a localization sequence for directing the lipase to the mitochondria, chloroplasts, the endoplasmic reticulum or a cell membrane, or a sequence directing secretion of the polypeptide having lipolytic activity.

The present invention relates, in some embodiments, to recombinant microorganisms including a recombinant nucleic acid molecule including a nucleic acid sequence that encodes an amino acid sequence that shares at least about 50%, at least about 55%, at least about 60%, at least about 65%, at least about 70%, 75%, 80% or 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the amino acid sequence of SEQ ID NOs: 2, 4, 6, 38, 40, and/or 47 operably linked to a heterologous promoter. Additionally or alternately, the present invention relates, in some embodiments, to recombinant microorganisms transformed with an isolated nucleic acid molecule including a nucleic acid sequence that shares at least about 70%, at least about 75%, at least about 80%, or at least about 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the nucleic acid sequence of SEQ ID NOs:1, 3, 5, 37, 39, and/or 46. Specifically contemplated are genomic or synthetic DNA sequences, cDNA, and mRNA, as well as nucleic acids based on alternative backbones and/or including alternative bases, whether derived from natural sources or synthesized.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner can include: a "charged/polar group," including Glu, Asp, Asn, Gln, Lys, Arg, and His; an "aromatic or cyclic group," including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group," comprising Lys, Arg and His; the "negatively-charged sub-group," comprising Glu and Asp; and the "polar sub-group" comprising Asn and Gln. In another example, the aromatic or cyclic group can be sub-divided into sub-groups including: the "nitrogen ring sub-group," comprising Pro, His, and Trp; and the "phenyl sub-group" comprising Phe and Tyr. In another further example, the aliphatic group can be sub-divided into sub-groups including: the "large aliphatic non-polar sub-group," comprising Val, Leu, and Be; the "aliphatic slightly-polar sub-group," comprising Met, Ser, Thr, and Cys; and the "small-residue sub-group," comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn such that a free —NH2 can be maintained.

A "conservative variant" of a polypeptide is a polypeptide having one or more conservative amino acid substitutions with respect to the reference polypeptide, in which the activity, substrate affinity, binding affinity of the polypeptide does not substantially differ from that of the reference polypeptide.

A substitution, insertion, or deletion can be said to adversely affect the protein when the altered sequence substantially inhibits a biological function associated with the protein. For example, included herein are variants of lipases, esterases, or amidases in which the substrate affinity or turnover rate of the variant lipolytic enzyme is not reduced by more than 5% with respect to the lipolytic enzyme from which the variant is derived, or in which the production of free fatty acids by a host microorganism that expresses the variant enzyme is not less than 95% of the production of free fatty acids by the same microorganism expressing the lipolytic enzyme from which the variant was derived, in which the enzyme variant and lipolytic enzyme are expressed under the same conditions using the same expression construct configurations.

Percent identity or homology with respect to such sequences is defined herein as the percentage of amino acid residues in the candidate sequence that are identical with the known peptides, after aligning the sequences and introducing gaps, if necessary, to achieve the maximum percent homology and not considering any conservative substitutions as part of the sequence identity. N-terminal, C-terminal, and/or internal deletions and/or insertions of up to ten, twenty, thirty, forty, fifty, or sixty amino acids into the polypeptide sequence shall not be construed as affecting homology.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul et al. (1997), Nucleic Acids Res. 25, 3389-3402, and Karlin et al. (1990), Proc. Natl. Acad. Sci. USA 87, 2264-2268, both fully incorporated by reference), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul et al. (1994), Nature Genetics 6, 119-129, which is fully incorporated by reference. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff et al. (1992), Proc. Natl. Acad. Sci. USA 89, 10915-10919, fully incorporated by reference), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, the present invention also includes recombinant microorganisms which express protein molecules having the amino acid sequence at least about 50%, 55%, 60%, or 65%, for example, at least about 70%, 75%, 80%, or 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the polypeptide sequence of SEQ ID NO:2, 4, 6, 38, 40, and/or 47; fragments thereof comprising a consecutive sequence of at least about 50, for example at least about 75, at least about 100, at least about 125, at least about 150 or more amino acid residues of the entire protein; amino acid sequence variants of such sequences, wherein at least one amino acid residue has been inserted N- and/or C-terminal to, and/or within, the disclosed sequence(s) which contain(s) the insertion and substitution; amino acid sequence variants of the disclosed sequence, and/or their fragments as defined above. Contemplated variants can additionally or alternately include those containing predetermined mutations by, e.g., homologous recombination, site-directed or PCR mutagenesis, and the corresponding proteins of other species, including, but not limited to, those described herein, the alleles or other naturally occurring variants of the family of proteins which contain the insertion and substitution; and/or derivatives wherein the protein has been covalently modified by substitution, chemical, enzymatic, or other appropriate means with a moiety other than a naturally occurring amino acid which contains the insertion and substitution (for example, a detectable moiety such as an enzyme).

Another indication that two nucleic acid sequences have substantial homology is that the two molecules hybridize specifically to each other under stringent conditions. The phrase "hybridize specifically to" refers to the binding, duplexing, and/or hybridizing of a molecule only to a particular nucleotide sequence under stringent conditions, including when that sequence is present in a complex mixture (e.g., total cellular) of DNA and/or RNA. "Binds substantially" refers to complementary hybridization between a probe nucleic acid and a target nucleic acid and embraces minor mismatches that can be substantially accommodated by reducing the stringency of the hybridization media to achieve the desired detection of the target polynucleotide sequence. "Stringent hybridization conditions" and "stringent hybridization wash conditions", in the context of nucleic acid hybridization experiments such as Southern and northern hybridizations, are sequence dependent and are different under different environmental parameters.

Longer sequences can tend to hybridize specifically at higher temperatures. Generally, highly stringent hybridization and wash conditions can be selected to be about 5° C. lower than the thermal melting point (Tm) for the specific sequence at a defined ionic strength and pH. Typically, under "stringent conditions" a probe will generally hybridize to its target subsequence, but not to unrelated sequences.

The Tm is defined herein as the temperature (under defined ionic strength and pH) at which approximately 50% of the target sequence hybridizes to a perfectly matched probe. Very stringent conditions can be selected to be equal to the Tm for a particular probe. An example of stringent hybridization conditions for hybridization of complementary nucleic acids that have more than 100 complementary residues on a filter in a Southern or northern blot is about 50% formamide with about 1 mg of heparin at about 42° C., with the hybridization being carried out overnight (for about 6-16 hours). An example of highly stringent wash conditions includes about 0.15M NaCl at about 72° C. for about 15 minutes. An example of stringent wash conditions is a ~0.2×SSC wash at about 65° C. for about 15 minutes (see Sambrook, Molecular Cloning—A Laboratory Manual (2005), Cold Spring Harbor Laboratory Press). Often, a high stringency wash can be preceded by a low stringency wash to remove background probe signal. An example of a medium stringency wash for a duplex of, e.g., more than 100 nucleotides, is ~1×SSC at about 45° C. for about 15 minutes. An example of a low stringency wash for a duplex of, e.g., more than 100 nucleotides, is ~4-6×SSC at about 40° C. for about 15 minutes. For short probes (e.g., about 10 to 50 nucleotides), stringent conditions can typically involve salt concentrations of less than about 1.0 M Na ion, typically from about 0.01 to about 1.0 M Na ion, concentration (or other salts) at a pH of about 7.0 to about 8.3, with typical temperatures of at least about 30° C. Stringent conditions can additionally or alternately be achieved with the addition of destabilizing agents such as formamide. In general, a signal to noise ratio of about 2× (or higher) than that observed for an unrelated probe in the particular hybridization assay can indicate detection of a specific hybridization.

In some embodiments, the present invention relates to a recombinant microorganism that includes at least one recombinant expression system for at least one gene encoding a polypeptide having lipolytic activity that operates to liberate and/or release fatty acids from biomolecules such as, for example, lipid molecules, such as monoglycerides, diglycerides, and/or triglycerides. In some embodiments, the recombinant microorganism is a microorganism that does not substantially accumulate triglycerides prior to or in the absence of expression of the lipase gene. A "free fatty acid", as used herein, is meant to refer to a non-esterified carboxylic acid having an alkyl chain of at least 3 carbons (that is, an acyl chain of at least 4 carbons) or its corresponding carboxylate anion, denoted as RCOOH or RCOO— respectively, where R is an alkyl chain of between 3 and 23 carbons. A "free fatty acid" is substantially unassociated, e.g., with a protein, within or outside an organism (e.g., globular and/or micellular storage within an organism, without esterification, can still qualify as a free fatty acid). Thus, a free fatty acid according to the present invention need not necessarily be a strict acid or be structurally "free", but a free fatty acid specifically does not include an acyl moiety whose carboxylate oxygen is covalently linked to any other moiety besides a hydrogen atom (meaning that fatty acid esters are specifically not included in free fatty acids). However, a free fatty acid can advantageously include an acyl moiety containing at least four carbons (preferably at least 6 carbons, for example at least 8 carbons), in which the acyl moiety (i) is covalently linked to a hydrogen atom, (ii) has an ionic charge, to which a counterion can be associated (even if loosely and/or solvent-separated), and/or (iii) is associated, but not covalently bonded to another moiety that is relatively easily transformable into the corresponding acid form or the corresponding ionic form (e.g., through hydrogen-bonding or the like). Non-limiting examples of counterions can include metals salts (such as calcium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof.

In additional or alternate embodiments, the lipolytic enzyme that may be used in the present invention can include, but is not limited to, the polypeptides of sll1969 (SEQ ID NO:2), sll0482 (SEQ ID NO:4), TGL2 (SEQ ID NO:6), the lipolytic polypeptide that comprises SEQ ID NO:38, the lipolytic polypeptide that comprises SEQ ID NO:40, and/or the lipolytic polypeptide that comprises SEQ ID NO:47.

In some embodiments, the recombinant microorganisms can be transformed with an isolated nucleic acid molecule encoding a polypeptide with lipolytic activity. Additionally or alternately contemplated are recombinant microorganisms that are engineered to include gene regulatory sequences that induce or increase expression of an endogenous gene encoding a lipolytic enzyme. For example, a microorganism can be engineered such that a heterologous promoter is inserted upstream of a coding region of an endogenous gene encoding a lipolytic enzyme. The heterologous promoter can replace an endogenous promoter and/or can be inserted upstream or downstream of the endogenous promoter that regulates expression of the endogenous gene, for example using homologous recombination or site-specific recombination. The heterologous promoter can be a constitutive promoter or an inducible promoter that increases expression of the endogenous gene encoding a lipolytic enzyme.

Although this section describes mostly genes encoding polypeptides having lipolytic activity, it should be understood that the invention can additionally or alternately include microorganisms having at least one exogenous nucleic acid molecule that encodes a polypeptide whose expression results in the production of one or more free fatty acids or free fatty acid derivatives, particularly in combination with an attenuation and/or disruption of a gene encoding an acyl-ACP synthetase (or like functionality). Polypeptides whose expression result in the production of one or more free fatty acids or fatty acid derivatives can include, but are not necessarily limited to, thioesterases, lipases, amidases, and the like, and combinations thereof. For example, such expressed polypeptides can encode one or more of an acyl-ACP thioesterase, an acyl-CoA thioesterase, a 4-hydroxybenzoate thioesterase, an amidase, and a lipase, including, without limitation, a lipase of the lipase 2 superfamily, a member of the esterase-lipase superfamily, and proteins that include domains that identify the proteins as members of a pfam belonging to the AB Hydrolase Pfam clan (CL0028), such as, for example, Pfam PF01674, Pfam PF01764, Pfam PF07819, Pfam PF03583, Pfam PF00151, and the like.

For example, also encompassed by the invention are microorganisms that include, in addition to a non-native nucleic acid molecules encoding a polypeptide having lipolytic activity, a non-native nucleic acid molecule encoding a thioesterase, such as, for example, an acyl-ACP thioesterase, an acyl-CoA thioesterase, or a hydroxylbenzoyl thioesterase. For example, a microorgansim for the production of free fatty acids in some embodiments can be transformed with a gene encoding an exogenous acyl-ACP thioesterase, such as a gene encoding a polypeptide that when queried against the pfam database, provides a match with Pfam PF01643 having a bit score of less than or equal to 20.3 (the gathering cut-off for PF01643). The exogenous acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g. *Cuphea carthagenensis, Cuphea wrightii* (e.g. AAC49784.1 GI:1336008), *Cuphea lanceolata* (e.g. CAA54060, GI495227), *Cuphea palustris*, (e.g. AAC49783.1 GI:1336006; AAC49179.1 GI:1215718); *Cuphea hookeriana* (e.g. AAC72882.1 GI:3859830; AAC49269.1 GI:1292906; AAC72881.1 GI:3859828; AAC72883.1 GI:3859832), *Cuphea calophylla* (e.g. ABB71580.1 GI:81361963)) or genes from other higher plant species. For example, a microorganism used in the methods and cultures disclosed herein can include a gene encoding an acyl-ACP thioesterase from species such as but not limited to, *Arabidopsis* (XP_002885681.1 GI:297835598; NP_172327.1 GI:15223236); *Arachis hypogaea* (e.g. AB038556.1 GI:133754634); *Brassica* species (e.g. CAA52069.1 GI:435011), *Camellia oleifera* ((e.g. ACQ57189.1 GI:229358082); *Cinnamonum camphorum* (e.g. AAC49151.1 GI:1143156); *Cocos nucifera; Glycine max* (e.g. ABD91726.1 GI:90192131); *Garcinia mangostana* (e.g. AAB51525.1 GI:1930081); *Gossypium hirsutum* (e.g. AAD01982.1 GI:4104242); *Helianthus annuus* (e.g. AAQ08226 GI:33325244); *Jatropha curcas* (e.g. ABU96744.1 GI:156900676); *Macadamia tetraphylla* (e.g. ADA79524.1 GI:282160399); *Elaeis oleifera* (e.g. AAM09524.1 GI:20067070); *Oryza sativa* (e.g. BAA83582.1 GI:5803272); *Populus tomentosa* (e.g. ABC47311 GI:83778888); *Umbellularia californica* (e.g. AAC49001.1 GI:595955); *Ulmus Americana* (e.g. AAB71731.1 GI:2459533); and *Zea mays* (ACG41291.1 GI:195643646), or any of those disclosed in U.S. Pat. No. 5,455,167; U.S. Pat. No. 5,654,495; and U.S. Pat. No. 5,455, 167; all incorporated by reference herein in their entireties. Further included are acyl-ACP thioesterases from mosses (Bryophyta), such as, for example, *Physcomitrella patens*, (e.g. XP_001770108 GI:168035219). These examples are not limiting with regard to the types or specific examples of acyl-ACP thioesterase genes that can be used.

Further examples of thioesterases that can be expressed by a microorganism that includes a non-native gene encoding a polypeptide with lipolytic activity are acyl-ACP thioesterase genes from prokaryotic organisms. Illustrative examples of prokaryotic acyl-ACP thioesterases that may be expressed by a microorganism that also expresses a lipolytic enzyme, include but are not limited to acyl-ACP thioesterases from *Desulfovibrio desulfuricans* (e.g. Q312L1 GI:123552742); *Elusimicrobium minutum* (e.g. ACC98705 GI:186971720); *Carboxydothermus hydrogenoformans* (e.g. YP_359670 GI:78042959); *Clostridium thermocellum* (e.g. YP_001039461 GI:125975551); *Moorella thermoacetica* (e.g. YP_431036 GI:83591027); *Geobacter metallireducens* (e.g. YP_384688 GI:78222941); *Salinibacter ruber* (e.g. YP_444210 GI:83814393); *Microscilla marina* (e.g. EAY28464 123988858); *Parabacteroides distasonis* (e.g. YP_001303423 GI:150008680); *Enterococcus faecalis* (e.g. ZP_03949391 GI:227519342); *Lactobacillus plantarum* (e.g. YP_003062170 GI:254555753); *Leuconostoc mesenteroides* (e.g. YP_817783 GI:116617412); *Oenococcus oeni* (e.g. ZP_01544069 GI:118586629); *Mycobacterium smegmatis* (e.g. ABK74560 GI:118173664); *Mycobacterium vanbaalenii* (e.g. ABM11638 GI:119954633); *Rhodococcus erythropolis* (e.g. ZP_04385507 GI:229491686; *Rhodococcus opacus* (e.g. YP_002778825 GI:226361047), or any of those disclosed in provisional patent application 61/426,555 entitled "Prokaryotic Acyl-ACP Thioesterases for Producing Fatty Acids in Genetically Engineered Microorganisms", filed on Dec. 23, 2010, and which is incorporated herein by reference in its entirety.

In additional embodiments, a gene encoding an acyl-CoA thioesterase can be introduced into a host microorganism that includes an non-native nucleic acid molecule encoding a polypeptide having lipolytic activity. An acyl-CoA thioesterase gene transformed into a microorganism for the production of free fatty acids or fatty acid derivatives can be from a plant, animal, or microbial source. For example, a gene encoding the TesA or TesB thioesterase of *E. coli*, or a variant thereof, for example, an acyl-CoA thioesterase such as not limited to a variant as disclosed in WO 2010/075483, incorporated by reference herein in its entirety, can be introduced into a microorganism. Also included are genes encoding proteins that when queried against the Pfam database of protein families are identified as members of Pfam PF02551 (acyl-CoA thioesterase), where the bit score is equal to or greater than the gathering cut off (20.7).

Alternately or in addition, the microorganism that includes a non-native gene encoding a polypeptide having lipolytic activity can include one or more genes encoding an exogenous hydroxybenzoate thioesterase, for example an exogenous 4-hydroxybenzoate thioesterase or 4-chlorobenzoate thioesterase. Genes encoding hydroxybenzoate thioesterases that may be useful in a microorganism for producing free fatty acids or fatty acid derivatives can include, for example, those disclosed in provisional patent application 61/426,568 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 23, 2010, and which is incorporated herein by reference in its entirety, 4-hydroxybenzoate thioesterases from *Bacillus* species and *Geobacillus* species, as well as 4-hydroxybenzoate thioesterases of *Acidiphilium*, *Bartonella*, *Rhodopseudomonas*, *Magnetospirillum*, *Burkholderia*, *Granulibacter*, *Rhizobium*, and *Labrenzia* species, or the like, or combinations thereof.

Still further additionally or alternately, the microorganism can include nucleic acid molecules encoding variants of naturally-occurring acyl-ACP thioesterases, acyl-CoA thioesterases, hydroxybenzoate thioesterases, amidases, or lipases, in which the variants have at least 80%, for example at least 85%, at least 90%, or at least 95%, identity to the amino acid sequences accessed by the provided or referenced Genbank Accession Numbers, in which the variants have at least the level of activity (e.g. thioesterase, amidase, or lipase activity) as the reference sequence.

Further Modifications for Producing Fatty Acid Derivatives

Additionally or alternately to providing an expression system for one or more thioesterase genes in a microorganism that includes a non-native gene encoding a polypeptide having lipolytic activity, further modifications in the microorganism may be made to enable the production of fatty acid derivatives. For example, in some embodiments, the genetically engineered microorganism that includes a non-native gene encoding a lipolytic enzyme can further include one or more exogenous nucleic acid molecules encoding an exogenous acyl-CoA reductase, carboxylic acid reductase, and/or an exogenous or non-native acyl-ACP reductase for the production of a fatty alcohol. Alternatively or in addition, the genetically engineered photosynthetic microorganism of the described invention can produce a wax ester and can include one or more exogenous or non-native nucleic acid molecules encoding an acyl-CoA reductase, carboxylic acid reductase, or acyl-ACP reductase, and an exogenous wax synthase. Wax esters include an A chain and a B chain linked through an ester bond, one or both of which can be derived from a fatty acid generated by the expressed lipolytic enzyme and, optionally, an expressed thioesterase. Wax esters produced by a transgenic microorganism that includes an exogenous nucleic acid molecule encoding a polypeptide having lipolytic activity therefore can have A chain lengths of from 8 to 24 carbons, for example, and B chain lengths of from 8 to 24 carbons, and preferably A chains and B chains of 16 carbons or greater. The wax esters synthesized by the photosynthetic host microorganism for example can have A+B chain lengths of, for example, 16 to 48 carbons, 32 to 40 carbons, or 32 to 36 carbons.

In some embodiments, the microorganism that expresses a non-native gene that encodes a polypeptide having lipolytic activity can produce an alkane or alkene and can include at least one exogenous or non-native nucleic acid molecule encoding an exogenous fatty acid decarboxylase or an exogenous fatty aldehyde decarbonylase, and additionally can further include at least one exogenous nucleic acid molecule encoding an exogenous acyl-CoA reductase, carboxylic acid reductase, or acyl-ACP reductase. Alkanes and alkenes produced by a microorganism that includes a non-native nucleic acid molecule encoding a polypeptide having lipolytic activity can, for example, have chain lengths of 7, 9, 11, 13, 15, 17, 19, 21, and/or 23 carbons, for example, chain lengths of 7, 9, 11, 13, 15, and/or 17 carbons, or chain lengths of 7, 9, 11, 13, and/or 15 carbons, or chain lengths of 11, 13, and/or 15 carbons, or for example chain lengths of 15 and 17 carbons.

Additionally but optionally, a genetically engineered microorganism that produces a fatty alcohol, fatty aldehyde, wax ester, alkane, or alkene may optionally further include an exogenous nucleic acid molecule encoding an acyl-CoA synthetase.

Other Modifications

Additionally or alternately to providing an expression system for one or more appropriate recombinant genes, such as genes encoding polypeptides having lipolytic activity, further modifications in the microorganism may be made. Specifically, the present invention also provides recombinant microorganisms that further include at least one endogenous gene that is attenuated or disrupted. Such an endogenous gene that can be attenuated or disrupted in the recombinant microorganism includes, but is not limited to, a gene encoding any of an acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof.

For example, the microorganism can be modified such that one or more genes that encode beta-oxidation pathway enzymes have been inactivated or downregulated, and/or such that the enzymes themselves that are operative on such beta-oxidation pathways may be inhibited. This would prevent the degradation of fatty acids released from acyl-ACPs, thus enhancing the yield of fatty acids or fatty acid derivatives. Mutations in a gene encoding acyl-CoA synthetase and/or acyl-CoA oxidase, such that the activity of one or more of these enzymes could be diminished, would additionally or alternately be effective in increasing the yield of produced and/or released fatty acids or fatty acid derivatives. Mutations in a gene can be introduced either by recombinant or non-recombinant methods. These enzymes and their genes are known and may be targeted specifically by disruption, deletion, generation of antisense sequences, generation of ribozymes, RNAi, and/or other recombinant approaches known to the practitioner. Inactivation of the genes can additionally or alternately be accomplished by random mutation techniques such as exposure to UV and/or chemical mutagens, and the resulting cells can be screened for successful mutants. The proteins themselves can be inhibited by intracellular generation of appropriate antibodies, intracellular generation of peptide inhibitors, or the like, or some combination thereof.

Still further additionally or alternately, the microorganism can be modified such that the acyl-ACP synthetase (AAS) gene is inactivated or downregulated, or mutated such that the enzymes themselves can have reduced activity. Acyl-ACP synthetase (AAS) converts free fatty acid to acyl-ACP for free fatty acid recycling and membrane restructuring, such that strains having a mutated or disrupted AAS gene can exhibit an enhancement in the yield of fatty acids produced by the lipase-expressing microorganisms, as shown in Example 2.

Yet further additionally or alternately to any of the above modifications, the microorganism can be transformed with exogenous acyl-ACP thioesterase, acyl-CoA thioesterase, or 4-hydroxybenzoyl thioesterase for production of additional free fatty acids, which can optionally but preferably be released or secreted into culture medium, or may be converted to fatty acid derivatives.

Again still further additionally or alternately, the photosynthetic microorganism can be modified such that one or more genes that encode storage carbohydrate and/or polyhydroxyalkanoate (PHA) biosynthesis pathway enzymes can be inactivated or downregulated, and/or such that the enzymes themselves that are operative on such pathways are inhibited. Examples include, but are not limited to, enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

Expression Systems

The recombinant microorganisms of the present invention, in some embodiments, are transformed with exogenous genes by the introduction of appropriate expression vectors.

"Expression vector" or "expression construct" refers to a nucleic acid that has been generated via human intervention, including by recombinant means and/or direct chemical synthesis, with a series of specified nucleic acid elements that permit transcription and/or translation of a particular nucleic acid in a host cell. The expression vector can be a plasmid, a part of a plasmid, a viral construct, a nucleic acid fragment, or the like, or a combination thereof. Typically, the expression vector can include a nucleic acid to be transcribed operably linked to a promoter in an "expression cassette". Moreover, "inducible promoter" refers a promoter that mediates transcription of an operably linked gene in response to a particular stimulus. "Operable linkage" is a functional linkage between two nucleic acid sequences, such as a control sequence (typically a promoter) and the linked sequence (typically a sequence that encodes a protein and/or other biomolecule, also called a coding sequence). A promoter is in operable linkage with an exogenous gene if it can mediate transcription of the gene.

Vectors can be introduced into prokaryotic and eukaryotic cells via conventional transformation and/or transfection techniques. The terms "transformation" and "transfection", conjugation and transduction, as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

For example, algae and photosynthetic bacteria can be transformed by any suitable methods, including, as nonlimiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017), electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation (WO2009/140701), incubation with DNA in the presence of or after pre-treatment with any of poly(amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, and/or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365), or the like, or combinations thereof. Agrobacterium-mediated transformation can additionally or alternately be performed on algal cells, for example after removing or wounding the algal cell wall (e.g., PCT Publication No. WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; PCT Publication No. WO 2003/091413; PCT Publication No. WO 2005/005643; and PCT Publication No. WO 2007/133558, all incorporated herein by reference in their entireties).

For optimal expression of a recombinant protein, in many instances it can be beneficial to employ coding sequences that produce mRNA with codons preferentially used by the host cell to be transformed. Thus, for an enhanced expression of transgenes, the codon usage of the transgene can be matched with the specific codon bias of the organism in which the transgene is desired to be expressed. For example, methods of recoding genes for expression in microalgae are described in U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons can be changed to reflect a preferred codon usage of a host microorganism, and in some embodiments, one or more codons can be changed to codons that are not necessarily the most preferred codon of the host microorganism encoding a particular amino acid. Additional information for codon optimization is available, e.g., at the codon usage database of GenBank.

Accordingly, the present invention also provides, in some embodiments, for recombinant microorganisms transformed with an isolated nucleic acid molecule including a nucleic acid sequence that is codon-optimized for expression in the recombinant microorganism.

In some embodiments, the present invention additionally or alternately provides recombinant microorganisms transformed with an isolated nucleic acid molecule including a nucleic acid sequence that is operably linked to one or more expression control elements.

In some preferred embodiments of the invention, a gene (such as a gene as disclosed herein), can be cloned into an expression vector for transformation into a fungus, an alga, or a photosynthetic or nonphotosynthetic bacterium. The vector can include sequences that promote expression of the transgene of interest (e.g., an exogenous lipase gene), such as a promoter, and may optionally include, for expression in eukaryotic cells, an intron sequence, a sequence having a polyadenylation signal, or the like, or combinations thereof. Alternatively, if the vector does not contain a promoter in operable linkage with the gene of interest, the gene can be transformed into the cells such that it becomes operably linked to an endogenous promoter by homologous recombination, site specific integration, and/or vector integration.

Alternatively, the vector introduced in to a microorganism can include a promoter or transcriptional enhancer sequence not in operable linkage with a gene of interest, where the promoter or enhancer is positioned next to one or more sequences for directing the promoter to the chromosomal locus of a gene for producing fatty acids (e.g., an endogenous lipase gene). For example, sequences for homologous recombination or site-specific recombination can be engineered to flank a transcriptional regulatory sequence in a transformation vector, such that following transformation into the cells the regulatory sequence integrates into the host chromosome becomes operably linked to an endogenous gene by homologous recombination, site specific integration, and/or vector integration.

Vectors designed for expression of a gene in microalgae can alternatively or in addition include a promoter active in microalgae operably linked to the exogenous gene being introduced. A variety of gene promoters and terminators that function in green algae can be utilized in expression vectors, including, but not limited to, promoters and/or terminators from *Chlamydomonas* and other algae (see, for example, U.S. Pat. No. 7,745,696; *Plant Cell Physiol* 49: 625-632 (2008); *Eukaryotic Cell* 2:995-1002 (2003), *Plant Cell Rep* 23: 727-735 (2005), *Plant Cell Rep* 25: 582-591 (2006)), promoters and/or terminators from viruses, synthetic promoters and/or terminators, or the like, or combinations thereof.

For transformation of diatoms, a variety of gene promoters that function in diatoms can be utilized in these expression vectors, including, but not limited to: 1) promoters from *Thalassiosira* and other heterokont algae, promoters from viruses, synthetic promoters, or the like, or combinations thereof. Promoters from *Thalassiosira pseudonana* and/or *Phaeodactylum tricornutum* that could be suitable for use in expression vectors can include an alpha-tubulin promoter, a beta-tubulin promoter, an actin promoter, or a combination thereof. The terminators associated with these genes, other diatom genes, and/or particular heterologous genes can be used to stop transcription and/or provide the appropriate signal, e.g., for polyadenylation.

In some instances, it can be advantageous to express an exogenous and/or heterologous enzyme, such as but not limited to a lipase or an amidase, at a certain point during the growth of the transgenic host, e.g., to minimize any deleterious effects on the growth of the transgenic organism and/or to maximize production of the fatty acid product of interest. In such instances, one or more exogenous genes introduced into the transgenic organism can be operably linked to an inducible promoter. The promoter can be, for example, a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. No. 5,750,385, U.S. Pat. No. 5,639,952), metals (*Eukaryotic Cell* 2:995-1002 (2003)) or temperature (U.S. Pat. No. 5,447,858; Abe et al. *Plant Cell Physiol.* 49: 625-632 (2008); Shroda et al. *Plant J.* 21: 121-131 (2000)). The foregoing list is exemplary and not limiting. The promoter sequences can be from any organism, provided that they are functional in the host organism.

For transformation of cyanobacteria, a variety of promoters that function in cyanobacteria can be utilized, including, but not limited to, the lac, tac, and trc promoters, as well as derivatives that are also inducible by the addition of isopropyl β-D-1-thiogalactopyranoside (IPTG) such as the trcY or trcE promoter. Other promoters that may find use in the invention include promoters that are naturally associated with transposon- or bacterial chromosome-borne antibiotic resistance genes (e.g., neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. Promoters isolated from cyanobacteria that can be used can include but are not limited to the following: nrs (nickel-inducible), secA (secretion; controlled by the redox state of the cell), rbc (Rubisco operon), psaAB (PS I reaction center proteins; light regulated), psbA (Dl protein of PSII; light-inducible), and the like, and combinations thereof. In some embodiments, the promoters are regulated by nitrogen compounds, such as, for example, nar, ntc, nir or nrt promoters. In some embodiments, the promoters are regulated by phosphate (e.g., pho or pst promoters) or metals (e.g., the nrs promoter (Liu and Curtis (2009) *Proc Natl Acad Sciences USA* 106: 21550-21554), or the petE promoter (Buikema and Haselkorn (2001) *Proc Natl Acad Sciences USA* 98: 2729-2734)). Inducible promoters, as used in the constructs of the present invention, can use one or more portions or domains of the aforementioned promoters and/or other inducible promoters fused to at least a portion of a different promoter that can operate in the host organism, e.g., to confer inducibility on a promoter that operates in the host species.

Likewise, a wide variety of transcriptional terminators can be used for expression vector construction. Examples of possible terminators can include, but are not limited to, psbA, psaAB, rbc, secA, T7 coat protein, and the like, and combinations thereof.

Transformation vectors can additionally or alternately include a selectable marker, such as but not limited to a drug resistance gene, an herbicide resistance gene, a metabolic enzyme and/or factor required for survival of the host (for example, an auxotrophic marker), or the like, or a combination thereof. Transformed cells can be optionally selected based upon the ability to grow in the presence of the antibiotic and/or other selectable marker under conditions in which cells lacking the resistance cassette or auxotrophic marker could not grow. Further additionally or alternately, a non-selectable marker may be present on a vector, such as a gene encoding a fluorescent protein or enzyme that generates a detectable reaction product.

Expression vectors can be introduced into the cyanobacterial strains by standard methods, including, but not limited to, natural DNA uptake, conjugation, electroporation, particle bombardment, abrasion with glass beads, SiC fibers, or other particles, or the like, or combinations thereof. The vectors can be: (1) targeted for integration into the cyanobacterial chromosome, e.g., by including flanking sequences that enable homologous recombination into the chromosome; (2) targeted for integration into endogenous cyanobacterial plasmids, e.g., by including flanking sequences that enable homologous recombination into the endogenous plasmids; and/or (3) designed such that the expression vectors replicate within the chosen host.

According to some preferable embodiments, the present invention can involve recombinant microorganisms transformed with an isolated nucleic acid molecule including a nucleic acid sequence that is under control of a heterologous promoter. In such embodiments, the heterologous promoter can be an inducible promoter, such as an isopropyl β-D-1-thiogalactopyranoside (IPTG)-inducible promoter, for example, an nrs promoter or a lac, tac, and/or trc promoter, such as trcE and/or trcY.

Methods of Producing Fatty Acids and Fatty Acid Derivatives

The invention encompasses methods of producing a free fatty acid or a derivative thereof by culturing the recombinant microorganisms described herein under conditions that allow expression of the non-native gene encoding a polypeptide having lipolytic activity to produce at least one free fatty acid or derivative thereof. Additionally, the method can include isolating at least one free fatty acid or fatty acid derivative. A free fatty acid or fatty acid derivative can be isolated from the culture medium, the microorganism, or a combination thereof. Optionally but preferably at least a portion of the free fatty acid or fatty acid derivative produced by the recombinant microorganisms is released into the growth media by the microorganism. In some embodiments, the expression of the polypeptide encoded by the nucleic acid molecule described herein can be induced in the recombinant microorganism to produce the free fatty acid or fatty acid derivative.

The recombinant microorganism in some embodiments does not substantially accumulate triacylglycerols (TAGs) during the culturing period. Additionally or alternately, the recombinant microorganism can express a non-native gene encoding a polypeptide having lipolytic activity (such as a lipase or amidase gene) during the period of culturing when fatty acid and/or lipid synthesis is occurring. In some such embodiments, expression of the non-native (lipase) gene does not result in production of an alkyl ester, such as a fatty acid ethyl ester, fatty acid propyl ester, fatty acid methyl ester, or the like, and preferably results in production of a free fatty acid, or a fatty alcohol, wax ester, alkane, or alkene.

Releasing and secreting, as used herein, are used interchangeably to refer to active and/or passive transport mechanisms wherein fatty acids are able to cross the cell membrane. Examples of such transport mechanisms can include, but are not necessarily limited to, gradient diffusion, facilitated diffusion, active transport, and combinations thereof.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. Nonlimiting examples of selected and/or controlled conditions can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism can be grown heterotrophically or mixotrophically, using both light and a reduced carbon source. Additionally or alternately, the microorganism can be cultured phototrophically. When growing phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture.

Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of strains of microorganisms. For example, various fresh water and salt water media can include those described in Barsanti, L. and Gualtieri, P. (2005) Algae: Anatomy, Biochemistry, and Biotechnology, CRC Press, Taylor & Francis Group, Boca Raton, Fla., USA, which is incorporated herein by reference for media and methods for culturing algae. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (ccap.ac.uk/media/pdfrecipes); and Katedra Botaniky (/botany.natur.cuni.cz/algo/caup-media.html).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Table 2), or a modified medium such as ATCC Medium 854 (BG-11 modified to contain vitamin B12) or ATCC Medium 617 (BG-11 modified for marine cyanobacteria, containing additional NaCl and vitamin B12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation.

In further embodiments where free fatty acids are produced, by using the excess amount of metal (e.g., calcium) in the medium, at least a portion of the fatty acid(s) secreted into the media can be sequestered as soap precipitates, which may result in decreasing the toxic effects of free fatty acid(s). Addition of metal (e.g., calcium) in the medium can additionally or alternatively increase the tolerance of microorganism in media with a relatively high concentration of free fatty acids. Additionally or alternatively, fatty acid-producing strains can advantageously be more robust with excess metal (e.g., calcium) content. Although the excess component is described herein as a metal, it is contemplated that the component can more generally be described as a carboxylate counterion source, for example an soap-forming counterion source, a metal ion source (noted as "metal" herein), a multivalent (i.e., having a valence of +2 or higher) counterion source, a divalent counterion source, or some combination. Other details regarding this metal/carboxylate counterion source are described provisional patent application 61/426,602 filed Dec. 23, 2010, entitled "Culturing a Microorganism in a Medium with an Elevated Level of a Carboxylate Counterion Source".

The culture methods can include inducing expression of a lipase gene or other gene encoding a polypeptide having lipolytic activity for the production of free fatty acids or fatty acid derivatives. Inducing expression can include adding a nutrient or compound to the culture, removing one or more components from the culture medium, increasing or decreasing light and/or temperature, and/or other manipulations that promote expression of the lipase or other gene. Such manipulations can largely depend on the nature of the (heterologous) promoter operably linked to the lipase (or other) gene.

In some embodiments of the present invention, the recombinant microorganisms can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use in food, microorganisms are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Cells can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth. For production of fatty acids, photosynthetic microorganisms can additionally or alternately be cultured in shake flasks, test tubes, vials, microtiter dishes, petri dishes, or the like, or combinations thereof. Further additionally or alternatively, genetically engineered photosynthetic microorganisms may be grown in ponds, canals, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pretreat such sources such that the CO level introduced into the (photo)bioreactor do not constitute a dangerous and/or lethal dose vis-à-vis the growth and/or survival of the microorganisms.

Fatty acids and/or fatty acid derivatives can be recovered from culture by recovery means known to those of ordinary skill in the art, such as by whole culture extraction, for example, using organic solvents. In some cases, recovery of fatty acids or fatty acid derivatives can be enhanced by homogenization of the cells, as provided in the examples herein. When fatty acids are sufficiently released from the microorganisms into the culture medium, the recovery method can be adapted to efficiently recover only the released fatty acids or derivatives thereof, only the fatty acids or fatty acid derivatives produced and stored within the microorganisms, or both the produced and released fatty acids or derivatives thereof.

Free fatty acids or fatty acid derivatives secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids or fatty acid derivatives can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

The amount of the fatty acid or fatty acid derivative produced and/or recovered by the method described herein can advantageously be at least about 5 mg per liter of culture, for example at least about 7 mg per liter of culture, at least about 10 mg per liter of culture, at least about 15 mg per liter of culture, at least about 20 mg per liter of culture, at least about 25 mg per liter of culture, or at least about 50 mg per liter of culture. Although many times the goal can be to produce and/or recover as much fatty acid as possible, in some instances the amount of the fatty acid and/or fatty acid derivative produced and/or recovered by the method described herein can be limited to about 2500 mg or less per liter of culture, for example about 2000 mg or less per liter of culture, about 1500 mg or less per liter of culture, about 1250 mg or less per liter of culture, about 1000 mg or less per liter of culture, about 900 mg or less per liter of culture, or about 800 mg or less per liter of culture.

Some embodiments of the present invention include expressing a non-native gene encoding a polypeptide having lipolytic activity (e.g., a lipase or amidase) in a cell by increasing the gene expression level of the non-native gene and increasing a produced amount of free fatty acids or fatty acid derivatives, compared to a microorganism in which the non-native gene has not been introduced and/or has not been overexpressed. Additionally or alternately, the free fatty acids or fatty acid derivatives produced by the microorganism overexpressing the non-native gene encoding a polypeptide having lipolytic activity can be released into the culture medium. Overexpressing an exogenous gene such as a lipase or amidase gene according to further embodiments can include expressing an exogenous gene in a cell where the exogenous gene was absent initially.

In some embodiments of the methods described herein, the level of a $C_{12+}$ free fatty acid, for example a $C_{12}$-$C_{20}$ free fatty acid or a derivative thereof, such as at least one of a $C_{12}$, $C_{14}$, $C_{16}$, and/or a $C_{18}$ free fatty acid, such as a $C_{16}$ and/or $C_{18}$ free fatty acid or a derivative thereof, can be increased in the culture with respect to a culture of a microorganism of the same strain that does not include the non-native nucleic acid molecule encoding a polypeptide having lipolytic activity. For instance, the introduction of lipase non-native gene that encodes, for example, a lipase or amidase, can increase the yield in free fatty acid or fatty acid derivative production by the recombinant microorganism by at least 50% (e.g., by at least 75%, by at least 100%, by at least 125%, by at least 150%, by at least 175%, by at least 200%, by at least 225%, by at least 250%, by at least 275%, by at least 300%, by at least 325%, by at least 350%, by at least 375%, by at least 400%, by at least 425%, by at least 450%, by at least 475%, by at least 500%, by at least 525%, by at least 550%, by at least 575%, by at least 600%, by at least 625%, by at least 650%, by at least 675%, by at least 700%, by at least 725%, by at least 750%, by at least 775%, by at least 800%, by at least 825%, by at least 850%, by at least 875%, by at least 900%, by at least 925%, by at least 950%, by at least 975%, or by at least 1000%) over a production of fatty acids or fatty acid derivative by a non-recombinant microorganism, and/or a microorganism in which the gene encoding a polypeptide having lipolytic activity has not been overexpressed.

The invention additionally or alternately includes a method of producing a free fatty acid using a recombinant microorganism, in which the free fatty acid is optionally but preferably released into the growth media, comprising culturing a recombinant microorganism that has attenuated expression of a gene encoding an acyl-ACP synthetase and comprises at least one non-native gene encoding a polypeptide having lipolytic activity operably linked to a heterologous promoter, wherein the microorganism produces at least one free fatty acid. In some methods, the microorganism has a disrupted acyl-ACP synthetase gene or acyl-CoA synthetase gene. Additionally or alternately, the non-native gene encoding a polypeptide having lipolytic activity can be operably linked to an inducible promoter. In some embodiments, there can be both an endogenous and an exogenous lipase or amidase gene in the recombinant microorganism. In further embodiments, the microorganism can include, in addition to a non-native gene encoding a polypeptide having lipolytic activity, an exogenous gene encoding an acyl-ACP thioesterase, an acyl-CoA thioesterase, or a 4-hydroxybenzoyl thioesterase, and can optionally further have an attenuated acyl-ACP synthetase gene. When the recombinant microorganism exhibits both (a) an attenuated acyl-ACP synthetase expression and also b) a gene encoding a polypeptide having lipolytic activity, such as a lipase or amidase gene, operably linked to a heterologous promoter, such that the expression of the gene(s) result(s) in the production (and optionally but preferably release) of at least one free fatty acid, at least 80% of the free fatty acid(s) produced (e.g., at least 85%, at least 90%, at least 95%, at least 96%, at least 97%, or at least 98%) can have an acyl chain length of at least 16 carbons and optionally also of no greater than 24 carbons, in some examples, of 16-18 carbons. For example, stearic acid (C18:0) and sodium stearate each have 17 carbons attached to the acyl carbonyl, which is attached to the carboxylate oxygen, which is associated with the hydrogen or sodium, respectively. Thus, both stearic acid and sodium stearate have an "acyl chain length", as defined herein, of 18 carbons.

Additionally or alternately in such embodiments, the combination of the attenuation of the acyl-ACP synthetase gene or acyl-CoA synthetase gene and the expression of the non-native gene encoding a polypeptide having lipolytic activity can produce a yield in free fatty acid or fatty acid derivative production by the recombinant microorganism that is increased by at least 50% (e.g., by at least 75%, by at least 90%, by at least 100%, by at least 110%, by at least 120%, or by at least 125%) over a production of an organism comprising and expressing only the lipase gene or the exogenous gene. Further additionally or alternately in such embodiments, the combination of the attenuation of the acyl-ACP synthetase or acyl-CoA synthetase gene and the expression of the non-native gene encoding a polypeptide having lipolytic activity can produce a yield in free fatty acid production by the recombinant microorganism that is at least 2-fold (e.g., at least 5-fold, at least 10-fold, at least 15-fold, at least 20-fold, at least 25-fold, at least 30-fold, at least 35-fold, at least 40-fold, at least 45-fold, at least 50-fold, at least 60-fold, at least 70-fold, at least 80-fold, at least 90-fold, at least 100-fold, between 2-fold and 500-fold, between 2-fold and 100-fold, between 10-fold and 1000-fold, between 10-fold and 500-fold, and/or between 10-fold and 100-fold) over a production of a non-recombinant microorganism, a microorganism into which a non-native gene has not been introduced, or a microorganism in which a non-native gene has not been overexpressed. To clarify, when comparison are between altered microorganisms and either unaltered microorganisms or less altered microorganisms, it should be understood that the unaltered and/or less altered microorganisms are preferably either (1) an exemplar of the wild-type microorganism on which the genetic alteration(s) was(were) made, or (2) an exemplar of the microorganism on which some, but not all, of the genetic alterations were made, as applicable. However, if neither of those organisms are available, the comparison should then be made to (3) a microorganism having as similar a genome as possible to either (1) or (2), as applicable.

Additionally or alternately, the present invention can include one or more of the following embodiments.

Embodiment 1

A recombinant microorganism comprising a non-native nucleic acid molecule comprising a nucleic acid sequence encoding a polypeptide comprising an amino acid sequence having at least about 55% sequence identity to SEQ ID NO:2, SEQ ID NO:4, SEQ ID NO:6, SEQ ID NO:38, SEQ ID NO:40, or SEQ ID NO:47; wherein the recombinant microorganism produces at least one free fatty acid or at least one fatty acid derivative.

Embodiment 2

The recombinant microorganism of embodiment 1, wherein any of the following are satisfied: the non-native nucleic acid molecule comprises a nucleic acid sequence that encodes the polypeptide of SEQ ID NO:2, SEQ ID NO:4, SEQ ID NO:6, SEQ ID NO:38, SEQ ID NO:40, or SEQ ID NO:47; the nucleic acid molecule comprises a nucleic acid sequence encodes a lipase; the nucleic acid molecule comprises a nucleic acid sequence that encodes a polypeptide that recruits to a pfam that is a member of pfam clan CL0028; the nucleic acid molecule comprises a nucleic acid sequence that encodes a polypeptide that recruits to a protein family selected from the group consisting of Pfam PF01674 (Lipase 2), Pfam PF01764 (Lipase 3), Pfam PF07819 (PGAP1), Pfam PF03583 (LIP), Pfam PF00151 (Lipase), Pfam PF00561 (Ab hydrolase 1), Pfam PF02230 (Ab hydrolase 2), Pfam PF07859 (Ab hydrolase 3), Pfam PF08386 (Ab hydrolase 4), Pfam PF12695 (Ab hydrolase 5), Pfam PF12697 (Ab hydrolase 6), Pfam PF12715 (Ab hydrolase 7), or Pfam PF04083 (Abhydro lipase); the nucleic acid molecule comprises a nucleic acid sequence that encodes an amidase; and/or the nucleic acid molecule comprises a nucleic acid sequence that encodes a polypeptide that recruits to pfam PF01425.

Embodiment 3

The recombinant microorganism of any one of the previous embodiments, wherein one or more of the following are satisfied: the nucleic acid sequence is codon-optimized for expression in the recombinant microorganism; the nucleic acid sequence is operably linked to one or more expression control elements; the nucleic acid sequence is under control of a heterologous and/or inducible promoter, such as a nickel-inducible or an isopropyl β-D-1-thiogalactopyranoside-inducible promoter; the recombinant microorganism is a photosynthetic microorganism such as a microalga; and the recombinant microorganism is a *cyanobacterium*.

Embodiment 4

The recombinant microorganism of embodiment 3, wherein the microalga is a member of a genus selected from a group consisting of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox,* and/or wherein the *cyanobacterium* is selected from a group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.*

Embodiment 5

A recombinant microorganism according to any of the previous claims, wherein said microorganism further comprises at least one endogenous gene whose expression is attenuated and/or disrupted, preferably wherein the endogenous gene comprises or is selected from acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, or a combination thereof.

Embodiment 6

A recombinant microorganism according to any of the previous claims, wherein the microorganism comprises at least one exogenous or non-native gene encoding a thioesterase, wherein the thioesterase is selected from the group consisting of any acyl-ACP thioesterase, an acyl-CoA thioesterase, and a 4-hydroxybenzoyl thioesterase.

Embodiment 7

A recombinant microorganism according to any of the previous claims, wherein the microorganism further includes one or more additional exogenous or non-native genes encoding one or more of an acyl-CoA synthetase, an acyl-CoA reductase, an acyl-ACP reductase, a carboxylic acid reductase, a fatty aldehyde reductase, a fatty aldehyde decarbonylase, a fatty acid decarboxylase, a wax synthase, and an acyltransferase, wherein the microorganism produces at least one fatty acid derivative, preferably wherein the fatty acid derivative is a fatty alcohol, a wax ester, an alkane, or an alkene.

Embodiment 8

A method of producing a free fatty acid or a fatty acid derivative, the method comprising culturing the recombinant microorganism of any of the preceding claims under conditions in which the non-native gene encoding a polypeptide having lipolytic activity is expressed, to produce a free fatty acid or derivative thereof, optionally further including recovering at least one free fatty acid or fatty acid derivative, from the cells, the media, or both.

Embodiment 9

The method of embodiment 8, wherein one or more of the following are satisfied: the expression of the polypeptide encoded by the nucleic acid sequence is induced; the microorganism is cultured phototrophically; the amount of the fatty acid or fatty acid derivative produced is at least about 5 mg per liter of culture; the level of at least one of a $C_{12}$-, $C_{14}$-, $C_{16}$-, and/or $C_{18}$-free fatty acid is increased in the culture with respect to a culture of a microorganism of the same strain not transformed with the non-native nucleic acid molecule; and the microorganism produces and releases into the culture medium at least one free fatty acid.

Embodiment 10

A method of producing a free fatty acid or a fatty acid derivative, comprising culturing a recombinant microorganism comprises at least one non-native gene encoding a polypeptide having lipolytic activity operably linked to a heterologous promoter and at least one exogenous gene encoding a thioesterase, under conditions in which the non-native gene encoding a polypeptide having lipolytic activity and the exogenous gene encoding the thioesterase are expressed to produce a free fatty acid or fatty acid derivative, wherein the thioesterase is preferably selected from the group consisting of an acyl-ACP thioesterase, an acyl-CoA thioesterase, and a 4-hydroxybenzoyl thioesterase.

Embodiment 11

A method of producing a free fatty acid or a fatty acid derivative, according to any of embodiments 8-10, wherein the microorganism has attenuated expression of an endogenous gene encoding an acyl-CoA synthetase, acyl-ACP synthetase, an acyl CoA dehydrogenase, a glycerol-3-phosphate dehydrogenase, acetaldehyde CoA dehydrogenase, a pyruvate dehydrogenase, an acetate kinase, or any combination thereof.

Embodiment 12

The method of any one of the previous embodiments, wherein at least 80% (for example at least 85%, at least 90%, or at least 95%) of the free fatty acid(s) or fatty acid derivative(s) produced have an acyl chain length of at least 16 carbons.

Embodiment 13

The method of any of embodiments 11-12, wherein the combination of attenuation of the acyl-ACP synthetase gene and the expression of the non-native gene encoding a polypeptide having lipolytic activity produces a yield in free fatty acid or fatty acid derivative production by the recombinant microorganism that is increased by at least 50% (for example at least 75% or at least 100%) over a production of an organism comprising and expressing only the at least one exogenous gene encoding a polypeptide having lipolytic activity.

Embodiment 14

The method of any one of embodiments 8-13, wherein the at least one free fatty acid is both produced by the recombinant microorganism and released into the culture medium.

Embodiment 15

A recombinant nucleic acid molecule comprising a nucleic acid sequence that encodes a polypeptide comprising an amino acid sequence having at least 50%, at least 55%, at least 60%, at least 65%, at least 70%, at least 75%, at least 80%, at least 85%, at least 90%, at least 95%, at least 97%, at least 99% or about 100% identity to SEQ ID NO:38, SEQ ID NO:40, or SEQ ID NO:47, optionally wherein the nucleic acid molecule is in a shuttle vector, an integration vector, or an expression vector, and/or optionally wherein the nucleic acid sequence is operably linked to a heterologous promoter, which is optionally an inducible promoter.

Embodiment 16

A recombinant microorganism comprising a nucleic acid molecule according to embodiment 15.

Further additionally or alternately, there can be a method according to any one of the preceding method embodiments, wherein the medium used for culturing the fatty acid-producing organism can include an increased concentration of a saponifying ion source (e.g., an inorganic saponifying ion source, a metal ion source, a multivalent metal ion source, a divalent metal ion source, or some combination thereof, such as sodium, potassium, magnesium, calcium, iron, or combinations thereof, particularly multivalent metals, such as magnesium, calcium, and/or iron), with respect to a standard medium formulation (e.g., standard BG-11 medium) or a modified medium (e.g., ATCC Medium 854 or ATCC Medium 617), which increased concentration can optionally be at least about 0.5 mM (e.g., between about 0.5 mM and about 1 mM, between about 1 mM and about 2 mM, between about 2 mM and about 5 mM, between about 5 mM and about 10 mM, between about 10 mM and about 25 mM, and/or greater than 25 mM) and/or can optionally but preferably be at least 2-fold (e.g., at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold) as compared to said standard/modified medium.

Without further description, it is believed that one of ordinary skill in the art can, using the preceding description and the following illustrative examples, make and utilize the present invention and practice the claimed methods. The following working examples, therefore, specifically point out representative embodiments of the present invention, some preferred, and are not to be construed as limiting in any way the remainder of the disclosure.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and/or alterations can be employed without departing from the scope of the presently disclosed subject matter.

Example 1

Expression of Exogenous Lipase Genes in *E. coli*

Two putative lipase genes annotated in the *Synechocystis* genome, sll1969 and sll0482, and a *Saccharomyces cerevisiae* lipase gene, TGL2, were transformed into *E. coli* to determine their effect on fatty acid production.

The coding sequences of sll1969 (SEQ ID NO:1), sll0482 (SEQ ID NO:3), and TGL2 (SEQ ID NO:5), were amplified from genomic DNA using PCR with primers, SEQ ID NOs: 8-9 for sll1969, SEQ ID NOs:22-23 for sll0482, and SEQ ID NOs:19-20 for TGL2. A trc promoter, trcY (SEQ ID NO:7), was used to drive the expression of the tested genes in *Synechocystis* sp. PCC 6803. The fusion fragments of sll1969, sll0482, or TGL2 operably linked to trcY (trcY::sll1969, trcY::sll0482, or trcY::TGL2) were cloned into integration shuttle vector RS1 or RS2.

The pSGI-TW10 lipase expression construct (SEQ ID NO:18) was cloned by inserting a copy of the *Synechocystis* sp. PCC 6803 sll1969 gene sequence encoding a lipase (Accession BAA17403; GI:1652481) into a RS1 integration shuttle vector. The coding sequence (SEQ ID NO:1) was amplified by primers tw37 (cacactaaggaggaaaaaaaccatgg-tagcagaatttccggacc; SEQ ID NO:8) and tw38 (gtaccatatgcat-gcgagctctcagggcaacggtttagcc; SEQ ID NO:9) from *Synechocystis* sp. PCC 6803 genomic DNA. The RS1 integration vector was restriction digested with NcoI and SacI, and the gene was integrated into the vector using a BPS cloning kit to create construct pSGI-TW10 (SEQ ID NO:18).

The RS1 vector was constructed by inserting the RS1 sequences into pUC118, which enables transformation of *Synechocystis* sp. PCC 6803 via double homologous recombination-mediated integration into the "RS1" site of the chromosome (Williams, *Methods Enzymol.* (1988) 167:766-778). The pUC118 vector was digested with HindIII and EcoRI to remove the multiple cloning site (MCS) sequence, and then blunted with T4 DNA polymerase. The RS1 upstream (RS1-up, SEQ ID NO:32) and downstream (RS1-down, SEQ ID NO:33) fragments were amplified from *Synechocystis* genomic DNA by the following primer pairs: for RS1-up, the primers RS6803-5 (attgctgaagcggaatccctg; SEQ ID NO:10) and RSMCS-3 (catggagatctgagctcgcatgcatatg-gtaccatataaccatcaaagccatagttgg; SEQ ID NO:11) were used, and, for RS1-down, the primers RSMCS-5 (atatgcatgcgagct-cagatc tccatggaattcggtaccggtatggatggcaccgatg; SEQ ID NO:12) and RS6803-3 (tgggggaccattctctggatc; SEQ ID NO:13) were used. The complete RS1 sequence was re-amplified by the end primers, RS6803-5 (SEQ ID NO:10) and RS6803-3 (SEQ ID NO:13), using the RS1-up and RS1-down fragments as the templates. The re-amplified 2-kb RS1 complete sequence was then ligated into the pUC118 backbone to make pSGI-YC02. A DNA fragment carrying the kanamycin resistance gene and the rrnB terminator, 1579-KmR, that was amplified by primers NS2-5MCS (gcatgcgagctcagatctaccag-gttgtccttggcgcag; SEQ ID NO:14) and NS21-3MCS (ccatac-cggtaccgaattcgccacgttactgctcgatgg; SEQ ID NO:15), was inserted between EcoRI and BglII sites on pSGI-YC02. An EcoRI fragment containing the lacIq gene was inserted into the EcoRI site of the pSGI-YC02 RS1 vector, between the RS1-down sequence and the 1579-KmR fragment. The trcY promoter (SEQ ID NO:7) was amplified with the primers 4YC-trcY-5 (actagtcctgaggctgaaatg agctgttgacaattaatcatccg-gctcgtataatgtgtggaattgtgag; SEQ ID NO:16) and 4YC-trcY-3 (ccatggttttttttcctccttactct-caaattgttatccgctcacaattccacacattatacgaccggat; SEQ ID NO:17) and was inserted between SpeI and NcoI sites of the RS1 vector to allow for regulation using this IPTG-inducible promoter. The sll1969 lipase gene expression/integration construct is provided as SEQ ID NO:18 (pSGI-TW10).

The pSGI-TW11 lipase construct was cloned by inserting a copy of the *Saccharomyces cerevisiae* gene sequence encoding TGL2 (Accession NP_010343; GI:6320263) into the RS1 integration shuttle vector described immediately above. The TGL2 coding sequence (SEQ ID NO:5) was amplified by primers tw39 (cacactaaggaggaaaaaaaccat-gaaaaatgataataagc; SEQ ID NO:19) and tw40 (ggtaccatatg-catgcgagctcttaaaatccttttcttgccaag; SEQ ID NO:20) from *Saccharomyces cerevisiae* genomic DNA. The RS1 integration vector was restriction digested with NcoI and SacI, and the gene was integrated into the vector using a BPS cloning kit to create construct TW11. The TGL2 lipase gene expression/integration construct is provided as SEQ ID NO:21 (pSGI-TW11).

The pSGI-TW12 lipase expression construct was cloned by inserting a copy of the *Synechocystis* sp. PCC 6803 sll0482 gene (Accession BAA10581; GI:1001744) coding sequence into a RS2 integration shuttle vector. The coding sequence (SEQ ID NO:3) was amplified by primers tw52 (cacactaag-gaggaaaaaaaccatgccaatggcgctttgg; SEQ ID NO:22) and tw51 (gcttaggcctgcagatatctagatcaaacggcggcgattg; SEQ ID NO:23) from *Synechocystis* sp. PCC 6803 genomic DNA. The RS2 integration vector was restriction digested with NcoI and XbaI, and the gene was integrated into the vector using a BPS cloning kit to create construct pSGI-TW12. The sll0482 gene expression/integration construct is provided as SEQ ID NO:24 (pSGI-TW12).

The RS2 integration shuttle vector was based on a pUC19 backbone that included a bacterial origin of replication for maintenance of the plasmid in *E. coli*. The RS2 vector was constructed to include the "RS2 up" (SEQ ID NO:34) and "RS2 down" (SEQ ID NO:35) sequences from the *Synechocystis* genome for homologous recombination. This vector also included an Omega-Sp cassette providing streptomycin/spectinomycin resistance, and the IPTG-inducible trcY promoter. To create the RS2 expression vector, the RS2 sequence (including both the up and down fragments) was amplified from *Synechocystis* PCC 6803 genomic DNA using primers: RS2-5 (gggccctatttgcccgtattctgccctatcc; SEQ ID NO:25) and RS2-3 (gggcccgactgcctttggtggtattaccgatg; SEQ ID NO:26).

Plasmid pUC19 was digested with HindIII and EcoRI to remove the multiple cloning site (MCS), and then treated with T4-DNA polymerase to blunt the ends. The RS2 sequence (comprising RS2 up and RS2 down; ~1.8 kb) was ligated into the pUC19 backbone. The resulting plasmid was named pYC34. The pYC34 plasmid was then digested with BglII, which cut within the RS2 sequence, opening up the integration site. A copy of the Omega-Sp cassette (BamHI fragment) was ligated into the BglII site of pYC34 to make pYC36. The pYC36 plasmid was digested with FspI to remove the majority of the Ampicillin resistance gene (Apr), making spectinomycin/streptomycin the only selection marker in the plasmid. The constructed plasmid was named pYC37. An EcoRI fragment containing the lacIq gene was inserted into the EcoRI site of pYC37, between the RS2-up sequence and the Omega-Sp cassette to allow for regulation of IPTG-inducible promoters. The vector further included a trcY promoter. The trcY promoter (SEQ ID NO:7) was amplified as for the RS1 integration vector, using the 4YC-trcY-5 (SEQ ID NO:16) and 4YC-trcY-3 (SEQ ID NO:17) primers. The PCR amplified trcY promoter sequence (SEQ ID NO:7) was inserted between the SpeI and Nod sites on the RS2 vector.

Each of the plasmids containing sll1969, sll0482, or TGL2, and the control vector was introduced into *E. coli* K27 cells (the K27 strain is a FadD mutant deficient in acyl-CoA synthetase activity: Overath (1969) *Eur J Biochem* 7:559-574; Schneider et al. (1998) *Appl and Environ Microbiol* 64: 3784-3790; Greenway and Silbert (1983) *J Biol Chem* 258: 13034-13042) using standard methods.

To test for the effect of expression of the lipase genes on the cells, the transformed *E. coli* cells were grown for about 24 hours in medium to which IPTG was added to a final concentration of 1 mM. Three replicates of each transformed gene were grown. At the end of the growth period, about 0.6 ml of each culture was transferred to a ~2 mL glass GC vial with a PTFE-lined caps (National Scientific) for analysis. The culture sample included medium and cells cultured within the medium.

Free fatty acids were analyzed by gas chromatography with flame ionization detection (GC-FID). About fifty microliters of an internal standard (I.S.) set that included the free fatty acids C9:0, C13:0, and C17:0, each at approximately 600 µg/ml in hexane, were added to each culture sample followed by about 50 microliters of ~50% $H_2SO_4$, about 100 microliters of ~5M NaCl, and about 850 microliters of hexane. The final concentration of each I.S. was ~50 µg/mL. The fatty acids for making the internal standard set were purchased either from Fluka or Nu Chek Prep. The cultures were then vortexed on a Multi-tube vortexer at about 2,500 rpm for about 30 minutes. The vials were finally centrifuged for about 3 minutes at about 2500 rpm in order to provide good separation between organic and aqueous phases. The hexane layer was sampled by a Gerstel MPS2L Autosampler.

*E. coli* fatty acid samples were analyzed on an Agilent model 7890A gas chromatograph equipped with an FID (flame ionization detector) that included a J&W Scientific DB-FFAP capillary column (~15 m length, ~0.25 mm internal diameter, ~0.25 µm film thickness). The GC oven was programmed as follows: about 140° C. for about 0.5 min., then heated at ~20° C./min. to about 230° C. (hold about 5 mins.). The injector temperature was kept at about 250° C., and a ~40:1 split ~1.0 µl injection was used. Helium was used as a carrier gas at a flow rate of about 1.2 mL/min. The analytes were identified by comparison of retention times to individually injected standards. The calibration range for the analytes was about 2 µg/ml to about 200 µg/ml for C8:0-C16:1 fatty acids and about 0.5 µg/ml to about 50 µg/ml for C18:0-C18:2 fatty acids. Spiking and recovery experiments into whole cell culture shows that the extraction method recovers consistently within a range of about 85-115% of each analyte. The free fatty acid assays of *E. coli* strains indicated all three lipase were functional (Table 1) and led to the production of free fatty acids by the microbial host.

TABLE 1

| Fatty acid assay results for *E. coli* K27 strain samples | | |
|---|---|---|
| Strain | FFA Production (mg/L) | (mg/L/OD) |
| TrcY-sll0482 (pTW012) | 19.3 | 8.3 |
| TrcY-sll1969 (pTW10) | 18.7 | 4.5 |
| TrcY-TGL2 (pTW11) | 24.4 | 9.2 |
| K27 (control) | 7.2 | 1.9 |

Example 2

Overexpression of Lipase in AAS Knockout (AAS-KO) Strains

The same constructs used in Example 1 were transformed into *Synechocystis* sp. PCC 6803 cells that were genetically manipulated to disrupt (knock-out) the acyl-ACP synthetase (AAS) gene by insertion of chloramphenicol acyl transferase (cat) gene into the AAS gene.

To make the AAS knock-out host strain, a ~1.7-kbp DNA fragment spanning an area upstream and into the coding region of the acyl-ACP synthetase-encoding gene, slr1609 (Cyanobase gene designation), from *Synechocystis* sp. PCC 6803 was amplified from genomic DNA using PCR with primers NB001 (SEQ ID NO:27) and NB002 (SEQ ID NO:28). This fragment was cloned into the pCR2.1 vector (Invitrogen) to yield plasmid pSGI-NB3 and was subsequently cut with the restriction enzyme Mfel. A chloramphenicol resistance marker cassette containing the cat gene and associated regulatory control sequences was amplified from plasmid pAM1573 (Andersson (2000) *Methods Enzymol.* 305:527-542) to contain flanking Mfel restriction sites using PCR with primers NB010 (SEQ ID NO:29) and NB011 (SEQ ID NO:30). The cat gene expression cassette was then inserted into the Mfel site of pSGI-NB3 to yield pSGI-NB5 (SEQ ID NO:31).

The pSGI-NB5 construct was transformed into the *Synechocystis* sp. PCC6803 strain according to Zang et al. (2007) *J. Microbiology*, 45:241-245. Insertion of the chloramphenicol resistance marker into the Slr1609 gene through homologous recombination was verified by PCR screening of insert and insertion site.

The resulting knock-out strain was independently transformed with each of the lipase expression constructs of Example 1: pSGI-TW10 (SEQ ID NO:18, trcY::sll1969); pSGI-TW12 (SEQ ID NO:24, trcY::sll0482), and pSGI-TW11 (SEQ ID NO:21, trcY::TGL2), essentially according to Zang et al. (2007) and antibiotic resistant colonies were selected and screened for the presence of the specific lipase gene by PCR. The isolates were then tested for fatty acid production.

The recombinant microorganisms were cultured in ~1 ml standard BG-11 medium (ATCC 616, as shown in Table 2; component weights are approximate; final pH 7.1; autoclaved at about 121° C. for about 15 mins.) in ~4 ml screw thread glass vials with gas permeable tape for sealing, growing at about 30° C., ~65 µmol/m²/s light, about 215 rpm with the supply of ~5% $CO_2$. The BG-11 medium does not provide a reduced carbon source that can be used as an energy source for the growth of the cells. Rather, the cells were grown phototrophically using $CO_2$ as substantially the sole carbon source, using light as the energy sources, and incorporating carbon from $CO_2$ into biomolecules, including fatty acids. The final concentration of ~1 mM IPTG was added where appropriate to induce the free fatty acid production. The whole vials were submitted for GC-free fatty acid analysis after about 7 days of IPTG induction.

Specifically, the recombinant microorganisms were cultured and ~1 mM IPTG was added as described above. After approximately seven days of induction, samples taken from the culture were processed for GC/FID analysis.

TABLE 2

| ATCC 616 Medium BG-11 | | |
|---|---|---|
| $NaNO_3$ | 1.5 g | |
| $K_2HPO_4$ | 0.04 g | |
| $MgSO_4 * 7H_2O$ | 0.075 g | |
| $CaCl_2 * 2H_2O$ | 0.036 g | |
| Citric acid | 6.0 mg | |
| Ferric ammonium citrate | 6.0 mg | |
| EDTA | 1.0 mg | |
| $Na_2CO_3$ | 0.02 g | |
| Trace Metal Mix A5# | 1.0 ml | |
| Agar (if needed) | (up to) 10.0 g | |
| Distilled water | 1.0 L | |
| #Trace Metal Mix A5 | $H_3BO_3$ | 2.86 g |
| | $MnCl_2 * 4H_2O$ | 1.81 g |
| | $ZnSO_4 * 7H_2O$ | 0.22 g |
| | $Na_2MoO_4 * 2H_2O$ | 0.39 g |
| | $CuSO_4 * 5H_2O$ | 0.080 g |
| | $Co(NO_3)_2 * 6H_2O$ | 49.4 mg |
| | Distilled water | to 1.0 L |

Free fatty acids were analyzed by gas chromatography with flame ion detection (GC-FID). About 1.0 mL of the *Synechocystis* cultures were added to ~2 mL glass GC vials with PTFE-lined caps (National Scientific). About eighty-four microliters of an internal standard (I.S.) set that included the free fatty acids C9:0, C13:0, and C17:0, each at about 600 µg/ml in hexane, were added to the culture sample followed by about 83 microliters of ~50% $H_2SO_4$, about 167 microliters of ~5M NaCl, and about 1.4 milliliters of hexane. The final concentration of each I.S. was about 50 µg/mL. The fatty acids for making the internal standard set were purchased either from Fluka or Nu Chek Prep. The cultures were then vortexed on a Multi-tube vortexer at about 2,500 rpm for about 30 minutes. The vials were finally centrifuged for about 3 minutes at about 2,500 rpm, in order to provide good separation between organic and aqueous phases. The hexane layer was sampled directly, without separation from the aqueous layer, by a Gerstel MPS2L Autosampler.

*Synechocystis* fatty acid samples were analyzed on an Agilent model 7890A GC/FID that included a J&W Scientific DB-FFAP capillary column (~15 m length, ~0.25 mm internal diameter, ~0.25 µm film thickness). For analysis of cyanobacterial samples, the GC oven was programmed as follows: about 170° C. for about 0.5 minutes, then heated at about 30° C./minute to about 230° C. (hold ~5 minutes). The injector temperature was kept at about 250° C., and a ~40:1 split ~1.0 µl injection was used. Helium was used as a carrier gas at a flow rate of about 1.2 mL/minute. The analytes were identified by comparison of retention times to individually injected standards. The calibration range for the analytes was about 2 µg/ml to about 200 µg/ml for C8:0-C16:1 fatty acids and about 0.5 µg/ml to about 50 µg/ml for C18:0-C18:2 fatty acids. Spiking and recovery experiments into whole cell culture shows that the extraction method recovers consistently within a range of about 85-115% of each analyte.

TABLE 3

Free fatty acid assay results for *Synechocystis* sp. PCC 6803 WT and AAS-KO strain samples using overexpression construct of sll1969, sll0482, or TGL2 lipase genes (Avg 9 isolates).

| Strain | Construct | FFA Production (mg/L) |
|---|---|---|
| pTW10/WT | TrcY-sll1969 | 6.9 |
| pTW011/WT | TrcY-TGL2 | 24.4 |
| pTW10/CNB8 | sll1969/AAS-KO | 22.7 |
| pTW11/CNB8 | TGL2/AAS-KO | 53.6 |
| pTW12/CNB8 | sll0482/AAS-KO | 11.3 |
| WT (control) | — | 1.1 |

As shown in Tables 3 and 4, the three lipase genes were also active in *Synechocystis*, and also led to the production of free fatty acids by the recombinant hosts. Disruption of the recycling of free acids in the AAS-KO background further enhanced free fatty acids production when lipase genes were overexpressed.

The data showed that production of substantial amount of free fatty acids were observed in sll1969 and TGL2 strains, which was further enhanced by 2 to 3 times in the AAS-KO background (Table 3). Lower quantities of free fatty acids were also detected in sll0482/AAS-KO strains. The sll0482, sll1969, and TGL2 strains all have roughly similar free fatty acid profiles, as expected for free fatty acid released by lipases, as shown in Table 4.

TABLE 4

Free fatty acids as a percentage of total free fatty acids produced by *Synechocystis* strains

| Construct | C12:0 | C14:0 | C16:0 | C16:1 | C18:0 | C18:1cis9 | C18:2cis9,12 | C18:3cis6,9,12 | $FFA_{TOT}$ mg/L |
|---|---|---|---|---|---|---|---|---|---|
| TrcY-sll0482/AAS-KO | 0.11 | 0.00 | 29.62 | 4.00 | 48.30 | 2.79 | 14.55 | 0.06 | 11.27 |
| TrcY-sll1969 | 0.00 | 0.00 | 36.74 | 1.27 | 53.13 | 0.00 | 8.66 | 0.20 | 6.88 |
| TrcY-sll1969/AAS-KO | 0.78 | 1.93 | 35.74 | 5.54 | 28.95 | 6.38 | 18.22 | 0.39 | 22.71 |
| TrcY-TGL2 | 0.00 | 0.46 | 33.74 | 3.58 | 24.79 | 18.19 | 19.01 | 0.13 | 24.40 |
| TrcY-1 TGL2/AAS-KO | 1.20 | 2.50 | 34.13 | 9.55 | 17.42 | 11.21 | 20.22 | 1.24 | 53.58 |

Example 3

In Vivo Assay for Novel Genes Encoding Lipolytic Enzymes

This example describes isolation of novel genes encoding polypeptides having lipolytic activity from a metagenomic library and expression of the novel genes in *Synechocystis*, resulting in free fatty acid production.

A metagenomic library from an environmental sample isolated from a shipping channel in Brownsville, Tex. was generated by using a Millipore Stainless Steel filtration train to successively filter the water sample through 20 μm, 3 μm, 0.8 μm, and 0.1 μm filters. A section of the final 0.1 μm filter was then added to Luria broth and the sample was cultured with shaking at 225 rpm at about 30° C. overnight. Cells were then collected by centrifugation (approximately 4,000×g for 10 min) after which the cell pellets were resuspended in a lysis buffer that included 50 mM Tris-Cl, pH ~8.0 (containing 10 mM EDTA, 100 μg/ml RNase A, 4 mg/ml Lysozyme, 100 μg/ml Lysostaphin, and 500 U/ml Mutanolysin), and incubated at ~37° C. with agitation (~100 rpm). The homogenates were then sedimented by centrifugation for about 30 min at ~16,000 g at ~4° C. The supernatants were transferred to new tubes and mixed with an equal volume of cold (about ~20° C.) 100% ethanol to precipitate the DNA. The precipitate was collected by centrifugation at ~16,000 g at ~4° C. or spooled onto a sterile disposable inoculation loop. The DNA was washed then in ~75% ethanol and dried at room temperature and resuspended in ~50 mM Tris-Cl, pH ~8.0, for fractionation and library construction.

The isolated metagenomic DNAs from the amplified metagenomic sample was partially digested with restriction endonuclease Sau3AI, size fractionated using gel electrophoresis or a sizing column for fragments in the range of 3-5 kb, or in some cases, 3-12 kb, and ligated into the BamHI site *E. Coli* expression vector pUK (Accession L31614; GI:508605; Huang et al. (1994) *Gene* 151: 143-145). The pUK vector includes the tac promoter for IPTG-inducible expression upstream of the multiple cloning site.

The metagenomic library was transformed into competent *E. coli* K12 cells, and ampicillin-resistant colonies were screened for clearing of the agar surrounding the colonies on a tributyrate plate assay.

A plate-based assay was used to identify recombinant *E. coli* colonies producing polypeptides having lipolytic activity by detecting hydrolysis of the emulsified glycerin tributyrate substrate (Sigma Aldrich, St. Louis, Mo.) present at a concentration of 1% in LB agarose media. Colonies displaying a surrounding "halo" of clear agar were selected and grown up, the plasmid DNAs of the halo-producing clones were isolated, and the library inserts were sequenced and analyzed.

The metagenome fragments ("contigs") of clones that produced clearing zones were examined for open reading frames (ORFs). Several of the contigs included ORFs encoding polypeptides having homology to domains identified as characteristic of lipases, esterases, or amidases. The ORFs were subcloned into the *Synechocystis* integration/expression vector YC63 (used to make construct pSGI-TW12 described in Example 2) that includes "RS2 up" (SEQ ID NO:34) and "RS2 down" (SEQ ID NO:35) sequences for integration into the *Synechocystis* genome. The ORF expression constructs were transformed into the cyanobacterium *Synechocystis* sp. PCC 6803. The YC63 vector (SEQ ID NO:36) includes the TrcY promoter (SEQ ID NO:7) which directs IPTG-inducible expression of the transgenes in *Synechocystis*, and the lacIq gene for regulation of the TrcY promoter. The YC63 vector also includes the aadA (spectinomycin acyltransferase) gene for selection of transformants on streptomycin or spectinomycin.

Constructs contained nucleic acid sequences that included the metagenomic library ORFS designated BSC1-5 (SEQ ID NO:37) and BSC-13 (SEQ ID NO:39). The amino acid sequences encoded by the BSC1-5 and BSC-13 ORFS were determined as SEQ ID NO:38 and SEQ ID NO:40, respectively.

The polypeptide encoded by the BSC1-5 ORF (SEQ ID NO:37), or amino acid sequence SEQ ID NO:38, recruits to pfam PF12695, the Ab (alpha/beta) hydrolase 5 family (gathering cutoff 27.0) with a bit score of 30.9 and an e-value of 1.6 e-07. The BSC1-5 lipase has 54% amino acid sequence identity to LipIAF1-6 (NCBI accession ADI78874; GI:298362845), a lipase of an uncultured microorganism described in Cote and Shareck (2010) *J. Ind. Microbiol. Biotechnol.* 37 (9), 883-891.

The polypeptide encoded by the BSC-13 ORF (SEQ ID NO:39), or amino acid sequence SEQ ID NO:40, recruits to Pfam PF01425, the Amidase family (gathering cutoff 20.1) with a bit score of 353.1 and an e-value of 1.7 e-105. The BSC-13 amidase ORF demonstrating lipolytic activity has 84% amino acid sequence identity to an amidase signature enzyme of *Marinobacter adhaerens* HP15 (NCBI accession ADP98107; GI:311695234). It also demonstrates 75% amino acid sequence identity with an amidase of *Marinobacter algicola* DG893.1 (NCBI accession ZP_01895774; GI:149378051); 47% amino acid sequence identity with an amidase of gamma proteobacterium HdN1 (NCBI accession YP_003810088; GI:304310490); 43% amino acid sequence identity with an enantiomer selective amidase of *Streptomyces* sp. R1128 (NCBI accession AAG30199 GI:11096124); 41% amino acid sequence identity with an amidase of *Parvibaculum lavamentivorans* DS-1 (NCBI accession YP_001412078 GI:154251254); 40% amino acid sequence identity with an amidase of marine gamma proteobacterium HTCC2080 (NCBI accession ZP_01627249; GI:119505174); 40% amino acid sequence identity with a glutamyl-tRNA (Gln) amidotransferase subunit A of gamma proteobacterium NOR5-3 (NCBI accession ZP_05128598; GI:254516539); 40% amino acid sequence identity with an amidase family protein of gamma proteobacterium IMCC3088 (NCBI accession ZP_08271536; GI:329896458); and 40% amino acid sequence identity with a putative amidase of *Bradyrhizobium* sp. BTAi1 (NCBI accession YP_001241134; GI:148256549).

In addition to the BSC ORFs encoding polypeptides identified as having lipolytic activity by the functional expression screen, a variant of the Lipase B gene from *Candida antarctica* lipase B (NCBI accession P413365; GI:1170790) was also cloned into the YC63 expression vector to test its activity in *Synechocystis*. The CalB ORF (SEQ ID NO:41) encoded a lipase B polypeptide (SEQ ID NO:42) identical in sequence to the wild-type *C. antarctica* (NCBI accession P413365; GI:1170790) except that the encoded polypepyide was truncated by 18 amino acids at the N terminus with respect to the native *C. antarctica* gene. This lipase, well known for industrial uses (e.g., U.S. Pat. Nos. 5,928,933, 6,255,451, 6,486,295, 7,455,998, 6,365,398, 6,642,035, and 7,205,373), recruits to pfam PGAP1 (PF07819) "PGAP1-like protein, gathering cut-off, 20.5) with a bit score of 13.1, and an e value of 0.043.

The *Synechocystis* expression vectors including nucleic acid sequences encoding the CalB polypeptide (SEQ ID NO:42), the BSC1-5 polypeptide (SEQ ID NO:38), and BSC-13 polypeptide (SEQ ID NO:40), were each transformed into a *Synechocystis* PCC 6803 strain (under the control of the TrcY promoter (SEQ ID NO:7)). In addition, the *Cuphea*

*carthagenensis* Cc1FatB1 gene (SEQ ID NO:43) encoding an N-terminally truncated acyl-ACP thioesterase (SEQ ID NO:44, US2011/020883) was cloned into *Synechocystis* integration vector YC63 (SEQ ID NO:36) as a control for the production of fatty acids by an engineered cyanobacterial strain.

To introduce the Cc1 FatB1 acyl-ACP thioesterase gene construct and the BSC ORF constructs into cyanobacteria, *Synechocystis* sp. PCC 6803 cells were cultured in BG-11 media to an OD (730 nm) of about 0.7-0.9. About 10 mL of the culture was spun down at approximately 2000 g for 15 minutes, then the cell pellet was resuspended in 1 mL fresh BG-11 media. An aliquot of 300 µL of cells was transformed with about 100 ng of integration vector. The cells were incubated under lights (80 µE) for about 6 hours, then spread onto Minipore filters and placed on top of BG-11 agar plates containing no antibiotics. The plates were incubated at about 30° C. under about 80 µE of light for about 24 hours. The filters were then transferred onto fresh BG-11 1.5% agar plates with 20 µg/mL spectinomycin and cultured for 7 days. Colonies of *Synechocystis* sp. PCC 6803 were picked and patched onto new agar plates.

Transformants were inoculated from starter cultures to provide cyanobacterial cultures having an initial OD (730 nm) of 0.6 and a culture volume of 1.5 mL in 4 mL glass vials. The culture medium was BG11, which does not include a substantial amount of a reduced carbon source, to which IPTG was added to a final concentration of 1 mM for inducing expression of the transgenes. The cultures were grown under constant light at about 60 uE shaking in the presence of 1% $CO_2$ for 6 days. The entire culture was submitted for fatty acid analysis, with approximately 1 mL of culture remaining in the vials due to evaporation during the culture period. Free fatty acids were analyzed by gas chromatography (GC) with flame ionization detection (GC-FID) essentially as described in Example 2.

The total free fatty acids produced by these engineered *Synechocystis* strains is provided in Table 5. Each result shown in Table 5 is the average of three cultures of the same strain. BSC1-5 Y63 #1 and BSC1-5 Y63 #2 are two independent transformants having the BSC1-5 Y63 construct. The results demonstrated that the BSC1-5 and BSC-13 genes encoded polypeptides with lipolytic activity in *Synechocystis* that resulted in the production of free fatty acids (FFAs). The *Synechocystis* strain expressing the Cc1FatB1 thioesterase (SEQ ID NO:44) also produced free fatty acids, as demonstrated previously. The data also demonstrate that expression of the novel polypeptide encoded by the BSC1-5 ORF (SEQ ID NO:38) and, most surprisingly, expression of the novel polypeptide encoded by the BSC-13 ORF (SEQ ID NO:40) that is identified by sequence analysis as an amidase, result in the production of free fatty acids be the engineered host strains. In contrast, the engineered *Synechocystis* strain expressing Lipase B of *C. antarctica* (SEQ ID NO:42) produced a negligible amount of free fatty acids.

TABLE 5

Free Fatty Acid Production by *Synechocystis* Strains Expressing Novel Lipases

| Strain | FFA mg/L | FFA mg/L/OD |
| --- | --- | --- |
| CaLipB Y63 #1 | 0.6 | 0.1 |
| CaLipB Y63 #3 | 0.6 | 0.1 |
| BSC1-5 Y63 #1 | 159.2 | 17.8 |
| BSC1-5 Y63 #2 | 129.6 | 16.5 |
| BSC-13 Y63 #1 | 94.6 | 13.9 |
| Cc1FatB1 YC63 | 385.9 | 86.2 |

The chain lengths of the fatty acids produced by the engineered strains were also analyzed. The results are provided in Table 6.

TABLE 6

FFA chain lengths of engineered *Synechocysits* strains (mg/L).

| Strain | C12:0 | C14:0 | C16:0 | C16:1cis9 | C18:0 | C18:1cis9 | C18:1cis11 | C18:2cis9,12 | C18:3cis6,9,12 |
| --- | --- | --- | --- | --- | --- | --- | --- | --- | --- |
| CaLipB Y63 #1 | 0.0 | 0.0 | 0.6 | 0.0 | 0.0 | 0.0 | 0.0 | 0.0 | 0.0 |
| CaLipB Y63 #3 | 0.0 | 0.0 | 0.6 | 0.0 | 0.0 | 0.0 | 0.0 | 0.0 | 0.0 |
| BSC1-5 Y63 #1 | 3.7 | 8.2 | 71.1 | 9.1 | 9.4 | 22.7 | 6.1 | 18.1 | 7.4 |
| BSC1-5 Y63 #2 | 2.6 | 5.1 | 63.5 | 4.1 | 9.2 | 18.7 | 3.9 | 12.9 | 6.7 |
| BSC-13 Y63 #1 | 0.2 | 0.9 | 39.1 | 0.0 | 46.1 | 5.5 | 0.0 | 1.9 | 0.8 |
| Cc1FatB1 YC63 | 41.4 | 129.9 | 194.2 | 0.0 | 16.4 | 4.0 | 0.0 | 0.0 | 0.0 |

As expected from previous characterization (US20110/020883; WO2011/008565), expression of the Cc1FatB1 acyl-ACP thioesterase resulted in production of predominantly C16 and C14 free fatty acids, along with some C12 free fatty acids, and a proportionately much smaller amount of C18 free fatty acids (bottom row of Table 6). The BSC1-5 strains, on the other hand, predominantly produced C16 and C18 free fatty acids, with much smaller amount of C14 and C12 free fatty acids being produced. The BSC-13 carrying strain also produced predominantly C18 and C16 free fatty acids, with almost no C12 and C14 free fatty acids produced.

In addition, the *Cuphea carthagenensis* Cc1FatB1 acyl-ACP thioesterase gene (SEQ ID NO:43, US2011/020883) was cloned into *Synechocystis* integration vector YC28, which included a PI5A origin of replication for *E. coli*, "RS1 up" (SEQ ID NO:32) and "RS1 down" (SEQ ID NO:33) fragments for homologous recombination in *Synechocystis* 6803, a lacIQ repressor, a TrcE promoter (SEQ ID NO:45) for driving expression of the Cc1FatB1 thioesterase gene and a kanamycin resistance marker for selection. The Cc1FatB1 YC28 construct was transformed into the *Synechocystis* strain that included the YC63 RS1 integration/expression vector that included the BSC-13 ORF essentially as described in Example 3, except that colonies were selected for the presence of both constructs using both spectinomycin and kanamycin (20 µg/ml each). A strain having both the BSC13 lipase ORF expression construct and the Cc1FatB1 acyl-ACP thioesterase expression construct were cultured and analyzed for fatty acid production as provided above for the BSC-ORF-expressing strains. The results of co-expression of the non-native lipase gene and a non-native acyl-ACP thioesterase gene are provided in Table 7, which demonstrates that the cells produced a greater amount of free fatty acid when both genes were expressed than when only the lipase gene was expressed.

TABLE 7

Free fatty acid production by strains expressing BSC-13 alone and in combination with an acyl-ACP thioesterase.

| Strain | mg/L FFA | mg/L/OD FFA |
|---|---|---|
| BSC-13 Y63 #1 | 97.3 | 14.3 |
| BSC-13 Y63 #1, Cc1FatB1 YC28 #1 | 325.3 | 46.8 |

Analysis of the free fatty acid species produced by the co-expressing cells shown in Table 8 demonstrates that the non-native lipase was active in the cells that also expressed a non-native thioesterase, as production of C18 free fatty acids was proportionally greater in the lipase plus thioesterase strain than in the cells that express only the thioesterase (Table 7).

TABLE 8

FFA chain lengths of engineered *Synechocysits* strains expressing polypeptides having lipolytic activity.

| Strain | C12:0 | C14:0 | C16:0 | C18:0 | C18:1cis9 | C18:2cis9,12 |
|---|---|---|---|---|---|---|
| BSC-13 Y63 #1 | 0.2 | 0.9 | 39.1 | 46.1 | 5.5 | 5.5 |
| BSC-13 Y63 #1, Cc1FatB1 YC28 | 14.9 | 74.3 | 183.3 | 31.4 | 11.0 | 10.4 |

Example 4

Isolation of a Novel Gene from Multistrain Library Encoding a Polypeptide Having Lipolytic Activity A multi-strain bacterial library was generated by growing 489 independent bacterial strains, most of which were identified by BLAST searching of ribosomal DNA as being of the genus *Pseudomonas* or related to *Pseudomonas* species. The bacterial isolates were grown individually in 1 ml of 2×YT media (Teknova) in deep 96 well plates at 30C shaking at 225 rpm for two days. Following the growth period, wells were pooled and gDNA was extracted, partially digested with Sau3A, and size fractionated as in Example 3. The resulting genomic fragments were cloned in the pUK expression vector of Example 3 and transformed into *E. coli* cells that were screened for lipolytic activity in the tributyrate plate assay as in Example 3. One of the clones identified in the assay as including an ORF that encoded a polypeptide having lipolytic activity was designated P500114. The fragment was sequenced and found to include an ORF (SEQ ID NO:46).

The amino acid sequence encoded by the P500114 ORF (SEQ ID NO:46), or SEQ ID NO:47, was found to recruit to pfam PF07859, the Ab (alpha/beta) hydrolase 3 family (gathering cutoff 20.7) with a bit score of 230.6 and an e-value of 1.2 e-68. The P500114 polypeptide has 50% amino acid sequence identity to lipH of *Burkholderia thailandensis* TXDOH (NCBI accession ZP_02371858; GI:167578984); 50% amino acid sequence identity to a lipase/esterase of *Acaryochloris marina* MBIC11017 (NCBI accession YP_001514890; GI:158333718); 49% amino acid sequence identity to a hypothetical protein BthaA_17529 of *Burkholderia thailandensis* E264 (ZP_05589243; GI:257140981); 49% amino acid sequence identity to LipH of *Burkholderia thailandensis* E264 (ABC34438; GI:83650374); 49% amino acid sequence identity to a lipolytic enzyme of an uncultured bacterium (Hu et al. (2010) *FEMS Microbiol E. coli* 7: 228-237) (ACL67843.1 GI:219957624); and 44% amino acid sequence identity to a lipase/esterase of *Candidatus Chloracidobacterium thermophilum* B (YP_004862114; GI:347754550).

The P500114 ORF was cloned into the YC63 vector (SEQ ID NO:36) having RS2 up (SEQ ID NO:34) and RS2 down (SEQ ID NO:35) sequences for recombination into the *Synechocystis* genome, a spectinomycin resistance marker, and the IPTG-inducible TrcY promoter (SEQ ID NO:7) for driving expression of the transgene. The P500114 ORF YC63 expression construct was transformed into *Synechocystis* cells using the procedures detailed in Example 3.

The *Cuphea carthagenensis* Cc1FatB1 acyl-ACP thioesterase gene expression construct of Example 3, above, was also used to transform the P500114 YC63 expression construct-carrying *Synechocystis* strain as provided in Example 3 to obtain transformants that included both the BSC-13 expression construct and the Cc1FatB1 expression construct. Strains transformed with either the P500114 ORF YC63 expression construct, or the P500114 ORF YC63 expression construct and the Cc1FatB1 YC28 expression construct were cultured and analyzed for fatty acid essentially as provided in Example 3.

The results, provided in Table 9, demonstrate that expression of the P500114 gene does result in the production of free fatty acids by the photosynthetic microorganisms, and that greater amounts of free fatty acids are produced when an acyl-ACP thioesterase is expressed along with the P500114 lipase.

TABLE 9

Free fatty acid production by strains expressing a lipase from multistrain library

| Strain | mg/L FFA | mg/L/OD FFA |
|---|---|---|
| p500114-1-4 YC63 − 1 | 49.7 | 6.8 |
| p500114-1-2 YC63 + YC28 ccFatB1-1 | 67.2 | 8.3 |
| p500114-2-7 YC63 + YC28 ccFatB1-1 | 254.4 | 51.22 |

The free fatty acid profile of the P500114 ORF-expressing strain, and the free fatty acid profiles of strains expressing the P500114 ORF in combination with an exogenous acyl-ACP thioesterase gene shows that while expression of P500114 ORF results predominantly in the production of C16 fatty acids, with a lesser amount of C18 free fatty acids generated, expression of the Cc1FatB1 acyl-ACP thioesterase boosts free fatty acid production, and particularly production of free fatty acids with chain lengths less than 18 carbons, while production of C18 free fatty acids remains at least as high as in strains that express only the p500114 lipase.

TABLE 10

Free fatty acid profile of strains expressing the p500114 ORF and the p500114 ORF plus an acyl-ACP thioesterase

| Strain | C12:0 | C14:0 | C16:0 | C16:1cis9 | C18:0 | C18:1cis9 | C18:2cis9,12 | C18:3cis6,9,12 |
|---|---|---|---|---|---|---|---|---|
| P500114 Y63 | 0.4 | 2.3 | 32.3 | 0.0 | 11.9 | 0.0 | 0.0 | 2.8 |
| P500114 Y63-1 CclFatB1 YC28 | 0.6 | 4.1 | 45.0 | 0.0 | 12.4 | 0.0 | 0.0 | 5.1 |
| P500114 Y63-2 CclFatB1 YC28 | 15.1 | 61.6 | 140.2 | 2.2 | 21.0 | 3.6 | 5.1 | 5.7 |

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entireties.

What is claimed is:

1. A recombinant microorganism comprising a non-native nucleic acid molecules encoding a polypeptide having lipolytic activity, wherein the polypeptide comprises an amino acid sequence having at least 90% amino acid sequence identity to the amino acid sequence of SEQ ID NO:40, and wherein the recombinant microorganism has attenuated expression of
    at least one endogenous gene selected from the group consisting of an acyl-CoA synthetase gene and an acyl-ACP synthetase gene as compared to a corresponding wild-type microorganism, and wherein
    the recombinant microorganism produces at least one free fatty acid or at least one fatty acid derivative.

2. The recombinant microorganism of claim 1, wherein the recombinant microorganism further comprises at least one non-native nucleic acid molecule that encodes an acyl-ACP thioesterase, an acyl-CoA thioesterase, or a 4-hydroxybenzoyl thioesterase.

3. The recombinant microorganism of claim 1, wherein the recombinant microorganism is a microalga.

4. The recombinant microorganism of claim 3, wherein the microalga is selected from the group consisting of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox*.

5. The recombinant microorganism of claim 1, wherein said recombinant microorganism is a cyanobacterium.

6. The recombinant microorganism of claim 5, wherein the cyanobacterium is selected from the group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus*.

7. The recombinant microorganism of claim 1, wherein the endogenous gene encodes an acyl-ACP synthetase.

8. A method of producing a free fatty acid or a fatty acid derivative, the method comprising culturing the recombinant microorganism of claim 1 under conditions in which the non-native nucleic acid sequence is expressed to produce at least one free fatty acid or at least one fatty acid derivative.

9. The method of claim 8, wherein the expression of the non-native nucleic acid molecule encoding the polypeptide having lipolytic activity is induced.

10. The method of claim 8, wherein the microorganism is cultured phototrophically.

11. The method of claim 8, wherein the method further comprises recovering at least one free fatty acid or at least one fatty acid derivative from the cells, the culture medium, or a combination thereof.

12. The method of claim 11, wherein the amount of the fatty acid or fatty acid derivative recovered is at least 5 mg per liter of culture.

13. A method of producing a free fatty acid or a fatty acid derivative, the method comprising culturing the recombinant microorganism of claim 2 and recovering at least one free fatty acid or at least one fatty acid derivative from the culture.

14. A method of producing a free fatty acid or a fatty acid derivative, the method comprising culturing the recombinant microorganism of claim 7 and recovering at least one free fatty acid or at least one fatty acid derivative from the culture.

15. An expression cassette comprising a nucleic acid molecule encoding a polypeptide having lipolytic activity, wherein the polypeptide comprises an amino acid sequence having at least 90% amino acid sequence identity to the amino acid sequence of SEQ ID NO:40, and wherein the nucleic acid molecule encoding a polypeptide having lipolytic activity is operably linked to a heterologous promoter.

16. A recombinant microorganism comprising a non-native nucleic acid molecule encoding a polypeptide having lipolytic activity, wherein the polypeptide comprises an amino acid sequence having at least 85% amino acid sequence identity to an amino acid sequence selected from the group consisting of SEQ ID NO:38 and SEQ ID NO:47, and wherein the recombinant microorganism has attenuated expression of
- at least one endogenous gene selected from the group consisting of an acyl-CoA synthetase gene and an acyl-ACP synthetase gene as compared to a corresponding wild-type microorganism, and wherein
- the recombinant microorganism produces at least one free fatty acid or at least one fatty acid derivative.

17. A recombinant microorganism comprising the expression cassette of claim 15.

18. An expression cassette comprising a nucleic acid molecule encoding a polypeptide having lipolytic activity, wherein the polypeptide comprises an amino acid sequence having at least 85% amino acid sequence identity to an amino acid sequence selected from the group consisting of SEQ ID NO:38 and SEQ ID NO:47, and wherein the nucleic acid molecule encoding a polypeptide having lipolytic activity is operably linked to a heterologous promoter.

19. The recombinant microorganism of claim 1, wherein the at least one endogenous gene is disrupted.

20. The recombinant microorganism of claim 16, wherein the at least one endogenous gene is disrupted.

21. The recombinant microorganism of claim 16, wherein the polypeptide having lipolytic activity is non-native to the recombinant microorganism.

22. A recombinant microorganism comprising a non-native nucleic acid molecule encoding a polypeptide having lipase activity, wherein the polypeptide comprises an amino acid sequence having at least 85% amino acid sequence identity to an amino acid sequence selected from the group consisting of SEQ ID NO:2, SEQ ID NO:4, and SEQ ID NO:6, and wherein the recombinant microorganism has attenuated expression of
- at least one endogenous gene selected from the group consisting of an acyl-CoA synthetase gene and an acyl-ACP synthetase gene as compared to a corresponding wild-type microorganism, and wherein
- the recombinant microorganism produces at least one free fatty acid or at least one fatty acid derivative.

23. The recombinant microorganism of claim 22, wherein the at least one endogenous gene is disrupted.

24. The recombinant microorganism of claim 22, wherein the polypeptide having lipase activity comprises an amino acid sequence having at least 85% sequence identity to an amino acid sequence selected from the group consisting of SEQ ID NO:4 and SEQ ID NO:6.

* * * * *

```
                       SEQUENCE LISTING

<160> NUMBER OF SEQ ID NOS: 47

<210> SEQ ID NO 1
<211> LENGTH: 609
<212> TYPE: DNA
<213> ORGANISM: Synechocystis sp. PCC 6803

<400> SEQUENCE: 1
atggtagcag aatttccgga ccgtcatcct gttgtgttag tccatggcat ttacgacacc      60
agggctaaat ttgccaccat ggtggatttt ttgaccaagg gcggctggtc agttcattgt     120
ttagacctag tgcccaacga tggcagtact tccctagcat tgttggcgga gcaagtgaag     180
caatatattg atcaaaaatt tgcgccccag caaccagtgg atttaattgg ttttagtatg     240
ggagggttag taacccgtta ttatttacaa cgactggggg gggggaacg ggttaggcgc     300 tacatcacca tttcagcccc caaccaaggt actctcctgg gttatagttt gccccaccaa     360
ggagtgaggg aaatggcctg gcagagtgac ttttttgaggg atttaaaccg agattgttgt     420
cagttattag cgggactcca ggtgacggtg atttggaccc ccttcgactt gatgattctg     480 cccccagta gttcccattt agaaattgga caagaaatta ttttgcctgt gctggtccat     540
gcctggatgg tgtcggatgc ccgttgtttg gcagaggtgg cttcggcttt ggctaaaccg     600
ttgccctga                                                              609

<210> SEQ ID NO 2
<211> LENGTH: 202
<212> TYPE: PRT
<213> ORGANISM: Synechocystis sp. PCC 6803

<400> SEQUENCE: 2

Met Val Ala Glu Phe Pro Asp Arg His Pro Val Val Leu Val His Gly
1               5                   10                  15

Ile Tyr Asp Thr Arg Ala Lys Phe Ala Thr Met Val Asp Phe Leu Thr
            20                  25                  30

Lys Gly Gly Trp Ser Val His Cys Leu Asp Leu Val Pro Asn Asp Gly
        35                  40                  45

Ser Thr Ser Leu Ala Leu Leu Ala Glu Glu Val Lys Gln Tyr Ile Asp
    50                  55                  60

Gln Lys Phe Ala Pro Gln Gln Pro Val Asp Leu Ile Gly Phe Ser Met
```

```
                65                  70                  75                  80
Gly Gly Leu Val Thr Arg Tyr Tyr Leu Gln Arg Leu Gly Gly Glu
                    85                  90                  95

Arg Val Arg Arg Tyr Ile Thr Ile Ser Ala Pro Asn Gln Gly Thr Leu
                100                 105                 110

Leu Gly Tyr Ser Leu Pro His Gln Gly Val Arg Glu Met Ala Trp Gln
                115                 120                 125

Ser Asp Phe Leu Arg Asp Leu Asn Arg Asp Cys Cys Gln Leu Leu Ala
130                 135                 140

Gly Leu Gln Val Thr Val Ile Trp Thr Pro Phe Asp Leu Met Ile Leu
145                 150                 155                 160

Pro Pro Ser Ser Ser His Leu Glu Ile Gly Gln Glu Ile Ile Leu Pro
                165                 170                 175

Val Leu Val His Ala Trp Met Val Ser Asp Ala Arg Cys Leu Ala Glu
                180                 185                 190

Val Ala Ser Ala Leu Ala Lys Pro Leu Pro
                195                 200
```

<210> SEQ ID NO 3
<211> LENGTH: 1224
<212> TYPE: DNA
<213> ORGANISM: Synechocystis sp. PCC 6803

<400> SEQUENCE: 3

```
atgccaatgg cgctttgggg catcgttttcc atcaaccagt ccagcccgac caggagagca    60
tcaaccatgg gcatctttaa ccgccgccga ctattgctgg ggggagtggc cctggggggga   120
gcattcacca taggccggga ggaacgccat cgccaggaaa tcaggggaatt acaggcatta   180
gccaaagccc aagcggccaa caccgaccgc accagcatgt aaatgccgc ctttgaagcg    240
gatgcggaaa aaatttaccg gggcgaggaa attattaaca gtgttaggct cactccccct   300
atcctgccct acgatcgcca aatttcccaa ttgctgatcc gttgcagtaa atcgccacc    360
cagcaatact taactgggaa aaccatccct agctacgacg gcaatattcg ccagttaccg   420
gcctatagct ccgacctgga tgagtataaa caaattgctt cttttcgcgg tagggaagct   480
cacatttccg aatccgttgc ggtgcaaatt ccctgggata taccggtga ccccttagat    540
aaaacctggg accaagcgga agattccctg ggggaaacca ttcgtcaagt ggtcaaagta   600
acccaggaaa tccccgttta cctgggtttt atcctcagtt ctccccgccg caatctcatt   660
gttttttcggg gtacccaaac caccatggaa tgggtcaata atctccgggc caacaaatt    720
cccttcaccg aacggcgatc ggggcaatat tttggcaaaa ttcaccaggg ctttatcgaa   780
aattatctcc gtattgtcag tcccattccg agggaaattg cccagcagtt agacccggcc   840
gtgccctgtt acgtcactgg ccatagtttg ggggcttccc tggcggtgct ggcggcgttg   900
gatctagcgg ttaacctccc caacttacgg tccagattc aactttatag ctatgcctgc    960
cccagggtcg gcgatgtgac ctttgcccaa ctccattccc gccaagtgcc caacagttac   1020
cgtattgtta acctcgcaga cgtgattccc ctcctgcccc ccactacggg gttaggcacc   1080
tatgtccatg tcgggcaaag ttggagtttc ctcagccaag gaggggacat cttacccaac   1140
catgtggtgg atacctacca gggagcagtg gatagggaag tggaaacgga tcagtccaga   1200
gattatccaa tcgccgccgt ttga                                          1224
```

<210> SEQ ID NO 4
<211> LENGTH: 407

<212> TYPE: PRT
<213> ORGANISM: Synechocystis sp. PCC 6803

<400> SEQUENCE: 4

```
Met Pro Met Ala Leu Trp Gly Ile Val Ser Ile Asn Gln Ser Ser Pro
1               5                   10                  15

Thr Arg Arg Ala Ser Thr Met Gly Ile Phe Asn Arg Arg Leu Leu
            20                  25                  30

Leu Gly Gly Val Ala Leu Gly Gly Ala Phe Thr Ile Gly Arg Glu Glu
            35                  40                  45

Arg His Arg Gln Glu Ile Arg Glu Leu Gln Ala Leu Ala Lys Ala Gln
        50                  55                  60

Ala Ala Asn Thr Asp Arg Thr Ser Met Leu Asn Ala Ala Phe Glu Ala
65                  70                  75                  80

Asp Ala Glu Lys Ile Tyr Arg Gly Glu Glu Ile Asn Ser Val Arg
                85                  90                  95

Leu Thr Pro Pro Ile Leu Pro Tyr Asp Arg Gln Ile Ser Gln Leu Leu
            100                 105                 110

Ile Arg Cys Ser Lys Ile Ala Thr Gln Gln Tyr Leu Thr Gly Lys Thr
        115                 120                 125

Ile Pro Ser Tyr Asp Gly Asn Ile Arg Gln Leu Pro Ala Tyr Ser Ser
130                 135                 140

Asp Leu Asp Glu Tyr Lys Gln Ile Ala Ser Phe Arg Gly Arg Glu Ala
145                 150                 155                 160

His Ile Ser Glu Ser Val Ala Val Gln Ile Pro Leu Asp Asn Thr Gly
                165                 170                 175

Asp Pro Leu Asp Lys Thr Trp Asp Gln Ala Glu Asp Ser Leu Gly Glu
            180                 185                 190

Thr Ile Arg Gln Val Val Lys Val Thr Gln Glu Ile Pro Val Tyr Leu
        195                 200                 205

Gly Phe Ile Leu Ser Ser Pro Arg Arg Asn Leu Ile Val Phe Arg Gly
    210                 215                 220

Thr Gln Thr Thr Met Glu Trp Val Asn Asn Leu Arg Ala Gln Gln Ile
225                 230                 235                 240

Pro Phe Thr Glu Arg Arg Ser Gly Gln Tyr Phe Gly Lys Ile His Gln
                245                 250                 255

Gly Phe Ile Glu Asn Tyr Leu Arg Ile Val Ser Pro Ile Pro Arg Glu
            260                 265                 270

Ile Ala Gln Gln Leu Asp Pro Ala Val Pro Cys Tyr Val Thr Gly His
        275                 280                 285

Ser Leu Gly Ala Ser Leu Ala Val Leu Ala Ala Leu Asp Leu Ala Val
    290                 295                 300

Asn Leu Pro Asn Leu Arg Ser Gln Ile Gln Leu Tyr Ser Tyr Ala Cys
305                 310                 315                 320

Pro Arg Val Gly Asp Val Thr Phe Ala Gln Leu His Ser Arg Gln Val
                325                 330                 335

Pro Asn Ser Tyr Arg Ile Val Asn Leu Ala Asp Val Ile Pro Leu Leu
            340                 345                 350

Pro Pro Thr Thr Gly Leu Gly Thr Tyr Val His Val Gly Gln Ser Trp
        355                 360                 365

Ser Phe Leu Ser Gln Gly Gly Asp Ile Leu Pro Asn His Val Val Asp
    370                 375                 380

Thr Tyr Gln Gly Ala Val Asp Arg Glu Val Glu Thr Asp Gln Ser Arg
385                 390                 395                 400
```

Asp Tyr Pro Ile Ala Ala Val
          405

<210> SEQ ID NO 5
<211> LENGTH: 981
<212> TYPE: DNA
<213> ORGANISM: Saccharomyces cerevisiae

<400> SEQUENCE: 5

```
atgaaaaatg ataataaagc taatgatata ataatagact ccgtcaaagt tcctgattcg      60
tacaagcccc caaaaaatcc tattgtattt tgccatggtt tatcaggatt tgacaaatta     120
attctaatcc cttctgtatt ccatctgaca aacctaattt ccaattcaat agtacataat     180
atggcagaaa atttcatgca ggatgacgaa gataagagtg ataacaagta cacaaatttg     240
ttggagattg aatattggat tggcgttaaa aaatttcttc aatctaaggg atgtactgtt     300
atcaccacta aggtaccagg ttttggtagc atcgaggaaa gagcaatggc tttggatgct     360
cagttacaga aagaagtaaa gaaaatcgag tcgaaggata agcgacattc gttaaatcta     420
atcgcacact caatgggggg actagactgc cgatatctaa tttgcaatat aaaaaatagg     480
aattacgata tattgagcct aaccactatt tcaactccac atagagggtc agaaatggcc     540
gattacgtag tcgaccttt tgaaaatcta atgccttga gagttagcca aaagatattg       600
ccaatatgtt tctaccaact cacgactgcg tatatgaaat atttcaattt ggttacgcca     660
aatagtccaa aagtctctta tttttcgtat ggatgctcct ttgtgcctaa gtggtacaat     720
gtcttttgta ctccctggaa aattgtttat gaaaggtcta aaggttgccc caacgatggc     780
cttgtaacca taaatagtag taaatggggt gaatacaggg ggactttgaa ggacatggat     840
catctggacg tcatcaattg gaaaaataag ttacaggatg attggagtaa attttttcgt     900
accactactg tcggagagaa ggttgacatc ctgaattttt acttgaagat aaccgatgac     960
ttggcaagaa aaggatttta a                                               981
```

<210> SEQ ID NO 6
<211> LENGTH: 326
<212> TYPE: PRT
<213> ORGANISM: Saccharomyces cerevisiae

<400> SEQUENCE: 6

Met Lys Asn Asp Asn Lys Ala Asn Asp Ile Ile Asp Ser Val Lys
1               5                   10                  15

Val Pro Asp Ser Tyr Lys Pro Pro Lys Asn Pro Ile Val Phe Cys His
            20                  25                  30

Gly Leu Ser Gly Phe Asp Lys Leu Ile Leu Ile Pro Ser Val Phe His
        35                  40                  45

Leu Thr Asn Leu Ile Ser Asn Ser Ile Val His Asn Met Ala Glu Asn
    50                  55                  60

Phe Met Gln Asp Asp Glu Asp Lys Ser Asp Asn Lys Tyr Thr Asn Leu
65                  70                  75                  80

Leu Glu Ile Glu Tyr Trp Ile Gly Val Lys Lys Phe Leu Gln Ser Lys
                85                  90                  95

Gly Cys Thr Val Ile Thr Thr Lys Val Pro Gly Phe Gly Ser Ile Glu
            100                 105                 110

Glu Arg Ala Met Ala Leu Asp Ala Gln Leu Gln Lys Glu Val Lys Lys
        115                 120                 125

Ile Glu Ser Lys Asp Lys Arg His Ser Leu Asn Leu Ile Ala His Ser

```
                130              135              140
Met Gly Gly Leu Asp Cys Arg Tyr Leu Ile Cys Asn Ile Lys Asn Arg
145              150              155              160

Asn Tyr Asp Ile Leu Ser Leu Thr Thr Ile Ser Thr Pro His Arg Gly
            165              170              175

Ser Glu Met Ala Asp Tyr Val Val Asp Leu Phe Glu Asn Leu Asn Ala
            180              185              190

Leu Arg Val Ser Gln Lys Ile Leu Pro Ile Cys Phe Tyr Gln Leu Thr
            195              200              205

Thr Ala Tyr Met Lys Tyr Phe Asn Leu Val Thr Pro Asn Ser Pro Lys
210              215              220

Val Ser Tyr Phe Ser Tyr Gly Cys Ser Phe Val Pro Lys Trp Tyr Asn
225              230              235              240

Val Phe Cys Thr Pro Trp Lys Ile Val Tyr Glu Arg Ser Lys Gly Cys
            245              250              255

Pro Asn Asp Gly Leu Val Thr Ile Asn Ser Ser Lys Trp Gly Glu Tyr
            260              265              270

Arg Gly Thr Leu Lys Asp Met Asp His Leu Asp Val Ile Asn Trp Lys
            275              280              285

Asn Lys Leu Gln Asp Asp Trp Ser Lys Phe Phe Arg Thr Thr Thr Val
            290              295              300

Gly Glu Lys Val Asp Ile Leu Asn Phe Tyr Leu Lys Ile Thr Asp Asp
305              310              315              320

Leu Ala Arg Lys Gly Phe
                325

<210> SEQ ID NO 7
<211> LENGTH: 90
<212> TYPE: DNA
<213> ORGANISM: Artificial Sequence
<220> FEATURE:
<223> OTHER INFORMATION: TrcY promoter

<400> SEQUENCE: 7
ctgaaatgag ctgttgacaa ttaatcatcc ggctcgtata atgtgtggaa ttgtgagcgg     60
ataacaattt cacactaagg aggaaaaaaa                                       90

<210> SEQ ID NO 8
<211> LENGTH: 44
<212> TYPE: DNA
<213> ORGANISM: Artificial Sequence
<220> FEATURE:
<223> OTHER INFORMATION: Primer tw37

<400> SEQUENCE: 8
cacactaagg aggaaaaaaa ccatggtagc agaatttccg gacc                       44

<210> SEQ ID NO 9
<211> LENGTH: 40
<212> TYPE: DNA
<213> ORGANISM: Artificial Sequence
<220> FEATURE:
<223> OTHER INFORMATION: Primer tw38

<400> SEQUENCE: 9
gtaccatatg catgcgagct ctcagggcaa cggtttagcc                            40

<210> SEQ ID NO 10
<211> LENGTH: 21
```

```
<212> TYPE: DNA
<213> ORGANISM: Artificial Sequence
<220> FEATURE:
<223> OTHER INFORMATION: Primer RS6803-5

<400> SEQUENCE: 10
attgctgaag cggaatccct g                                              21

<210> SEQ ID NO 11
<211> LENGTH: 58
<212> TYPE: DNA
<213> ORGANISM: Artificial Sequence
<220> FEATURE:
<223> OTHER INFORMATION: Primer RSMCS-3

<400> SEQUENCE: 11
catggagatc tgagctcgca tgcatatggt accatataac catcaaagcc atagttgg     58

<210> SEQ ID NO 12
<211> LENGTH: 58
<212> TYPE: DNA
<213> ORGANISM: Artificial Sequence
<220> FEATURE:
<223> OTHER INFORMATION: Primer RSMCS-5

<400> SEQUENCE: 12
atatgcatgc gagctcagat ctccatggaa ttcggtaccg gtatggatgg caccgatg     58

<210> SEQ ID NO 13
<211> LENGTH: 21
<212> TYPE: DNA
<213> ORGANISM: Artificial Sequence
<220> FEATURE:
<223> OTHER INFORMATION: Primer RS6803-3

<400> SEQUENCE: 13
tgggggacca ttctctggat c                                              21

<210> SEQ ID NO 14
<211> LENGTH: 39
<212> TYPE: DNA
<213> ORGANISM: Artificial Sequence
<220> FEATURE:
<223> OTHER INFORMATION: Primer NS2-5MCS

<400> SEQUENCE: 14
gcatgcgagc tcagatctac caggttgtcc ttggcgcag                           39

<210> SEQ ID NO 15
<211> LENGTH: 39
<212> TYPE: DNA
<213> ORGANISM: Artificial Sequence
<220> FEATURE:
<223> OTHER INFORMATION: Primer NS21-3MCS

<400> SEQUENCE: 15
ccataccggt accgaattcg ccacgttact gctcgatgg                           39

<210> SEQ ID NO 16
<211> LENGTH: 70
<212> TYPE: DNA
<213> ORGANISM: Artificial Sequence
<220> FEATURE:
<223> OTHER INFORMATION: Primer 4YC-trcY-5

<400> SEQUENCE: 16
```

```
actagtcctg aggctgaaat gagctgttga caattaatca tccggctcgt ataatgtgtg    60
gaattgtgag                                                            70

<210> SEQ ID NO 17
<211> LENGTH: 70
<212> TYPE: DNA
<213> ORGANISM: Artificial Sequence
<220> FEATURE:
<223> OTHER INFORMATION: Primer 4YC-trcY-3

<400> SEQUENCE: 17
ccatggtttt tttcctcctt agtgtgaaat tgttatccgc tcacaattcc acacattata    60
cgagccggat                                                            70

<210> SEQ ID NO 18
<211> LENGTH: 9153
<212> TYPE: DNA
<213> ORGANISM: Artificial Sequence
<220> FEATURE:
<223> OTHER INFORMATION: pSGI-TW10

<400> SEQUENCE: 18
gttctttcct gcgttatccc ctgattctgt ggataaccgt attaccgcct ttgagtgagc    60
tgataccgct cgccgcagcc gaacgaccga gcgcagcgag tcagtgagcg aggaagcgga   120
agagcgccca atacgcaaac cgcctctccc cgcgcgttgg ccgattcatt aatgcagctg   180
gcacgacagg tttcccgact ggaaagcggg cagtgagcgc aacgcaatta atgtgagtta   240
gctcactcat taggcacccc aggctttaca ctttatgctt ccggctcgta tgttgtgtgg   300
aattgtgagc ggataacaat ttcacacagg aaacagctat gaccatgatt acgaatttgg   360
gggaccattc tctggatcat tgccggggcc accgggatta taaaccgccg aataatcccc   420
ttcggagggc aaagcaaccc tcttaatttg gcgaactgcg gcttcgtccc ctttgaggat   480
aatgtcgtaa tagttgtcat gatcttcgat gtaagtcagg tcatagctgt cctgaacccc   540
ggccaaatcc gccagcccca cacctgcac cagaccaaag ccgggaattt cataatcaac   600
accagtttgg gttaggataa ctgtccgtcc cgtaatatct tccgcttgga gttgaaaata   660
ccgttcaaat tctgtgggta gtaaactggc aatgccatcg ggggaaaaac cggcgctggt   720
gtaaattcgc aaacgaaatt gggcttggtc tccatataaa tccccgccac tgttattttg   780
attggtggct aaccagaggg gagcccctt ccccaggtca ctgaagcggt ctaacttagc   840
ggcgacaatt ttgggaccat tgccggccac gtaggggttg agactatcaa tggtaatacc   900
caccgcactg accgggccgt gggtcccac catttccaaa ggagtactgt ccaacactgt   960
gcctacggaa acgggataaa tcgctccctc cgtgcctggg gttaaacgat taccaaaatt  1020
gcccgtaatt actaccgttt gccgttcgtt gtattcactg ttgggaatca agaggcgat   1080 caccggggtg acaatttccc ccgtgttaag cattacctga aaatctgtgg gattaagggt  1140
ggtgggaaaa atgggccacg caaaaacaat gggaatgtta tcgttttttt ccagattaac  1200
gccataaaca ctctgcactg tgtctgtgct aatagccgaa gtgtaggccc gttgggtggt  1260
ggtggacaaa tccccaggt tattccaggc cacattgttg tcaaaggcaa tctgttggga  1320
ttccgcatcg gtgccatcca taccggtacc gaattcgccc ttctaagctt gcgcgaaggc  1380
gaagcggcat gcatttacgt tgacaccatc gaatggtgca aaaccttcg cggtatggca  1440 tgatagcgcc cggaagagag tcaattcagg gtggtgaatg tgaaaccagt aacgttatac  1500
gatgtcgcag agtatgccgg tgtctcttat cagaccgttt cccgcgtggt gaaccaggcc  1560
```

```
agccacgttt ctgcgaaaac gcgggaaaaa gtggaagcgg cgatggcgga gctgaattac    1620
attcccaacc gcgtggcaca acaactggcg ggcaaacagt cgttgctgat tggcgttgcc    1680
acctccagtc tggccctgca cgcgccgtcg caaattgtcg cggcgattaa atctcgcgcc    1740
gatcaactgg gtgccagcgt ggtggtgtcg atggtagaac gaagcggcgt cgaagcctgt    1800
aaagcggcgg tgcacaatct tctcgcgcaa cgcgtcagtg ggctgatcat taactatccg    1860
ctggatgacc aggatgccat tgctgtgaa gctgcctgca ctaatgttcc ggcgttattt      1920
cttgatgtct ctgaccagac acccatcaac agtattattt tctcccatga agacggtacg    1980
cgactgggcg tggagcatct ggtcgcattg ggtcaccagc aaatcgcgct gttagcgggc    2040
ccattaagtt ctgtctcggc gcgtctgcgt ctggctggct ggcataaata tctcactcgc    2100
aatcaaattc agccgatagc ggaacggaa ggcgactgga gtgccatgtc cggttttcaa       2160
caaaccatgc aaatgctgaa tgagggcatc gttcccactg cgatgctggt tgccaacgat    2220
cagatggcgc tgggcgcaat gcgcgccatt accgagtccg ggctgcgcgt tggtgcggat    2280
atctcggtag tgggatacga cgataccgaa gacagctcat gttatatccc gccgtcaacc    2340
accatcaaac aggattttcg cctgctgggg caaaccagcg tggaccgctt gctgcaactc    2400
tctcagggcc aggcggtgaa gggcaatcag ctgttgcccg tctcactggt gaaaagaaaa    2460
accaccctgg cgcccaatac gcaaaccgcc tctccccgcg cgttggccga ttcattaatg    2520
cagctggcac gacaggtttc ccgactggaa agcgggcagt gagcgcaacg caattaatgt    2580
gagttagcgc gaattgatct gaagcttgaa agggcgaatt cgccacgtta ctgctcgatg    2640
gcattcagca gcgatcgccc gaatatcgtc agcggatttt gcatcacgaa gcgggtcact    2700
acttggtagc aaccgcgctg gggttaccag atcgacctgc aggggggggg gggcgctgag    2760
gtctgcctcg tgaagaaggt gttgctgact cataccaggc ctgaatcgcc ccatcatcca    2820
gccagaaagt gagggagcca cggttgatga gagctttgtt gtaggtggac cagttggtga    2880
ttttgaactt ttgctttgcc acggaacggt ctgcgttgtc gggaagatgc gtgatctgat    2940
ccttcaactc agcaaaagtt cgatttattc aacaaagccg ccgtcccgtc aagtcagcgt    3000
aatgctctgc cagtgttaca accaattaac caattctgat tagaaaaact catcgagcat    3060
caaatgaaac tgcaatttat tcatatcagg attatcaata ccatattttt gaaaaagccg    3120
tttctgtaat gaaggagaaa actcaccgag gcagttccat aggatggcaa gatcctggta    3180
tcggtctgcg attccgactc gtccaacatc aatacaacct attaatttcc cctcgtcaaa    3240
aataaggtta tcaagtgaga atcaccatg agtgacgact gaatccggtg agaatggcaa    3300
aagcttatgc atttctttcc agacttgttc aacaggccag ccattacgct cgtcatcaaa    3360
atcactcgca tcaaccaaac cgttattcat tcgtgattgc gcctgagcga gacgaaatac    3420
gcgatcgctg ttaaaaggac aattacaaac aggaatcgaa tgcaaccggc gcaggaacac    3480
tgccagcgca tcaacaatat tttcacctga atcaggatat tcttctaata cctgaatgc     3540 tgttttcccg gggatcgcag tggtgagtaa ccatgcatca tcaggagtac ggataaaatg    3600
cttgatggtc ggaagaggca taaattccgt cagccagttt agtctgacca tctcatctgt    3660
aacatcattg gcaacgctac ctttgccatg tttcagaaac aactctggcg catcgggctt    3720
cccatacaat cgatagattg tcgcacctga ttgcccgaca ttatcgcgag cccatttata    3780
cccatataaa tcagcatcca tgttggaatt taatcgcggc ctcgagcaag acgtttcccg    3840
ttgaatatgg ctcataacac cccttgtatt actgtttatg taagcagaca gttttattgt    3900
```

```
tcatgatgat atattttat cttgtgcaat gtaacatcag agattttgag acacaacgtg    3960
gctttccccc cccccctgc aggtcgatct aagcttgctt ctttgctgac gagtggcgga    4020
cgggtgagta atgtctggga aactgcctga tggagggga taactactgg aaacggtagc    4080
taataccgca taacgtcgca agaccaaaga ggggaccttt cgggcctctt gccatcggat    4140
gtgcccagat gggattagct agtaggtggg gtaacggctc aataaaacag aatttgcctg    4200
gcggcagtag cgcggtggtc ccacctgacc ccatgccgaa ctcagaagtg aaacgccgta    4260
gcgccgatgg tagtgtgggg tctccccatg cgagagtagg gaactgccag gcatcaaata    4320
aaacgaaagg ctcagtcgaa agactgggcc tttcgtttta tctgttgttt gtcggtgaac    4380
gctctcctga gtaggacaaa tccgccggga gcggatttga acgttgcgaa gcaacggccc    4440
ggagggtggc gggcaggacg cccgccataa actgccaggc atcaaattaa gcagaaggcc    4500
atcctgacgg atggcctttt gcgtttcta caaactccgg atccgccgg atccggccaa    4560
gcttgctagc tcgagcccgg gtctagaggc ctgtcgacga tatccggttac ccgtgacggg    4620
ctacaccctc tcagcgtggg aagcgctgcg ccaaggacaa cctggtagat ccactagtcc    4680
tgaggctgaa atgagctgtt gacaattaat catccggctc gtataatgtg tggaattgtg    4740
agcggataac aatttcacac taaggaggaa aaaaccatg gtagcagaat tccggaccg    4800
tcatcctgtt gtgttagtcc atggcattta cgacaccagg gctaaatttg ccaccatggt    4860
ggattttttg accaagggcg gctggtcagt tcattgttta gacctagtgc caacgatgg    4920
cagtacttcc ctagcattgt tggcggagca agtgaagcaa tatattgatc aaaaatttgc    4980
gccccagcaa ccagtggatt taattggttt tagtatggga gggttagtaa cccgttatta    5040
tttacaacga ctggggggg gggaacgggt taggcgctac atcaccattt cagcccccaa    5100
ccaaggtact ctcctgggtt atagtttgcc ccaccaagga gtgagggaaa tggcctggca    5160
gagtgacttt ttgagggatt taaaccgaga ttgttgtcag ttattagcgg gactccaggt    5220
gacggtgatt tggaccccct tcgacttgat gattctgccc cccagtagtt cccatttaga    5280
aattggacaa gaaattattt tgcctgtgct ggtccatgcc tggatggtgt cggatgcccg    5340
ttgtttggca gaggtggctt cggctttggc taaaccgttg ccctgagagc tcgcatgcat    5400
atggtaccat ataaccatca agccatagt tggctgttac aattcccct tcctgattga    5460
ataggtcact gctgagcaga atactggtgt tgagggaact actcttggcg ctgagattta    5520
ggcgatcggc ggcgaggtag gccaacaggc gatcggctag gggggtgtat tgaatagtca    5580
tagattaatt caacagtaat atttcacaaa gttatcgagt ttgaactcgc ataattgca    5640
ttaattaagt tgatttaaac actcgcactg agggccaggg tggcatcttg atattctgtc    5700
acaacttccc ccccatgcca ttcctgactg tccagggcca tttcttcaat taaactggct    5760
aacttcaggg ccttgagggc ctgttctccc cccactgagg gttgatcacc tcccctaaca    5820
caatgaataa aatgttctaa ttcagcgtgg agaggttcaa tattactggt gtaaacccttt    5880
tcgattagac catcctggcg atacaatacc tggccatagt ccgcgctcca atcagcggtg    5940
gtttggcgat ggatcaaaat ttcgttattg agaaaatccg cttcggtgag ggaattttg    6000
cagtgggcgg cgatgaacg aattttacga tgggtgacct tactggcggt gagggtggcc    6060
acaatgccgg aggagaagcc taacgtagcg gtgacataat ccaaatatcc tgacccagaa    6120
gcccgactgc cactgcggga cagtttaacc acttccgaac ccaccaattc cagcaacagg    6180
tcaatgtcat ggatcatcaa atccaatacc acggagacat cattgcccg ctgggaatag    6240
ggactcatgc gatgggcttc gatcgccaat aactcttccg ttttgagaat tttggttagc    6300
```

```
tctaaaaatg ccgggttgaa gcgttcaatg tgccccactt ggagaatgca attggcatcg   6360
gcggcggcat taaccaggga ttccgcttca gcaatagctt ggcactggcc gtcgttttac   6420
aacgtcgtga ctgggaaaac cctggcgtta cccaacttaa tcgccttgca gcacatcccc   6480
ctttcgccag ctggcgtaat agcgaagagg cccgcaccga tcgcccttcc caacagttgc   6540
gcagcctgaa tggcgaatgg cgcctgatgc ggtattttct ccttacgcat ctgtgcggta   6600
tttcacaccg catacgtcaa agcaaccata gtacgcgccc tgtagcggcg cattaagcgc   6660
ggcgggtgtg gtggttacgc gcagcgtgac cgctacactt gccagcgccc tagcgcccgc   6720
tcctttcgct ttcttccctt cctttctcgc cacgttcgcc ggctttcccc gtcaagctct   6780
aaatcggggg ctccctttag ggttccgatt tagtgcttta cggcacctcg accccaaaaa   6840
acttgatttg ggtgatggtt cacgtagtgg gccatcgccc tgatagacgg ttttcgccc    6900 tttgacgttg gagtccacgt tctttaatag tggactcttg ttccaaactg gaacaacact   6960
caaccctatc tcgggctatt cttttgattt ataagggatt tgccgatttc ggcctattg    7020 gttaaaaaat gagctgattt aacaaaaatt taacgcgaat tttaacaaaa tattaacgtt   7080
tacaatttta tggtgcactc tcagtacaat ctgctctgat gccgcatagt taagccagcc   7140
ccgacacccg ccaacacccg ctgacgcgcc ctgacgggct tgtctgctcc cggcatccgc   7200
ttacagacaa gctgtgaccg tctccgggag ctgcatgtgt cagaggtttt caccgtcatc   7260
accgaaacgc gcgagacgaa agggcctcgt gatacgccta ttttataggt taatgtcat    7320 gataataatg gtttcttaga cgtcaggtgg cacttttcgg ggaaatgtgc gcggaacccc   7380
tatttgttta ttttctaaa tacattcaaa tatgtatccg ctcatgagac aataaccctg    7440
ataaatgctt caataatatt gaaaaaggaa gagtatgagt attcaacatt tccgtgtcgc   7500
ccttattccc ttttttgcgg cattttgcct tcctgttttt gctcacccag aaacgctggt   7560
gaaagtaaaa gatgctgaag atcagttggg tgcacgagtg ggttacatcg aactggatct   7620
caacagcggt aagatccttg agagttttcg ccccgaagaa cgttttccaa tgatgagcac   7680
ttttaaagtt ctgctatgtg gcgcggtatt atcccgtatt gacgccgggc aagagcaact   7740
cggtcgccgc atacactatt ctcagaatga cttggttgag tactcaccag tcacagaaaa   7800
gcatcttacg gatggcatga cagtaagaga attatgcagt gctgccataa ccatgagtga   7860
taacactgcg gccaacttac ttctgacaac gatcggagga ccgaaggagc taaccgcttt   7920
tttgcacaac atgggggatc atgtaactcg ccttgatcgt tgggaaccgg agctgaatga   7980
agccatacca aacgacgagc gtgacaccac gatgcctgta gcaatggcaa caacgttgcg   8040
caaactatta actggcgaac tacttactct agcttcccgg caacaattaa tagactggat   8100
ggaggcggat aaagttgcag gaccacttct gcgctcggcc cttccggctg ctggtttat    8160 tgctgataaa tctggagccg gtgagcgtgg gtctcgcggt atcattgcag cactggggcc   8220
agatggtaag ccctcccgta tcgtagttat ctacacgacg gggagtcagg caactatgga   8280
tgaacgaaat agacagatcg ctgagatagg tgcctcactg attaagcatt ggtaactgtc   8340
agaccaagtt tactcatata cttttagat tgatttaaaa cttcatttt aatttaaaag     8400 gatctaggtg aagatccttt ttgataatct catgaccaaa atcccttaac gtgagttttc   8460
gttccactga gcgtcagacc ccgtagaaaa gatcaaagga tcttcttgag atcctttttt   8520
tctgcgcgta atctgctgct tgcaaacaaa aaaaccaccg ctaccagcgg tggtttgttt   8580
gccggatcaa gagctaccaa ctcttttttcc gaaggtaact ggcttcagca gagcgcagat   8640
```

| accaaatact gtccttctag tgtagccgta gttaggccac cacttcaaga actctgtagc | 8700 |
| accgcctaca tacctcgctc tgctaatcct gttaccagtg gctgctgcca gtggcgataa | 8760 |
| gtcgtgtctt accgggttgg actcaagacg atagttaccg gataaggcgc agcggtcggg | 8820 |
| ctgaacgggg ggttcgtgca cacagcccag cttggagcga acgacctaca ccgaactgag | 8880 |
| atacctacag cgtgagctat gagaaagcgc cacgcttccc gaagggagaa aggcggacag | 8940 |
| gtatccggta gcggcaggg tcggaacagg agagcgcacg agggagcttc caggggggaaa | 9000 |
| cgcctggtat ctttatagtc ctgtcgggtt tcgccacctc tgacttgagc gtcgattttt | 9060 |
| gtgatgctcg tcagggggc ggagcctatg gaaaaacgcc agcaacgcgg ccttttttacg | 9120 |
| gttcctggcc ttttgctggc cttttgctca cat | 9153 |

```
<210> SEQ ID NO 19
<211> LENGTH: 41
<212> TYPE: DNA
<213> ORGANISM: Artificial Sequence
<220> FEATURE:
<223> OTHER INFORMATION: Primer tw39

<400> SEQUENCE: 19
```

| cacactaagg aggaaaaaaa ccatgaaaaa tgataataag c | 41 |

```
<210> SEQ ID NO 20
<211> LENGTH: 44
<212> TYPE: DNA
<213> ORGANISM: Artificial Sequence
<220> FEATURE:
<223> OTHER INFORMATION: Primer tw40

<400> SEQUENCE: 20
```

| ggtaccatat gcatgcgagc tcttaaaatc cttttcttgc caag | 44 |

```
<210> SEQ ID NO 21
<211> LENGTH: 9525
<212> TYPE: DNA
<213> ORGANISM: Artificial Sequence
<220> FEATURE:
<223> OTHER INFORMATION: pSGI-TW11

<400> SEQUENCE: 21
```

| gttctttcct gcgttatccc ctgattctgt ggataaccgt attaccgcct ttgagtgagc | 60 |
| tgataccgct cgccgcagcc gaacgaccga gcgcagcgag tcagtgagcg aggaagcgga | 120 |
| agagcgccca atacgcaaac cgcctctccc cgcgcgttgg ccgattcatt aatgcagctg | 180 |
| gcacgacagg tttcccgact ggaaagcggg cagtgagcgc aacgcaatta atgtgagtta | 240 |
| gctcactcat taggcacccc aggctttaca ctttatgctt ccggctcgta tgttgtgtgg | 300 |
| aattgtgagc ggataacaat ttcacacagg aaacagctat gaccatgatt acgaatttgg | 360 |
| gggaccattc tctggatcat tgccggggc accgggatta taaaccgccg aataatcccc | 420 |
| ttcggagggc aaagcaaccc tcttaatttg gcgaactgcg gcttcgtccc ctttgaggat | 480 |
| aatgtcgtaa tagttgtcat gatcttcgat gtaagtcagg tcatagctgt cctgaacccc | 540 |
| ggccaaatcc gccagcccca acacctgcac cagaccaaag ccgggaattt cataatcaac | 600 |
| accagtttgg gttaggataa ctgtccgtcc cgtaatatct tccgcttgga gttgaaaata | 660 |
| ccgttcaaat tctgtgggta gtaaactggc aatgccatcg ggggaaaaac cggcgctggt | 720 |
| gtaaattcgc aaacgaaatt gggcttggtc tccatataaa tccccgccac tgttattttg | 780 |
| attggtggct aaccagaggg gagcccctttc ccccaggtca ctgaagcggt ctaacttagc | 840 |

```
ggcgacaatt ttgggaccat tgccggccac gtaggggttg agactatcaa tggtaatacc      900
caccgcactg accgggccgt tgggtcccac catttccaaa ggagtactgt ccaacactgt      960
gcctacggaa acgggataaa tcgctccctc cgtgcctggg gttaaacgat taccaaaatt     1020
gcccgtaatt actaccgttt gccgttcgtt gtattcactg ttgggaatca agaggcgat      1080
caccggggtg acaatttccc ccgtgttaag cattacctga aaatctgtgg gattaagggt     1140
ggtgggaaaa atgggccacg caaaaacaat gggaatgtta tcgttttttt ccagattaac     1200
gccataaaca ctctgcactg tgtctgtgct aatagccgaa gtgtaggccc gttgggtggt     1260
ggtgacaaa tccccaggt tattccaggc cacattgttg tcaaaggcaa tctgttggga     1320
ttccgcatcg gtgccatcca taccggtacc gaattcgccc ttctaagctt gcgcgaaggc     1380
gaagcggcat gcatttacgt tgacaccatc gaatggtgca aaacctttcg cggtatggca     1440
tgatagcgcc cggaagagag tcaattcagg gtggtgaatg tgaaaccagt aacgttatac     1500
gatgtcgcag agtatgccgg tgtctcttat cagaccgttt cccgcgtggt gaaccaggcc     1560
agccacgttt ctgcgaaaac gcgggaaaaa gtggaagcgg cgatggcgga gctgaattac     1620
attcccaacc gcgtggcaca acaactggcg ggcaaacagt cgttgctgat tggcgttgcc     1680
acctccagtc tggccctgca cgcgccgtcg caaattgtcg cggcgattaa atctcgcgcc     1740
gatcaactgg gtgccagcgt ggtggtgtcg atggtagaac gaagcggcgt cgaagcctgt     1800
aaagcggcgg tgcacaatct tctcgcgcaa cgcgtcagtg ggctgatcat taactatccg     1860
ctggatgacc aggatgccat tgctgtggaa gctgcctgca ctaatgttcc ggcgttattt     1920
cttgatgtct ctgaccagac acccatcaac agtattattt tctcccatga agacggtacg     1980
cgactgggcg tggagcatct ggtcgcattg ggtcaccagc aaatcgcgct gttagcgggc     2040
ccattaagtt ctgtctcggc gcgtctgcgt ctggctggct ggcataaata tctcactcgc     2100
aatcaaattc agccgatagc ggaacgggaa ggcgactgga gtgccatgtc cggttttcaa     2160
caaaccatgc aaatgctgaa tgagggcatc gttcccactg cgatgctggt tgccaacgat     2220
cagatggcgc tgggcgcaat gcgcgccatt accgagtccg gctgcgcgt tggtgcggat     2280
atctcggtag tgggatacga cgataccgaa gacagctcat gttatatccc gccgtcaacc     2340
accatcaaac aggattttcg cctgctgggg caaaccagcg tggaccgctt gctgcaactc     2400
tctcagggcc aggcggtgaa gggcaatcag ctgttgcccg tctcactggt gaaaagaaaa     2460
accaccctgg cgcccaatac gcaaaccgcc tctccccgcg cgttggccga ttcattaatg     2520
cagctggcac gacaggtttc ccgactggaa agcgggcagt gagcgcaacg caattaatgt     2580
gagttagcgc gaattgatct gaagcttgaa agggcgaatt cgccacgtta ctgctcgatg     2640
gcattcagca gcgatcgccc gaatatcgtc agccggatttt gcatcacgaa gcgggtcact     2700
acttggtagc aaccgcgctg gggttaccag atcgacctgc agggggggg gggcgctgag     2760
gtctgcctcg tgaagaaggt gttgctgact cataccaggc ctgaatcgcc ccatcatcca     2820
gccagaaagt gagggagcca cggttgatga gagctttgtt gtaggtggac cagttggtga     2880
ttttgaactt ttgcttttgcc acggaacggt ctgcgttgtc gggaagatgc gtgatctgat     2940
ccttcaactc agcaaaagtt cgatttattc aacaaagccg ccgtcccgtc aagtcagcgt     3000
aatgctctgc cagtgttaca accaattaac caattctgat tagaaaaact catcgagcat     3060
caaatgaaac tgcaatttat tcatatcagg attatcaata ccatattttt gaaaaagccg     3120
tttctgtaat gaaggagaaa actcaccgag gcagttccat aggatggcaa gatcctggta     3180
```

```
tcggtctgcg attccgactc gtccaacatc aatacaacct attaatttcc cctcgtcaaa    3240
aataaggtta tcaagtgaga atcaccatg agtgacgact gaatccggtg agaatggcaa     3300
aagcttatgc atttctttcc agacttgttc aacaggccag ccattacgct cgtcatcaaa    3360
atcactcgca tcaaccaaac cgttattcat tcgtgattgc gcctgagcga gacgaaatac    3420
gcgatcgctg ttaaaaggac aattacaaac aggaatcgaa tgcaaccggc gcaggaacac    3480
tgccagcgca tcaacaatat tttcacctga atcaggatat tcttctaata cctggaatgc    3540
tgttttcccg gggatcgcag tggtgagtaa ccatgcatca tcaggagtac ggataaaatg    3600
cttgatggtc ggaagaggca taaattccgt cagccagttt agtctgacca tctcatctgt    3660
aacatcattg gcaacgctac ctttgccatg tttcagaaac aactctggcg catcgggctt    3720
cccatacaat cgatagattg tcgcacctga ttgcccgaca ttatcgcgag cccatttata    3780
cccatataaa tcagcatcca tgttggaatt taatcgcggc ctcgagcaag acgtttcccg    3840
ttgaatatgg ctcataacac cccttgtatt actgtttatg taagcagaca gttttattgt    3900
tcatgatgat atatttttat cttgtgcaat gtaacatcag agattttgag acacaacgtg    3960 gctttcccccc ccccccctgc aggtcgatct aagcttgctt ctttgctgac gagtggcgga    4020
cgggtgagta atgtctggga aactgcctga tgaggggggga taactactgg aaacggtagc    4080
taataccgca taacgtcgca agaccaaaga gggggaccct cgggcctctt gccatcggat    4140
gtgcccagat gggattagct agtaggtggg gtaacgctc aataaaacag aatttgcctg    4200
gcggcagtag cgcggtggtc ccacctgacc ccatgccgaa ctcagaagtg aaacgccgta    4260
gcgccgatgt agtgtgggg tctccccatg cgagagtagg gaactgccag gcatcaaata    4320
aaacgaaagg ctcagtcgaa agactgggcc tttcgtttta tctgttgttt gtcggtgaac    4380
gctctcctga gtaggacaaa tccgccggga gcggatttga acgttgcgaa gcaacggccc    4440
ggagggtggc gggcaggacg cccgccataa actgccaggc atcaaattaa gcagaaggcc    4500
atcctgacga tggccttttt gcgtttcta caaactccgg atccggccgg atccggccaa    4560
gcttgctagc tcgagcccgg gtctagaggc ctgtcgacga tatcggttac ccgtgacggg    4620
ctacaccctc tcagcgtggg aagcgctgcg ccaaggacaa cctggtagat ccactagtcc    4680
tgaggctgaa atgagctgtt gacaattaat catccggctc gtataatgtg tggaattgtg    4740
agcggataac aatttcacac taaggaggaa aaaaccatg aaaaatgata ataaagctaa    4800
tgatataata atagactccg tcaaagttcc tgattcgtac aagcccccaa aaaatcctat    4860
tgtattttgc catggtttat caggatttga caaattaatt ctaatcccctt ctgtattcca    4920 tctgacaaac ctaatttcca attcaatagt acataatatg gcagaaaatt tcatgcagga    4980
tgacgaagat aagagtgata acaagtacac aaatttgttg gagattgaat attggattgg    5040
cgttaaaaaa tttcttcaat ctaagggatg tactgttatc accactaagg taccaggttt    5100
tggtagcatc gaggaaagag caatggcttt ggatgctcag ttacagaaag aagtaaagaa    5160
aatcgagtcg aaggataagc gacattcgtt aaatctaatc gcacactcaa tgggggact    5220 agactgccga tatctaattt gcaatataaa aaataggaat tacgatatat tgagcctaac    5280
cactatttca actccacata gagggtcaga atggccgat tacgtagtcg accttttga    5340 aaatctaaat gccttgagag ttagccaaaa gatattgcca atatgtttct accaactcac    5400
gactgcgtat atgaaatatt tcaatttggt tacgccaaat agtccaaaag tctcttattt    5460
ttcgtatgga tgctcctttg tgcctaagtg gtacaatgtc ttttgtactc cctgaaaaat    5520
tgtttatgaa aggtctaaag gttgccccaa cgatggcctt gtaaccataa atagtagtaa    5580
```

```
atgggtgaa tacaggggga cttttgaagga catggatcat ctggacgtca tcaattggaa    5640
aaataagtta caggatgatt ggagtaaatt ttttcgtacc actactgtcg gagagaaggt    5700
tgacatcctg aattttact tgaagataac cgatgacttg gcaagaaaag gattttaaga    5760
gctcgcatgc atatggtacc atataaccat caaagccata gttggctgtt acaattcccc    5820
cttcctgatt gaataggtca ctgctgagca gaatactggt gttgagggaa ctactcttgg    5880
cgctgagatt taggcgatcg gcggcgaggt aggccaacag gcgatcggct aggggggtgt    5940
attgaatagt catagattaa ttcaacagta atatttcaca agttatcga gtttgaactc     6000 gcaataattg cattaattaa gttgatttaa acactcgcac tgagggccag ggtggcatct    6060
tgatattctg tcacaacttc cccccatgc cattcctgac tgtccagggc catttcttca     6120
attaaactgg ctaacttcag ggccttgagg gcctgttctc cccccactga gggttgatca    6180
cctcccctaa cacaatgaat aaaatgttct aattcagcgt ggagaggttc aatattactg    6240
gtgtaaacct tttcgattag accatcctgg cgatacaata cctggccata gtccgcgctc    6300
caatcagcgg tggtttggcg atggatcaaa atttcgttat tgagaaaatc cgcttcggtg    6360 agggaattt tgcagtgggc ggcgatgaa cgaattttac gatgggtgac cttactggcg     6420
gtgagggtgg ccacaatgcc ggaggagaag cctaacgtag cggtgacata atccaaatat    6480
cctgacccag aagcccgact gccactggcg gacagtttaa ccacttccga acccaccaat    6540
tccagcaaca ggtcaatgtc atggatcatc aaatccaata ccacggagac atcattggcc    6600
cgctgggaat agggactcat gcgatgggct tcgatcgcca ataactcttc cgttttgaga    6660 atttggtta gctctaaaaa tgccgggttg aagcgttcaa tgtgccccac ttggagaatg     6720
caattggcat cggcggcggc attaaccagg gattccgctt cagcaatagc ttggcactgg    6780
ccgtcgtttt acaacgtcgt gactgggaaa accctggcgt tacccaactt aatcgccttg    6840
cagcacatcc cccttttcgcc agctggcgta atagcgaaga ggcccgcacc gatcgccctt    6900
cccaacagtt gcgcagcctg aatggcgaat ggcgcctgat gcggtatttt ctccttacgc    6960
atctgtgcgg tatttcacac cgcatacgtc aaagcaacca tagtacgcgc cctgtagcgg    7020
cgcattaagc gcggcgggtg tggtggttac gcgcagcgtg accgctacac ttgccagcgc    7080
cctagcgccc gctcctttcg ctttcttccc ttcctttctc gccacgttcg ccggctttcc    7140
ccgtcaagct ctaaatcggg ggctcccttt agggttccga tttagtgctt tacggcacct    7200
cgaccccaaa aaacttgatt tgggtgatgg ttcacgtagt gggccatcgc cctgatagac    7260
ggtttttcgc cctttgacgt tggagtccac gttctttaat agtggactct tgttccaaac    7320
tggaacaaca ctcaacccta tctcgggcta ttcttttgat ttataaggga ttttgccgat    7380
ttcggcctat tggttaaaaa atgagctgat ttaacaaaaa tttaacgcga attttaacaa    7440
aatattaacg tttacaattt tatggtgcac tctcagtaca atctgctctg atgccgcata    7500
gttaagccag ccccgacacc cgccaacacc cgctgacgcg ccctgacggg cttgtctgct    7560
cccggcatcc gcttacagac aagctgtgac cgtctccggg agctgcatgt gtcagaggtt    7620
ttcaccgtca tcaccgaaac gcgcgagacg aaagggcctc gtgatacgcc tatttttata    7680
ggttaatgtc atgataataa tggtttctta gacgtcaggt ggcactttc ggggaaatgt     7740 gcgcggaacc cctatttgtt tatttttcta aatacattca aatatgtatc cgctcatgag    7800
acaataaccc tgataaatgc ttcaataata ttgaaaaagg aagagtatga gtattcaaca    7860
tttccgtgtc gcccttattc ccttttttgc ggcattttgc cttcctgttt ttgctcaccc    7920
```

```
agaaacgctg gtgaaagtaa aagatgctga agatcagttg ggtgcacgag tgggttacat    7980
cgaactggat ctcaacagcg gtaagatcct tgagagtttt cgccccgaag aacgttttcc    8040
aatgatgagc acttttaaag ttctgctatg tggcgcggta ttatcccgta ttgacgccgg    8100
gcaagagcaa ctcggtcgcc gcatacacta ttctcagaat gacttggttg agtactcacc    8160
agtcacagaa aagcatctta cggatggcat gacagtaaga gaattatgca gtgctgccat    8220
aaccatgagt gataacactg cggccaactt acttctgaca acgatcggag gaccgaagga    8280
gctaaccgct ttttgcaca acatggggga tcatgtaact cgccttgatc gttgggaacc    8340
ggagctgaat gaagccatac caaacgacga gcgtgacacc acgatgcctg tagcaatggc    8400
aacaacgttg cgcaaactat taactggcga actacttact ctagcttccc ggcaacaatt    8460
aatagactgg atggaggcgg ataaagttgc aggaccactt ctgcgctcgg cccttccggc    8520
tggctggttt attgctgata atctggagc cggtgagcgt gggtctcgcg gtatcattgc    8580
agcactgggg ccagatggta agccctcccg tatcgtagtt atctacacga cggggagtca    8640
ggcaactatg gatgaacgaa atagacagat cgctgagata ggtgcctcac tgattaagca    8700
ttggtaactg tcagaccaag tttactcata tatactttag attgatttaa aacttcattt    8760
ttaatttaaa aggatctagg tgaagatcct tttgataat ctcatgacca aaatccctta    8820
acgtgagttt tcgttccact gagcgtcaga ccccgtagaa aagatcaaag gatcttcttg    8880
agatccttt tttctgcgcg taatctgctg cttgcaaaca aaaaaaccac cgctaccagc    8940
ggtggtttgt ttgccggatc aagagctacc aactcttttt ccgaaggtaa ctggcttcag    9000
cagagcgcag ataccaaata ctgtccttct agtgtagccg tagttaggcc accacttcaa    9060
gaactctgta gcaccgccta catacctcgc tctgctaatc ctgttaccag tggctgctgc    9120
cagtggcgat aagtcgtgtc ttaccgggtt ggactcaaga cgatagttac cggataaggc    9180
gcagcggtcg ggctgaacgg ggggttcgtg cacacagccc agcttggagc gaacgaccta    9240
caccgaactg agatacctac agcgtgagct atgagaaagc gccacgcttc ccgaagggag    9300
aaaggcggac aggtatccgg taagcggcag ggtcggaaca ggagagcgca cgagggagct    9360
tccaggggga aacgcctggt atctttatag tcctgtcggg tttcgccacc tctgacttga    9420
gcgtcgattt ttgtgatgct cgtcaggggg gcggagccta tggaaaaacg ccagcaacgc    9480
ggccttttta cggttcctgg ccttttgctg gccttttgct cacat                   9525
```

<210> SEQ ID NO 22
<211> LENGTH: 40
<212> TYPE: DNA
<213> ORGANISM: Artificial Sequence
<220> FEATURE:
<223> OTHER INFORMATION: Primer tw52

<400> SEQUENCE: 22
cacactaagg aggaaaaaaa ccatgccaat ggcgctttgg                          40

<210> SEQ ID NO 23
<211> LENGTH: 40
<212> TYPE: DNA
<213> ORGANISM: Artificial Sequence
<220> FEATURE:
<223> OTHER INFORMATION: Primer tw51

<400> SEQUENCE: 23
gcttaggcct gcagatatct agatcaaacg gcggcgattg                          40

<210> SEQ ID NO 24
<211> LENGTH: 8142
<212> TYPE: DNA
<213> ORGANISM: Artificial Sequence
<220> FEATURE:
<223> OTHER INFORMATION: pSGI-TW12

<400> SEQUENCE: 24

| | | | | | |
|---|---|---|---|---|---|
| gtctgacgct | cagtggaacg | aaaactcacg | ttaagggatt | ttggtcatga | gattatcaaa | 60 |
| aaggatcttc | acctagatcc | ttttaaatta | aaaatgaagt | tttaaatcaa | tctaaagtat | 120 |
| atatgagtaa | acttggtctg | acagttacca | atgcttaatc | agtgaggcac | ctatctcagc | 180 |
| gatctgtcta | tttcgttcat | ccatagttgc | ctgactcccc | gtcgtgtaga | taactacgat | 240 |
| acgggagggc | ttaccatctg | gccccagtgc | tgcaatgata | ccgcgagacc | cacgctcacc | 300 |
| ggctccagat | ttatcagcaa | taaaccagcc | agccggaagg | gccgagcgca | gaagtggtcc | 360 |
| tgcaacttta | tccgcctcca | tccagtctat | taattgttgc | cgggaagcta | gagtaagtag | 420 |
| ttcgccagtt | aatagtttgc | gcaactgttg | ggaagggcga | tcggtgcggg | cctcttcgct | 480 |
| attacgccag | ctggcgaaag | gggatgtgc | tgcaaggcga | ttaagttggg | taacgccagg | 540 |
| gttttcccag | tcacgacgtt | gtaaaacgac | ggccagtgaa | ttgggcccga | ctgcctttgg | 600 |
| tggtattacc | gatgagtggc | acgttatttt | caccgctctg | gccgtgttga | gcatggtgct | 660 |
| gggcaacgtg | gtggctttag | cccaaaccag | catgaaacgg | atgttggcct | actcttccat | 720 |
| cggtcaagca | ggctttgtga | tgattggcct | agtggccggc | agtgaagatg | gttacgccag | 780 |
| catggttttc | tacatgctca | tctatctgtt | tatgaacctg | ggggcgttta | gttgcattat | 840 |
| tctcttcacc | ctccgcactg | gcagtgacca | aattagtgat | tacgctggtc | tgtaccacaa | 900 |
| agaccccttg | ttaaccttgg | gcttgagcat | ttgtttatta | tccttggggg | gcattcctcc | 960 |
| tctggcgggc | ttttcggca | aaatttacat | cttctgggcc | ggttggcaat | cgggattgta | 1020 |
| tggcctagtc | ctacttggtc | tggttaccag | tgtagtttcc | atctactact | acatccgggt | 1080 |
| ggtgaaaatg | atggtggtga | aggagcccca | ggaaatgtcc | gaagtaatca | aaaattaccc | 1140 |
| ggccatcaaa | tggaatttac | ccggcatgcg | tcccctacag | gtgggcattg | tcgctacttt | 1200 |
| ggttgctacc | tcgctggcag | gtattctggc | taatcccctc | tttaacctcg | ccaccgattc | 1260 |
| cgtggtcagc | accaagatgt | tgcagacagc | cctccagcaa | acaggagaaa | ctccggcgat | 1320 |
| cgccatttcc | catgatttac | cctaggggta | tcaggaaata | ttgctttgca | ggcaaaagcc | 1380 |
| aatgagtgta | actatagaaa | ccgatttaaa | ggagatccac | tagtcctgag | gctgaaatga | 1440 |
| gctgttgaca | attaatcatc | cggctcgtat | aatgtgtgga | attgtgagcg | gataacaatt | 1500 |
| tcacactaag | gaggaaaaaa | accatgccaa | tggcgctttg | gggcatcgtt | ccatcaacc | 1560 |
| agtccagccc | gaccaggaga | gcatcaacca | tgggcatctt | taaccgccgc | cgactattgc | 1620 |
| tgggggagt | ggccctgggg | ggagcattca | ccataggccg | ggaggaacgc | catcgccagg | 1680 |
| aaatcaggga | attacaggca | ttagccaaag | cccaagcggc | caacaccgac | cgcaccagca | 1740 |
| tgttaaatgc | cgcctttgaa | gcggatgcgg | aaaaaattta | ccggggcgag | gaaattatta | 1800 |
| acagtgttag | gctcactccc | cctatcctgc | cctacgatcg | ccaaatttcc | caattgctga | 1860 |
| tccgttgcag | taaaatcgcc | acccagcaat | acttaactgg | gaaaaccatc | cctagctacg | 1920 |
| acggcaatat | tcgccagtta | ccggcctata | gctccgacct | ggatgagtat | aaacaaattg | 1980 |
| cttctttcg | cggtagggaa | gctcacattt | ccgaatccgt | tgcggtgcaa | attccctgg | 2040 |
| ataataccgg | tgacccctta | gataaaacct | gggaccaagc | ggaagattcc | ctgggggaaa | 2100 |

```
ccattcgtca agtggtcaaa gtaacccagg aaatccccgt ttacctgggt tttatcctca    2160
gttctccccg ccgcaatctc attgttttc ggggtaccca aaccaccatg aatgggtca     2220
ataatctccg ggcccaacaa attcccttca ccgaacggcg atcggggcaa tattttggca    2280
aaattcacca gggctttatc gaaaattatc tccgtattgt cagtcccatt ccgagggaaa    2340
ttgcccagca gttagacccg gccgtgccct gttacgtcac tggccatagt ttgggggctt    2400
ccctggcggt gctggcggcg ttggatctag cggttaacct ccccaactta cggtcccaga    2460
ttcaacttta tagctatgcc tgccccaggg tcggcgatgt gacctttgcc caactccatt    2520
cccgccaagt gcccaacagt taccgtattg ttaacctcgc agacgtgatt cccctcctgc    2580
cccccactac ggggttaggc acctatgtcc atgtcgggca aagttggagt ttcctcagcc    2640
aaggagggga catcttaccc aaccatgtgg tggataccta ccagggagca gtggataggg    2700
aagtggaaac ggatcagtcc agagattatc caatcgccgc cgtttgatct agatatctgc    2760
aggcctaagc tttatgcttg taaaccgttt tgtgaaaaaa tttttaaaat aaaaaagggg    2820
acctctaggg tccccaatta attagtaata taatctatta aaggtcattc aaaaggtcat    2880
ccaccggatc aattcccctg ctcgcgcagg ctgggtgcca ggcccgatcc ttggagccct    2940
tgccctcccg cacgatgatc gtgccgtgat cgaaatccag atccttgacc cgcagttgca    3000
aaccctcact gatccgcatg cccgttccat acagaagctg ggcgaacaaa cgatgctcgc    3060
cttccagaaa accgaggatg cgaaccactt catccgggt cagcaccacc ggcaagcgcc    3120
gcgacggccg aggtcttccg atctcctgaa gccagggcag atccgtgcac agcaccttgc    3180
cgtagaagaa cagcaaggcc gccaatgcct gacgatgcgt ggagaccgaa accttgcgct    3240
cgttcgccag ccaggacaga aatgcctcga cttcgctgct gcccaaggtt gccgggtgac    3300
gcacaccgtg gaaacggatg aaggcacgaa cccagtggac ataagcctgt tcggttcgta    3360
agctgtaatg caagtagcgt atgcgctcac gcaactggtc cagaaccttg accgaacgca    3420
gcggtggtaa cggcgcagtg gcggttttca tggcttgtta tgactgtttt tttgggtac    3480
agtctatgcc tcggtcgggc atccaagcag caagcgcgtt acgccgtggg tcgatgtttg    3540
atgttatgga gcagcaacga tgttacgcag cagggcagtc gccctaaaac aaagttaaac    3600
atcatgaggg aagcggtgat cgccgaagta tcgactcaac tatcagaggt agttggcgtc    3660
atcgagcgcc atctcgaacc gacgttgctg gccgtacatt tgtacggctc cgcagtggat    3720
ggcggcctga agccacacag tgatattgat ttgctggtta cggtgaccgt aaggcttgat    3780
gaaacaacgc ggcgagcttt gatcaacgac cttttgaaa cttcggcttc ccctggagag    3840
agcgagattc tccgcgctgt agaagtcacc attgttgtgc acgacgacat cattccgtgg    3900
cgttatccag ctaagcgcga actgcaattt ggagaatggc agcgcaatga cattcttgca    3960
ggtatcttcg agccagccac gatcgacatt gatctggcta tcttgctgac aaaagcaaga    4020
gaacatagcg ttgccttggt aggtccagcg cggaggaac tctttgatcc ggttcctgaa    4080
caggatctat ttgaggcgct aaatgaaacc ttaacgctat ggaactcgcc gcccgactgg    4140
gctggcgatg agcgaaatgt agtgcttacg ttgtcccgca tttggtacag cgcagtaacc    4200
ggcaaaatcg cgccgaagga tgtcgctgcc gactgggcaa tggagcgcct gccggcccag    4260
tatcagcccg tcatacttga agctagacag gcttatcttg acaagaaga agatcgcttg    4320
gcctcgcgcg cagatcagtt ggaagaattt gtccactacg tgaaaggcga gatcaccaag    4380
gtagtcggca aataatgtct aacaattcgt tcaagccgac gccgcttcgc ggcgcggctt    4440
aactcaagcg ttagatgcac taagcacata attgctcaca gccaaactat caggtcaagt    4500
```

```
ctgcttttat tattttaag cgtgcataat aagccctaca caaattggga gatatatcat    4560
gaaaggctgg cttttcttg ttatcgcaat agttggcgaa gtaatcgcaa catccgcatt    4620
aaaatctagc gagggcttta ctaagctgat ccggtggatg accttttgaa tgacctttaa    4680
tagattatat tactaattaa ttggggaccc tagaggtccc ctttttatt ttaaaaattt    4740
tttcacaaaa cggtttacaa gcataaagct tccgcggtac ccgggaattc gcccttcaa    4800
gcttcagatc aattcgcgct aacttacatt aattgcgttg cgctcactgc ccgctttcca    4860
gtcgggaaac ctgtcgtgcc agctgcatta atgaatcggc caacgcgcgg ggagaggcgg    4920
tttgcgtatt gggcgccagg gtggttttc ttttcaccag tgagacgggc aacagctgat    4980
tgcccttcac cgcctggccc tgagagagtt gcagcaagcg gtccacgctg gtttgcccca    5040
gcaggcgaaa atcctgtttg atggtggtta acggcgggat ataacatgag ctgtcttcgg    5100
tatcgtcgta tcccactacc gagatatccg caccaacgcg cagcccggac tcggtaatgg    5160
cgcgcattgc gcccagcgcc atctgatcgt tggcaaccag catcgcagtg gaacgatgc    5220
cctcattcag catttgcatg gtttgttgaa aaccggacat ggcactccag tcgccttccc    5280
gttccgctat cggctgaatt tgattgcgag tgagatattt atgccagcca gccagacgca    5340
gacgcgccga gacagaactt aatgggcccg ctaacagcgc gatttgctgg tgacccaatg    5400
cgaccagatg ctccacgccc agtcgcgtac cgtcttcatg ggagaaaata atactgttga    5460
tgggtgtctg gtcagagaca tcaagaaata cgccggaac attagtgcag gcagcttcca    5520
cagcaatggc atcctggtca tccagcggat agttaatgat cagcccactg acgcgttgcg    5580
cgagaagatt gtgcaccgcc gctttacagg cttcgacgcc gcttcgttct accatcgaca    5640
ccaccacgct ggcacccagt tgatcggcgc gagatttaat cgccgcgaca atttgcgacg    5700
gcgcgtgcag ggccagactg gaggtggcaa cgccaatcag caacgactgt ttgcccgcca    5760
gttgttgtgc cacgcggttg ggaatgtaat tcagctccgc catcgccgct tccactttt    5820
cccgcgtttt cgcagaaacg tggctggcct ggttcaccac gcgggaaacg tctgataag    5880
agacaccggc atactctgcg acatcgtata acgttactgg tttcacattc accaccctga    5940
attgactctc ttccgggcgc tatcatgcca taccgcgaaa ggttttgcac cattcgatgg    6000
tgtcaacgta atgcatgcc gcttcgcctt cgcgcaagct tagaagggcg aattccggac    6060
atatggatct tggggaaat taagaccaaa ctcgatgacc tccaaaaaga tgtaacttct    6120
cttaagatcg atatggcaac ggtgaaaacc gagttatctg cggtcaggat ggagataggt    6180
acagtcaagg atgatgttaa agatgtcaaa gggcgggcta atgctcaaat ttgggcgttg    6240
attcttgccg tcatcggagc cataattacc accttggtgc gttttggcat tttccctaat    6300
ccctaacaaa aaagcgacca ggcttttctt tcaattgccc gatcgccttt gatatttcc    6360
caaaggataa aagctagtcc attcagaatc gagccttaaa gtactcccat attggctagc    6420
cccagaatta ctccagcgcc gaggatgtgg ccaaagctag cggtgcccag cacagcccct    6480
aaaccaaagc cgccaaagaa gttagaggaa ggcatggggg tgcccacatt ttgttgtttg    6540
atggtcaatt taccaaaggc gatcgccaaa atgttgcaag caatcatcac cccagcaact    6600
ttagggctcc aggacagggt ggcgggaacg gcggtggcca acaaaaagct atgcattgag    6660
attctccaga ataaagacgg ttttaaagg gatagcccca cgctaatggg ggtctttaaa    6720
aatctcatct tacggggacg ctctgcccct gggaaaccac cgttgcaata cttaacaaat    6780
tttcgttttt agcttggcaa atgtcttttgg caaaattggt tgatctggct taaatcgtca    6840
```

-continued

```
gttatttgcc ctggaatagt ctggggacgg gcaattctga tcagatttac ccccaacgct    6900
tccgccactt tttgcttaac caattctccc ccctgggcac cggaggcttt agttaccacc    6960
ccttgaattt gccattgttg ccacagggct ttttccaatg gttcggctac ggggggggcgc   7020 aaagcaatga tacggtcgga agtaaaccca gcggcgatcg cctgggctag gcttggggga    7080
tagggcagaa tacgggcaaa tagggcccag cttggcgtaa tcatggtcat agctgtttcc    7140
tgtgtgaaat tgttatccgc tcacaattcc acacaacata cgagccggaa gcataaagtg    7200
taaagcctgg ggtgcctaat gagtgagcta actcacatta attgcgttgc gctcactgcc    7260
cgctttccag tcgggaaacc tgtcgtgcca gctgcattaa tgaatcggcc aacgcgcggg    7320
gagaggcggt ttgcgtattg ggcgctcttc cgcttcctcg ctcactgact cgctgcgctc    7380
ggtcgttcgg ctgcggcgag cggtatcagc tcactcaaag gcggtaatac ggttatccac    7440
agaatcaggg gataacgcag gaaagaacat gtgagcaaaa ggccagcaaa aggccaggaa    7500
ccgtaaaaag gccgcgttgc tggcgttttt ccataggctc cgcccccctg acgagcatca    7560
caaaaatcga cgctcaagtc agaggtggcg aaacccgaca ggactataaa gataccaggc    7620
gtttccccct ggaagctccc tcgtgcgctc tcctgttccg accctgccgc ttaccggata    7680
cctgtccgcc tttctccctt cgggaagcgt ggcgctttct catagctcac gctgtaggta    7740
tctcagttcg gtgtaggtcg ttcgctccaa gctgggctgt gtgcacgaac cccccgttca    7800
gcccgaccgc tgcgccttat ccggtaacta tcgtcttgag tccaacccgg taagacacga    7860
cttatcgcca ctggcagcag ccactggtaa caggattagc agagcgaggt atgtaggcgg    7920
tgctacagag ttcttgaagt ggtggcctaa ctacggctac actagaagga cagtatttgg    7980
tatctgcgct ctgctgaagc cagttacctt cggaaaaaga gttggtagct cttgatccgg    8040
caaacaaacc accgctggta gcggtggttt ttttgtttgc aagcagcaga ttacgcgcag    8100
aaaaaaagga tctcaagaag atcctttgat cttttctacg gg                      8142
```

<210> SEQ ID NO 25
<211> LENGTH: 31
<212> TYPE: DNA
<213> ORGANISM: Artificial Sequence
<220> FEATURE:
<223> OTHER INFORMATION: Primer RS2-5

<400> SEQUENCE: 25

```
gggccctatt tgcccgtatt ctgccctatc c                                    31
```

<210> SEQ ID NO 26
<211> LENGTH: 32
<212> TYPE: DNA
<213> ORGANISM: Artificial Sequence
<220> FEATURE:
<223> OTHER INFORMATION: Primer RS2-3

<400> SEQUENCE: 26

```
gggcccgact gcctttggtg gtattaccga tg                                   32
```

<210> SEQ ID NO 27
<211> LENGTH: 25
<212> TYPE: DNA
<213> ORGANISM: Artificial Sequence
<220> FEATURE:
<223> OTHER INFORMATION: primer NB001

<400> SEQUENCE: 27

```
ctcgagcccc cgtgctatga ctagc                                           25
```

<210> SEQ ID NO 28
<211> LENGTH: 28
<212> TYPE: DNA
<213> ORGANISM: Artificial Sequence
<220> FEATURE:
<223> OTHER INFORMATION: primer NB002

<400> SEQUENCE: 28
ctcgagcccg gaacgttttt tgtacccc                                    28

<210> SEQ ID NO 29
<211> LENGTH: 29
<212> TYPE: DNA
<213> ORGANISM: Artificial Sequence
<220> FEATURE:
<223> OTHER INFORMATION: primer NB010

<400> SEQUENCE: 29
caattggtca cacgggataa taccgcgcc                                   29

<210> SEQ ID NO 30
<211> LENGTH: 36
<212> TYPE: DNA
<213> ORGANISM: Artificial Sequence
<220> FEATURE:
<223> OTHER INFORMATION: primer NB011

<400> SEQUENCE: 30
caattggtcg atcatatcgt caattattac ctccac                           36

<210> SEQ ID NO 31
<211> LENGTH: 7224
<212> TYPE: DNA
<213> ORGANISM: Artificial Sequence
<220> FEATURE:
<223> OTHER INFORMATION: pSGI-NB5

<400> SEQUENCE: 31
cccccgtgct atgactagcg gcgatcgcca taccggccac gaccatttgc attggatccc    60
caacggcggc cacaacttcc atggcattga gatgcgggga atgatgttct agactctgac   120
gcaccaaagc caattttgt tgatggttgc aatggggatg actactgttc actttgcccc    180
cagcgtcaat gcctagacct agcagtaccc ccagggctgt ggtagtgccc ccaccacgc    240 attcgcttag cactaagtaa ctttcggcat gttcctgggc taactgtgcg ccccactgca    300
aaccctgctg aaaaagatgc tccaccaggg ccaacgtaa cgcttgccct gtggaaagac    360
agcgggcggg ttgtccgtct agattgatga ctggcaccgc tgggggaatg ggtaaaccag    420
agttaaataa ataaaccgga gtatggaggg catccaccaa cgctttggtg atgaacactg    480
gggaaacccc agaaatgagg ggaggtaagg ataggttgc ccctgccgta gttcccttga    540
ttaaaaattc cgcatcggcg atcgccgtca attttcgatc agcggggtt ttacccgccg    600 cagaaatgcc cggaattaaa ccagtttccg taaagcccaa cacacagaca aacaccggtg    660
gacagtggcc atggcgctca atccaggata aagcttggtc agactgggta taaactgtca    720
acatatttct gcaagagtgg gcccaattgg gaaaatcaac ctcaaatcca ttggaatagc    780
cttttttcaa ccgtaaaaat ccaactttct ctcttccctt cttccttcca tctgattatg    840
gttacgccaa ttaactacca ttccatccat tgcctggcgg atatctgggc tatcaccgga    900
gaaaattttg ccgatattgt ggccctcaac gatcgccata gtcatccccc cgtaacttta    960

```
acctatgccc aattggtcac acgggataat accgcgccac atagcagaac tttaaaagtg    1020
ctcatcattg gaaaacgttc ttcggggcga aaactctcaa ggatcttacc gctgttgaga    1080
tccagttcga tgtaacccac tcgtgcaccc aactgatctt cagcatcttt tactttcacc    1140
agcgtttctg ggtgagcaaa aacaggaagg caaaatgccg caaaaaaggg aataagggcg    1200
acacggaaat gttgaatact catactcttc cttttcaat attattgaag catttatcag     1260
ggttattgtc tcatgagcgg atacatattt gaatgtattt agaaaaataa acaaataggg    1320
gttccgcgca catttccccg aaaagtgcca cctgacgtct aagaaaccat tattatcatg    1380
acattaacct ataaaaatag gcgtatcacg aggccctttc gtcttcgaat aaatacctgt    1440
gacggaagat cacttcgcag aataaataaa tcctggtgtc cctgttgata ccgggaagcc    1500
ctgggccaac ttttggcgaa aatgagacgt tgatcggcac gtaagaggtt ccaactttca    1560
ccataatgaa ataagatcac taccgggcgt attttttgag ttatcgagat tttcaggagc    1620
taaggaagct aaaatggaga aaaaaatcac tggatatacc accgttgata tatcccaatg    1680
gcatcgtaaa gaacattttg aggcatttca gtcagttgct caatgtacct ataaccagac    1740
cgttcagctg gatattacgg cctttttaaa gaccgtaaag aaaaataagc acaagtttta    1800
tccggccttt attcacattc ttgcccgcct gatgaatgct catccggaat tccgtatggc    1860
aatgaaagac ggtgagctgg tgatatggga tagtgttcac ccttgttaca ccgttttcca    1920
tgagcaaact gaaacgtttt catcgctctg gagtgaatac cacgacgatt tccggcagtt    1980
tctacacata tattcgcaag atgtggcgtg ttacggtgaa aacctggcct atttccctaa    2040
agggtttatt gagaatatgt ttttcgtctc agccaatccc tgggtgagtt tcaccagttt    2100
tgatttaaac gtggccaata tggacaactt cttcgcccc gttttcacca tgggcaaata    2160
ttatacgcaa ggcgacaagg tgctgatgcc gctggcgatt caggttcatc atgccgtttg    2220
tgatggcttc catgtcggca gaatgcttaa tgaattacaa cagtactgcg atgagtggca    2280
gggcggggcg taatttttt aaggcagtta ttggtgccct aaacgcctg gtgctacgcc     2340 tgaataagtg ataataagcg gatgaatggc agaaattcga aagcaaattc gacccggtcg    2400
tcggttcagg gcagggtcgt taaatagccg cttatgtcta ttgctggttt accggtttat    2460
tgactaccgg aagcagtgtg accgtgtgct tctcaaatgc ctgaggccag tttgctcagg    2520 ctctcccgt ggaggtaata attgacgata tgatcgacca attgcgggaa gaaattacag     2580
cttttgccgc tggcctacag agtttaggag ttaccccca tcaacacctg gccattttcg     2640
ccgacaacag ccccggtgg tttatcgccg atcaaggcag tatgttggct ggagccgtca     2700
acgccgtccg ttctgcccaa gcagagcgcc aggaattact ctacatccta gaagacagca    2760
acagccgtac tttaatcgca gaaaatcggc aaaccctaag caaattggcc ctagatggcg    2820
aaaccattga cctgaaacta atcatcctcc tcaccgatga agaagtggca gaggacagcg    2880
ccattcccca atataacttt gcccaggtca tggccctagg ggccggcaaa atccccactc    2940
ccgttccccg ccaggaagaa gatttagcca ccctgatcta cacctccggc accacaggac    3000
aacccaaagg ggtgatgctc agccacggta atttattgca ccaagtacgg gaattggatt    3060
cggtgattat tccccgcccc ggcgatcagg tgttgagcat tttgccctgt tggcactccc    3120
tagaaagaag cgccgaatat tttcttcttt cccggggctg cacgatgaac tacaccagca    3180
ttcgccattt caaggggat gtgaaggaca ttaaacccca tcacattgtc ggtgtgcccc      3240
ggctgtggga atccctctac gaaggggtac aaaaaacgtt ccgggctaag gcgaattct     3300 gcagatatcc atcacactgg cggccgctcg agcatgcatc tagagggccc aattcgccct    3360
```

```
atagtgagtc gtattacaat tcactggccg tcgttttaca acgtcgtgac tgggaaaacc    3420
ctggcgttac ccaacttaat cgccttgcag cacatcccc tttcgccagc tggcgtaata    3480
gcgaagaggc ccgcaccgat cgcccttccc aacagttgcg cagcctgaat ggcgaatgga    3540
cgcgccctgt agcggcgcat taagcgcggc gggtgtggtg gttacgcgca gcgtgaccgc    3600
tacacttgcc agcgccctag cgcccgctcc tttcgctttc ttcccttcct ttctcgccac    3660
gttcgccggc tttccccgtc aagctctaaa tcggggggctc cctttagggt tccgatttag    3720
tgctttacgg cacctcgacc ccaaaaaact tgattagggt gatggttcac gtagtgggcc    3780
atcgccctga tagacggttt ttcgcccttt gacgttggag tccacgttct ttaatagtgg    3840
actcttgttc caaactggaa caacactcaa ccctatctcg gtctattctt ttgatttata    3900
agggattttg ccgatttcgg cctattggtt aaaaaatgag ctgatttaac aaaaatttaa    3960
cgcgaatttt aacaaaattc agggcgcaag gctgctaaa ggaagcggaa cacgtagaaa    4020
gccagtccgc agaaacggtg ctgacccccgg atgaatgtca gctactgggc tatctggaca    4080
agggaaaacg caagcgcaaa gagaaagcag gtagcttgca gtgggcttac atggcgatag    4140
ctagactggg cggttttatg gacagcaagc gaaccggaat tgccagctgg ggcgccctct    4200
ggtaaggttg ggaagccctg caaagtaaac tggatggctt tcttgccgcc aaggatctga    4260
tggcgcaggg gatcaagatc tgatcaagag acaggatgag gatcgtttcg catgattgaa    4320
caagatggat tgcacgcagg ttctccggcc gcttgggtgg agaggctatt cggctatgac    4380
tgggcacaac agacaatcgg ctgctctgat gccgccgtgt tccggctgtc agcgcagggg    4440
cgcccggttc ttttttgtcaa gaccgacctg tccggtgccc tgaatgaact gcaggacgag    4500
gcagcgcggc tatcgtggct ggccacgacg ggcgttcctt gcgcagctgt gctcgacgtt    4560
gtcactgaag cgggaaggga ctggctgcta ttgggcgaag tgccggggca ggatctcctg    4620
tcatcccacc ttgctcctgc cgagaaagta tccatcatgg ctgatgcaat gcggcggctg    4680
catacgcttg atccggctac ctgcccattc gaccaccaag cgaaacatcg catcgagcga    4740
gcacgtactc ggatggaagc cggtcttgtc gatcaggatg atctggacga agagcatcag    4800
gggctcgcgc cagccgaact gttcgccagg ctcaaggcgc gcatgcccga cggcgaggat    4860
ctcgtcgtga cccatggcga tgcctgcttg ccgaatatca tggtggaaaa tggccgcttt    4920
tctggattca tcgactgtgg ccggctgggt gtggcggacc gctatcagga catagcgttg    4980
gctacccgtg atattgctga agagcttggc ggcgaatggg ctgaccgctt cctcgtgctt    5040
tacggtatcg ccgctcccga ttcgcagcgc atcgccttct atcgccttct tgacgagttc    5100
ttctgaattg aaaaaggaag agtatgagta ttcaacattt ccgtgtcgcc cttattccct    5160
ttttttgcggc attttgcctt cctgttttttg ctcacccaga aacgctggtg aaagtaaaag    5220
atgctgaaga tcagttgggt gcacgagtgg gttacatcga actggatctc aacagcggta    5280
agatccttga gagttttcgc cccgaagaac gttttccaat gatgagcact tttaaagttc    5340
tgctatgtgg cgcggtatta tcccgtattg acgccgggca agagcaactc ggtcgccgca    5400
tacactattc tcagaatgac ttggttgagt actcaccagt cacagaaaag catcttacgg    5460
atggcatgac agtaagagaa ttatgcagtg ctgccataac catgagtgat aacactgcgg    5520
ccaacttact tctgacaacg atcggaggac cgaaggagct aaccgctttt ttgcacaaca    5580
tgggggatca tgtaactcgc cttgatcgtt gggaaccgga gctgaatgaa gccataccaa    5640
acgacgagcg tgacaccacg atgcctgtag caatggcaac aacgttgcgc aaactattaa    5700
```

```
ctggcgaact acttactcta gcttcccggc aacaattaat agactggatg gaggcggata    5760
aagttgcagg accacttctg cgctcggccc ttccggctgg ctggtttatt gctgataaat    5820
ctggagccgg tgagcgtggg tctcgcggta tcattgcagc actggggcca gatggtaagc    5880
cctcccgtat cgtagttatc tacacgacgg ggagtcaggc aactatggat gaacgaaata    5940
gacagatcgc tgagataggt gcctcactga ttaagcattg gtaactgtca gaccaagttt    6000
actcatatat actttagatt gatttaaaac ttcattttta atttaaaagg atctaggtga    6060
agatcctttt tgataatctc atgaccaaaa tcccttaacg tgagttttcg ttccactgag    6120
cgtcagaccc cgtagaaaag atcaaaggat cttcttgaga tcctttttt ctgcgcgtaa    6180 tctgctgctt gcaaacaaaa aaaccaccgc taccagcggt ggtttgtttg ccggatcaag    6240
agctaccaac tcttttccg aaggtaactg gcttcagcag agcgcagata ccaaatactg    6300
ttcttctagt gtagccgtag ttaggccacc acttcaagaa ctctgtagca ccgcctacat    6360
acctcgctct gctaatcctg ttaccagtgg ctgctgccag tggcgataag tcgtgtctta    6420
ccgggttgga ctcaagacga tagttaccgg ataaggcgca gcggtcgggc tgaacggggg    6480
gttcgtgcac acagcccagc ttggagcgaa cgacctacac cgaactgaga tacctacagc    6540
gtgagctatg agaaagcgcc acgcttcccg aagggagaaa ggcggacagg tatccggtaa    6600
gcggcagggt cggaacagga gagcgcacga gggagcttcc agggggaaac gcctggtatc    6660
tttatagtcc tgtcgggttt cgccacctct gacttgagcg tcgattttg tgatgctcgt    6720 caggggggcg gagcctatgg aaaaacgcca gcaacgcggc cttttacgg ttcctggcct    6780 tttgctggcc ttttgctcac atgttctttc ctgcgttatc ccctgattct gtggataacc    6840
gtattaccgc ctttgagtga gctgataccg ctcgccgcag ccgaacgacc gagcgcagcg    6900
agtcagtgag cgaggaagcg gaagagcgcc caatacgcaa accgcctctc cccgcgcgtt    6960
ggccgattca ttaatgcagc tggcacgaca ggtttcccga ctggaaagcg ggcagtgagc    7020
gcaacgcaat taatgtgagt tagctcactc attaggcacc ccaggcttta cactttatgc    7080
ttccggctcg tatgttgtgt ggaattgtga gcggataaca atttcacaca ggaaacagct    7140
atgaccatga ttacgccaag cttggtaccg agctcggatc cactagtaac ggccgccagt    7200
gtgctggaat tcgcccttct cgag                                          7224

<210> SEQ ID NO 32
<211> LENGTH: 989
<212> TYPE: DNA
<213> ORGANISM: Synechocystis sp. PCC6803 RS1 up

<400> SEQUENCE: 32
attgctgaag cggaatccct ggttaatgcc gccgccgatg ccaattgcat tctccaagtg      60
gggcacattg aacgcttcaa cccggcattt ttagagctaa ccaaaattct caaaacggaa     120
gagttattgg cgatcgaagc ccatcgcatg agtccctatt cccagcgggc caatgatgtc     180
tccgtggtat tggatttgat gatccatgac attgacctgt tgctggaatt ggtgggttcg     240
gaagtggtta aactgtccgc cagtggcagt cgggcttctg ggtcaggata tttggattat     300
gtcaccgcta cgttaggctt ctcctccggc attgtggcca cctcaccgc cagtaaggtc     360 acccatcgta aaattcgttc catcgccgcc cactgcaaaa attccctcac cgaagcggat     420
tttctcaata cgaaattttt gatccatcgc caaccaccg ctgattggag cgcggactat     480
ggccaggtat tgtatcgcca ggatggtcta atcgaaaagg tttacaccag taatattgaa     540
cctctccacg ctgaattaga acatttatt cattgtgtta ggggaggtga tcaaccctca     600
```

```
gtgggggggag aacaggccct caaggccctg aagttagcca gtttaattga agaaatggcc    660
ctggacagtc aggaatggca tggggggaa gttgtgacag aatatcaaga tgccaccctg    720
gccctcagtg cgagtgttta aatcaactta attaatgcaa ttattgcgag ttcaaactcg    780
ataactttgt gaaatattac tgttgaatta atctatgact attcaataca ccccctagc    840 cgatcgcctg ttggcctacc tcgccgccga tcgcctaaat ctcagcgcca agagtagttc    900
cctcaacacc agtattctgc tcagcagtga cctattcaat caggaagggg gaattgtaac    960
agccaactat ggctttgatg gttatatgg                                      989

<210> SEQ ID NO 33
<211> LENGTH: 989
<212> TYPE: DNA
<213> ORGANISM: Synechocystis sp. PCC6803 RS1 down

<400> SEQUENCE: 33
ccggtatgga tggcaccgat gcggaatccc aacagattgc ctttgacaac aatgtggcct     60
ggaataacct gggggatttg tccaccacca cccaacgggc ctacacttcg gctattagca    120
cagacacagt gcagagtgtt tatggcgtta atctggaaaa aaacgataac attcccattg    180
tttttgcgtg gcccattttt cccaccaccc ttaatcccac agattttcag gtaatgctta    240
acacggggga aattgtcacc ccggtgatcg cctctttgat tcccaacagt gaatacaacg    300
aacggcaaac ggtagtaatt acgggcaatt ttggtaatcg tttaacccca ggcacggagg    360
gagcgattta tcccgtttcc gtaggcacag tgttggacag tactcctttg gaaatggtgg    420
gacccaacgg cccggtcagt gcggtgggta ttaccattga tagtctcaac ccctacgtgg    480
ccggcaatgg tcccaaaatt gtcgccgcta agttagaccg cttcagtgac ctgggggaag    540
gggctcccct ctggttagcc accaatcaaa ataacagtgg cggggattta tatggagacc    600
aagcccaatt tcgtttgcga atttacacca gcgccggttt ttcccccgat ggcattgcca    660
gtttactacc cacagaattt gaacggtatt ttcaactcca agcggaagat attacgggac    720
ggacagttat cctaacccaa actggtgttg attatgaaat tcccggcttt ggtctggtgc    780
aggtgttggg gctggcggat ttggccgggg ttcaggacag ctatgacctg acttacatcg    840
aagatcatga caactattac gacattatcc tcaaggggga cgaagccgca gttcgccaaa    900
ttaagagggt tgctttgccc tccgaagggg attattcggc ggtttataat cccggtggcc    960
ccggcaatga tccagagaat ggtccccca                                      989

<210> SEQ ID NO 34
<211> LENGTH: 1032
<212> TYPE: DNA
<213> ORGANISM: Synechocystis sp. PCC6803 RS2 up

<400> SEQUENCE: 34
tatttgcccg tattctgccc tatccccaag ccctagccca ggcgatcgcc gctgggttta     60
cttccgaccg tatcattgct ttgcgccccc ccgtagccga accattggaa aaagccctgt    120
ggcaacaatg gcaaattcaa ggggtggtaa ctaaagcctc cggtgcccag gggggagaat    180
tggttaagca aaaagtggcg gaagcgttgg gggtaaatct gatcagaatt gcccgtcccc    240
agactattcc agggcaaata actgacgatt taagccagat caaccaattt gccaaagac    300 atttgccaag ctaaaaacga aaatttgtta agtattgcaa cggtggtttc ccaggggcag    360
agcgtccccg taagatgaga ttttaaaga ccccccattag cgtggggcta tcccttttaaa    420
```

```
aaccgtcttt attctggaga atctcaatgc atagcttttt gttggccacc gccgttcccg    480
ccaccctgtc ctggagccct aaagttgctg gggtgatgat tgcttgcaac attttggcga    540
tcgcctttgg taaattgacc atcaaacaac aaaatgtggg cacccccatg ccttcctcta    600
acttctttgg cggctttggt ttaggggctg tgctgggcac cgctagcttt ggccacatcc    660
tcggcgctgg agtaattctg gggctagcca atatgggagt actttaaggc tcgattctga    720
atggactagc ttttatcctt tgggaaaata tcaaaggcga tcgggcaatt gaaagaaaag    780
cctggtcgct ttttgttag ggattaggga aaatgccaaa acgcaccaag gtggtaatta    840
tggctccgat gacggcaaga atcaacgccc aaatttgagc attagcccgc cctttgacat    900 cctttaacatc atccttgact gtacctatct ccatcctgac cgcagataac tcggttttca    960
ccgttgccat atcgatctta agagaagtta catcttttg gaggtcatcg agtttggtct   1020
taatttcccc ca                                                      1032

<210> SEQ ID NO 35
<211> LENGTH: 824
<212> TYPE: DNA
<213> ORGANISM: Synechocystis sp. PCC6803 RS2 down

<400> SEQUENCE: 35
cctttaaatc ggtttctata gttacactca ttggcttttg cctgcaaagc aatatttcct     60
gataccccta gggtaaatca tgggaaatgg cgatcgccgg agtttctcct gtttgctgga    120
gggctgtctg caacatcttg gtgctgacca cggaatcggt ggcgaggtta agaggggat    180 tagccagaat acctgccagc gaggtagcaa ccaaagtagc gacaatgccc acctgtaggg    240
gacgcatgcc gggtaaattc catttgatgg ccgggtaatt tttgattact cggacattt     300 cctggggctc cttcaccacc atcattttca ccacccggat gtagtagtag atggaaacta    360
cactggtaac cagaccaagt aggactaggc catacaatcc cgattgccaa ccggcccaga    420
agatgtaaat tttgccgaaa aagcccgcca gaggaggaat gccccccaag gataataaac    480
aaatgctcaa gcccaaggtt aacaaggggt ctttgtggta cagaccagcg taatcactaa    540
tttggtcact gccagtgcgg agggtgaaga gaataatgca actaaacgcc cccaggttca    600
taaacagata gatgagcatg tagaaaaacca tgctggcgta accatcttca ctgccggcca    660
ctaggccaat catcacaaag cctgcttgac cgatggaaga gtaggccaac atccgtttca    720
tgctggtttg ggctaaagcc accacgttgc ccagcaccat gctcaacacg ccagagcgg    780 tgaaaataac gtgccactca tcggtaatac caccaaaggc agtc                   824

<210> SEQ ID NO 36
<211> LENGTH: 8572
<212> TYPE: DNA
<213> ORGANISM: Artificial Sequence
<220> FEATURE:
<223> OTHER INFORMATION: YC63 expression / integration vector

<400> SEQUENCE: 36
cagttaccaa tgcttaatca gtgaggcacc tatctcagcg atctgtctat ttcgttcatc     60
catagttgcc tgactccccg tcgtgtagat aactacgata cgggagggct taccatctgg    120
ccccagtgct gcaatgatac cgcgagaccc acgctcaccg gctccagatt tatcagcaat    180
aaaccagcca gccggaaggg ccgagcgcag aagtggtcct gcaactttat ccgcctccat    240
ccagtctatt aattgttgcc gggaagctag agtaagtagt tcgccagtta atagtttgcg    300
caactgttgg gaagggcgat cggtgcgggc ctcttcgcta ttacgccagc tggcgaaagg    360
```

-continued

```
gggatgtgct gcaaggcgat taagttgggt aacgccaggg ttttcccagt cacgacgttg    420
taaaacgacg gccagtgaat tgggcccgac tgcctttggt ggtattaccg atgagtggca    480
cgttattttc accgctctgg ccgtgttgag catggtgctg ggcaacgtgg tggctttagc    540
ccaaaccagc atgaaacgga tgttggccta ctcttccatc ggtcaagcag gctttgtgat    600
gattggccta gtggccggca gtgaagatgg ttacgccagc atggttttct acatgctcat    660
ctatctgttt atgaacctgg gggcgtttag ttgcattatt ctcttcaccc tccgcactgg    720
cagtgaccaa attagtgatt acgctggtct gtaccacaaa gaccccttgt taaccttggg    780
cttgagcatt tgtttattat ccttgggggg cattcctcct ctggcgggct ttttcggcaa    840
aatttacatc ttctgggccg gttggcaatc gggattgtat ggcctagtcc tacttggtct    900
ggttaccagt gtagtttcca tctactacta catccgggtg gtgaaaatga tggtggtgaa    960
ggagccccag gaaatgtccg aagtaatcaa aaattacccg gccatcaaat ggaatttacc   1020
cggcatgcgt cccctacagg tgggcattgt cgctactttg gttgctacct cgctggcagg   1080
tattctggct aatcccctct ttaacctcgc caccgattcc gtggtcagca ccaagatgtt   1140
gcagacagcc ctccagcaaa caggagaaac tccggcgatc gccatttccc atgatttacc   1200
ctaggggtat caggaaatat tgctttgcag gcaaaagcca atgagtgtaa ctatagaaac   1260
cgatttaaag gagatccact agtcctgagg ctgaaatgag ctgttgacaa ttaatcatcc   1320
ggctcgtata atgtgtggaa ttgtgagcgg ataacaattt cacactaagg aggaaaaaaa   1380
ccatggaaga cgccaaaaac ataaagaaag gcccggcgcc attctatccg ctggaagatg   1440
gaaccgctgg agagcaactg cataaggcta tgaagagata cgccctggtt cctggaacaa   1500
ttgcttttac agatgcacat atcgaggtgg acatcactta cgctgagtac ttcgaaatgt   1560
ccgttcggtt ggcagaagct atgaaacgat atgggctgaa tacaaatcac agaatcgtcg   1620
tatgcagtga aaactctctt caattcttta tgccggtgtt gggcgcgtta tttatcggag   1680
ttgcagttgc gcccgcgaac gacatttata atgaacgtga attgctcaac agtatgggca   1740
tttcgcagcc taccgtggtg ttcgtttcca aaaaggggtt gcaaaaaatt ttgaacgtgc   1800
aaaaaaagct cccaatcatc caaaaaatta ttatcatgga ttctaaaacg gattaccagg   1860
gatttcagtc gatgtacacg ttcgtcacat ctcatctacc tcccggtttt aatgaatacg   1920
attttgtgcc agagtccttc gatagggaca agacaattgc actgatcatg aactcctctg   1980
gatctactgg tctgcctaaa ggtgtcgctc tgcctcatag aactgcctgc gtgagattct   2040
cgcatgccag agatcctatt tttggcaatc aaatcattcc ggatactgcg attttaagtg   2100
ttgttccatt ccatcacggt tttggaatgt ttactacact cggatatttg atatgtggat   2160
ttcgagtcgt cttaatgtat agatttgaag aagagctgtt tctgaggagc cttcaggatt   2220
acaagattca aagtgcgctg ctggtgccaa ccctattctc cttcttcgcc aaaagcactc   2280
tgattgacaa atacgattta tctaatttac acgaaattgc ttctggtggc gctcccctct   2340
ctaaggaagt cggggaagcg gttgccaaga ggttccatct gccaggtatc aggcaaggat   2400
atgggctcac tgagactaca tcagctattc tgattacacc cgagggggat gataaaccgg   2460
gcgcggtcgg taaagttgtt ccattttttg aagcgaaggt tgtggatctg gataccggga   2520
aaacgctggg cgttaatcaa agaggcgaac tgtgtgtgag aggtcctatg attatgtccg   2580
gttatgtaaa caatccggaa gcgaccaacg ccttgattga caaggatgga tggctacatt   2640
ctggagacat agcttactgg gacgaagacg aacacttctt catcgttgac cgcctgaagt   2700
```

```
ctctgattaa gtacaaaggc tatcaggtgg ctcccgctga attggaatcc atcttgctcc    2760
aacaccccaa catcttcgac gcaggtgtcg caggtcttcc cgacgatgac gccggtgaac    2820
ttcccgccgc cgttgttgtt ttggagcacg gaaagacgat gacggaaaaa gagatcgtgg    2880
attacgtcgc cagtcaagta acaaccgcga aaaagttgcg cggaggagtt gtgtttgtgg    2940
acgaagtacc gaaaggtctt accggaaaac tcgacgcaag aaaaatcaga gagatcctca    3000
taaaggccaa aagggcgga aagatcgccg tgtaattcta gatatctgca ggcctaagct    3060
ttatgcttgt aaaccgtttt gtgaaaaaat ttttaaaata aaaaggggga cctctagggt    3120
ccccaattaa ttagtaatat aatctattaa aggtcattca aaaggtcatc caccggatca    3180
attccctgc tcgcgcaggc tgggtgccag gcccgatcct tggagcccct gccctcccgc    3240
acgatgatcg tgccgtgatc gaaatccaga tccttgaccc gcagttgcaa accctcactg    3300
atccgcatgc ccgttccata cagaagctgg gcgaacaaac gatgctcgcc ttccagaaaa    3360
ccgaggatgc gaaccacttc atccggggtc agcaccaccg gcaagcgccg cgacggccga    3420
ggtcttccga tctcctgaag ccagggcaga tccgtgcaca gcaccttgcc gtagaagaac    3480
agcaaggccg ccaatgcctg acgatgcgtg gagaccgaaa ccttgcgctc gttcgccagc    3540
caggacagaa atgcctcgac ttcgctgctg cccaaggttg ccgggtgacg cacaccgtgg    3600
aaacggatga aggcacgaac ccagtggaca taagcctgtt cggttcgtaa gctgtaatgc    3660
aagtagcgta tgcgctcacg caactggtcc agaaccttga ccgaacgcag cggtggtaac    3720
ggcgcagtgg cggttttcat ggcttgttat gactgttttt ttggggtaca gtctatgcct    3780
cggtcgggca tccaagcagc aagcgcgtta cgccgtgggt cgatgtttga tgttatggag    3840
cagcaacgat gttacgcagc agggcagtcg ccctaaaaca aagttaaaca tcatgaggga    3900
agcggtgatc gccgaagtat cgactcaact atcagaggta gttggcgtca tcgagcgcca    3960
tctcgaaccg acgttgctgg ccgtacattt gtacggctcc gcagtggatg gcggcctgaa    4020
gccacacagt gatattgatt tgctggttac ggtgaccgta aggcttgatg aaacaacgcg    4080
gcgagctttg atcaacgacc ttttggaaac ttcggcttcc cctggagaga gcgagattct    4140
ccgcgctgta gaagtcacca ttgttgtgca cgacgacatc attccgtggc gttatccagc    4200
taagcgcgaa ctgcaatttg gagaatggca gcgcaatgac attcttgcag gtatcttcga    4260
gccagccacg atcgacattg atctggctat cttgctgaca aaagcaagag aacatagcgt    4320
tgccttggta ggtccagcgg cggaggaact ctttgatccg gttcctgaac aggatctatt    4380
tgaggcgcta aatgaaaacct taacgctatg gaactcgccg cccgactggg ctggcgatga    4440
gcgaaatgta gtgcttacgt tgtcccgcat ttggtacagc gcagtaaccg gcaaaatcgc    4500
gccgaaggat gtcgctgccg actgggcaat ggagcgcctg ccggcccagt atcagcccgt    4560
catacttgaa gctagacagg cttatcttgg acaagaagaa gatcgcttgg cctcgcgcgc    4620
agatcagttg gaagaatttg tccactacgt gaaaggcgag atcaccaagg tagtcggcaa    4680
ataatgtcta acaattcgtt caagccgacg ccgcttcgcg gcgcggctta actcaagcgt    4740
tagatgcact aagcacataa ttgctcacag ccaaactatc aggtcaagtc tgcttttatt    4800
attttttaagc gtgcataata agccctacac aaattgggag atatatcatg aaaggctggc    4860
tttttcttgt tatcgcaata gttggcgaag taatcgcaac atccgcatta aaatctagcg    4920
agggctttac taagctgatc cggtggatga ccttttgaat gacctttaat agattatatt    4980
actaattaat tggggaccct agaggtcccc tttttattt taaaaatttt ttcacaaaac    5040
ggtttacaag cataaagctt ccgcggtacc cgggaattcg cccttcaag cttcagatca    5100
```

```
attcgcgcta acttacatta attgcgttgc gctcactgcc cgctttccag tcgggaaacc    5160
tgtcgtgcca gctgcattaa tgaatcggcc aacgcgcggg gagaggcggt ttgcgtattg    5220
ggcgccaggg tggttttttct tttcaccagt gagacgggca acagctgatt gcccttcacc    5280
gcctggccct gagagagttg cagcaagcgg tccacgctgg tttgccccag caggcgaaaa    5340
tcctgtttga tggtggttaa cggcgggata taacatgagc tgtcttcggt atcgtcgtat    5400
cccactaccg agatatccgc accaacgcgc agcccggact cggtaatggc gcgcattgcg    5460
cccagcgcca tctgatcgtt ggcaaccagc atcgcagtgg gaacgatgcc ctcattcagc    5520
atttgcatgg tttgttgaaa accggacatg gcactccagt cgccttcccg ttccgctatc    5580
ggctgaattt gattgcgagt gagatattta tgccagccag ccagacgcag acgcgccgag    5640
acagaactta atgggcccgc taacagcgcg atttgctggt gacccaatgc gaccagatgc    5700
tccacgccca gtcgcgtacc gtcttcatgg gagaaaataa tactgttgat gggtgtctgg    5760
tcagagacat caagaaataa cgccggaaca ttagtgcagg cagcttccac agcaatggca    5820
tcctggtcat ccagcggata gttaatgatc agcccactga cgcgttgcgc gagaagattg    5880
tgcaccgccg ctttacaggc ttcgacgccc ttcgttcta ccatcgacac caccacgctg    5940
gcacccagtt gatcggcgcg agatttaatc gccgcgacaa tttgcgacgg cgcgtgcagg    6000
gccagactgg aggtggcaac gccaatcagc aacgactgtt tgcccgccag ttgttgtgcc    6060
acgcggttgg gaatgtaatt cagctccgcc atcgccgctt ccactttttc ccgcgttttc    6120
gcagaaacgt ggctggcctg gttcaccacg cgggaaacgg tctgataaga gacaccggca    6180
tactctgcga catcgtataa cgttactggt ttcacattca ccaccctgaa ttgactctct    6240
tccgggcgct atcatgccat accgcgaaag gttttgcacc attcgatggt gtcaacgtaa    6300
atgcatgccg cttcgccttc gcgcaagctt agaagggcga attccggaca tatggatctt    6360
gggggaaatt aagaccaaac tcgatgacct ccaaaaagat gtaacttctc ttaagatcga    6420
tatggcaacg gtgaaaaccg agttatctgc ggtcaggatg gagataggta cagtcaagga    6480
tgatgttaaa gatgtcaaag ggcgggctaa tgctcaaatt tgggcgttga ttcttgccgt    6540
catcggagcc ataattacca ccttggtgcg ttttggcatt ttccctaatc cctaacaaaa    6600
aagcgaccag gcttttcttt caattgcccg atcgcctttg atattttccc aaaggataaa    6660
agctagtcca ttcagaatcg agccttaaag tactcccata ttggctagcc ccagaattac    6720
tccagcgccg aggatgtggc caaagctagc ggtgcccagc acagccccta aaccaaagcc    6780
gccaaagaag ttagaggaag gcatgggggt gcccacattt tgttgtttga tggtcaattt    6840
accaaaggcg atcgccaaaa tgttgcaagc aatcatcacc ccagcaactt tagggctcca    6900
ggacagggtg gcgggaacgg cggtggccaa caaaaagcta tgcattgaga ttctccagaa    6960
taaagacggt ttttaagggg atagccccac gctaatgggg gtctttaaaa atctcatctt    7020
acggggacgc tctgccctg ggaaccacc gttgcaatac ttaacaaatt ttcgttttta    7080
gcttggcaaa tgtctttggc aaaattggtt gatctggctt aaatcgtcag ttatttgccc    7140
tggaatagtc tggggacggg caattctgat cagatttacc cccaacgctt ccgccacttt    7200
ttgcttaacc aattctcccc cctgggcacc ggaggcttta gttaccaccc cttgaatttg    7260
ccattgttgc cacagggctt tttccaatgg ttcggctacg ggggggcgca aagcaatgat    7320
acggtcggaa gtaaacccag cggcgatcgc ctgggctagg gcttggggat agggcagaat    7380
acgggcaaat agggcccagc ttggcgtaat catggtcata gctgtttcct gtgtgaaatt    7440
```

| | |
|---|---|
| gttatccgct cacaattcca cacaacatac gagccggaag cataaagtgt aaagcctggg | 7500 |
| gtgcctaatg agtgagctaa ctcacattaa ttgcgttgcg ctcactgccc gctttccagt | 7560 |
| cgggaaacct gtcgtgccag ctgcattaat gaatcggcca acgcgcgggg agaggcggtt | 7620 |
| tgcgtattgg gcgctcttcc gcttcctcgc tcactgactc gctgcgctcg gtcgttcggc | 7680 |
| tgcggcgagc ggtatcagct cactcaaagg cggtaatacg gttatccaca gaatcagggg | 7740 |
| ataacgcagg aaagaacatg tgagcaaaag gccagcaaaa ggccaggaac cgtaaaaagg | 7800 |
| ccgcgttgct ggcgtttttc cataggctcc gcccccctga cgagcatcac aaaaatcgac | 7860 |
| gctcaagtca gaggtggcga aacccgacag gactataaag ataccaggcg tttccccctg | 7920 |
| gaagctccct cgtgcgctct cctgttccga ccctgccgct taccggatac ctgtccgcct | 7980 |
| ttctcccttc gggaagcgtg cgctttctc atagctcacg ctgtaggtat ctcagttcgg | 8040 |
| tgtaggtcgt tcgctccaag ctgggctgtg tgcacgaacc ccccgttcag cccgaccgct | 8100 |
| gcgccttatc cggtaactat cgtcttgagt ccaacccggt aagacacgac ttatcgccac | 8160 |
| tggcagcagc cactggtaac aggattagca gagcgaggta tgtaggcggt gctacagagt | 8220 |
| tcttgaagtg gtggcctaac tacggctaca ctagaaggac agtatttggt atctgcgctc | 8280 |
| tgctgaagcc agttaccttc ggaaaaagag ttggtagctc ttgatccggc aaacaaacca | 8340 |
| ccgctggtag cggtggtttt tttgtttgca agcagcagat tacgcgcaga aaaaaggat | 8400 |
| ctcaagaaga tcctttgatc ttttctacgg gtctgacgc tcagtggaac gaaaactcac | 8460 |
| gttaagggat tttggtcatg agattatcaa aaaggatctt cacctagatc cttttaaatt | 8520 |
| aaaaatgaag ttttaaatca atctaaagta tatatgagta aacttggtct ga | 8572 |

<210> SEQ ID NO 37
<211> LENGTH: 708
<212> TYPE: DNA
<213> ORGANISM: Unknown
<220> FEATURE:
<223> OTHER INFORMATION: BSC1-5 ORF

<400> SEQUENCE: 37

| | |
|---|---|
| atgaaaatgt caaataaagc caagttcgca ggtgctctgg cactgatggc ttccggcctg | 60 |
| atcctgtcca gcgccgccat ggccgcctcc ggtggtggca gcggcggcac cagctgcagc | 120 |
| gtttcccgcg aatccgcaac tggctcggtt ttctacgtac cacgcggcgg cagcggcacc | 180 |
| tacaatatcc tcggttgggg taacggcacc ggcggtggtt ctacgaccta ccgtggcctt | 240 |
| ctgacctcgg ttgcagagcg ttgcatcctg gttgctgcag caaccaccgc taactccggc | 300 |
| agtggccgtg aggtagagaa ctccgtcaac caggccaaga gccgttatcg caacattgtt | 360 |
| ggcgccagcc cgaaagtctg tacctctggc cactcccagg gtggcggcgg ttccttcaat | 420 |
| gctgcaaacc gtctgggcgc tgactgtgtg atcgccgtgc agccagacac cgtgtacacc | 480 |
| accagcattg accgtccggt tgccagcaac gtcgacgttg tctgtatctt cagccgcagt | 540 |
| gacaccctgg ccccggcgtc tccgtttaac tcacgtaact gccgccaa ctccactcgc | 600 |
| tactctgaag agtccaccctc cggtggtcac ttcgctccga cttccggtga cggtggtgag | 660 |
| cctggccgtg tcatgcgtga ctatgcgcag cgttggttgg tcaattga | 708 |

<210> SEQ ID NO 38
<211> LENGTH: 235
<212> TYPE: PRT
<213> ORGANISM: Unknown
<220> FEATURE:
<223> OTHER INFORMATION: BSC1-5 polypeptide

<400> SEQUENCE: 38

```
Met Lys Met Ser Asn Lys Ala Lys Phe Ala Gly Ala Leu Ala Leu Met
1               5                   10                  15

Ala Ser Gly Leu Ile Leu Ser Ser Ala Ala Met Ala Ala Ser Gly Gly
            20                  25                  30

Gly Ser Gly Gly Thr Ser Cys Ser Val Ser Arg Glu Ser Ala Thr Gly
        35                  40                  45

Ser Val Phe Tyr Val Pro Arg Gly Gly Ser Gly Thr Tyr Asn Ile Leu
    50                  55                  60

Gly Trp Gly Asn Gly Thr Gly Gly Gly Ser Thr Thr Tyr Arg Gly Leu
65                  70                  75                  80

Leu Thr Ser Val Ala Glu Arg Cys Ile Leu Val Ala Ala Ala Thr Thr
                85                  90                  95

Ala Asn Ser Gly Ser Gly Arg Glu Val Glu Asn Ser Val Asn Gln Ala
            100                 105                 110

Lys Ser Arg Tyr Arg Asn Ile Val Gly Ala Ser Pro Lys Val Cys Thr
            115                 120                 125

Ser Gly His Ser Gln Gly Gly Gly Ser Phe Asn Ala Ala Asn Arg
        130                 135                 140

Leu Gly Ala Asp Cys Val Ile Ala Val Gln Pro Asp Thr Val Tyr Thr
145                 150                 155                 160

Thr Ser Ile Asp Arg Pro Val Ala Ser Asn Val Asp Val Val Cys Ile
                165                 170                 175

Phe Ser Arg Ser Asp Thr Leu Ala Pro Ala Ser Pro Phe Asn Ser Arg
            180                 185                 190

Asn Cys Arg Ala Asn Ser Thr Arg Tyr Ser Glu Glu Ser Thr Ser Gly
            195                 200                 205

Gly His Phe Ala Pro Thr Ser Gly Asp Gly Gly Glu Pro Gly Arg Val
        210                 215                 220

Met Arg Asp Tyr Ala Gln Arg Trp Leu Val Asn
225                 230                 235
```

<210> SEQ ID NO 39
<211> LENGTH: 1476
<212> TYPE: DNA
<213> ORGANISM: Unknown
<220> FEATURE:
<223> OTHER INFORMATION: BSC-13 ORF

<400> SEQUENCE: 39

```
atggatgcac tgcattatca gtcggcccac acgcttcttg aacagctgga cacaggcgcg    60
ctgaccagcg aagaactgac tcgcgccctg ctcgagcgga tccgggtggt gaacccgcaa   120
gtcaacgcgg ttgtcaccct ggacgaacag caggcactgg ccgatgcccg ccaggccgac   180
gcttcccgtg ctgcaggaca agtaaaaggc ccgttgcacg gcttacccct gaccatcaaa   240
gacacttggg aagtcgccgg catgacctgc accgccgggg catcgcagct acggaaccat   300
aaaccggagc gccacgctga tgtcatcgag cgactggaaa gcgccggagc cataatcctg   360
ggcaagacca acgtgccgat ctatgcgacc gacctgcaga gttacaacaa actcttcggg   420
gtcaccaaca atccccacaa tccggctcat accccggtg gctcctcggg tggcgctgca   480
gccgcactgg ccgcgggcat gacagcgctg gaagtaggca gcgatctggc cggttccatt   540
cggacccctg cccatttctg tggcgtgttc ggccacaaac cgtcccgctc gctggtgtct   600
tttcgcggcc atatccccgg accacccggc acccagtccc agcccgacct ggccgaaggc   660
```

```
ggcccccatgg cccgcaacgc ccgggatctt gaactgctgc tcaaggtgat tgccggcccc    720
cgagccgacc aggagcgcag ttgggccctc aagcttgcgc ctgcaacggt aaacagcctg    780
gaccaggcca ggattgggtt atggctggaa gatccgctat gtccggtgga accggaactg    840
acagaggcct accgtaacct gggtatcgcc cttgccgacc gcggcgccct ggtaaccgaa    900
gcccggcacc ctctgctgac tctggagcac atcctgccgg cgtatttcaa tttgctgggc    960
agcctgctca gcacctcgct caagccgtcc cagcgtcgac agatgaaatg gattgctcgg   1020
ctggagccgt ggctcaagtt ccttggcccc gccacagcct gcatcggcga atacggccgg   1080
ggcgtgaacc agccggttca ccaatggatg gcgtggagtg aaatgcgcga gaaaatgcgc   1140
gcccagatcg aatctctgtt cgaggaagtg gatgtcctgc tgacgccggt tacaccgacc   1200
acggccatac cccatgacca ttcgaacccg gtgttcaaac ggcgcattac cgtggcgggc   1260
aaaccgaggg cctacctgga ccagttctgc tggattgccc tggccactct gctcggcctg   1320
ccagctacct cggtgcccct tggacgggca aaaaacgggc tgcccttttaa cgtacaggtg   1380 atcggcgcac cggggatgga tctgacgacg attggtttcg cagggctgct tgaagaggcg   1440
ggactggcgg gatttgtgaa acccgagggg tattga                             1476
```

<210> SEQ ID NO 40
<211> LENGTH: 491
<212> TYPE: PRT
<213> ORGANISM: Unknown
<220> FEATURE:
<223> OTHER INFORMATION: BSC-13 polypeptide

<400> SEQUENCE: 40

```
Met Asp Ala Leu His Tyr Gln Ser Ala His Thr Leu Leu Glu Gln Leu
1               5                   10                  15

Asp Thr Gly Ala Leu Thr Ser Glu Glu Leu Thr Arg Ala Leu Leu Glu
            20                  25                  30

Arg Ile Arg Val Val Asn Pro Gln Val Asn Ala Val Val Thr Leu Asp
        35                  40                  45

Glu Gln Gln Ala Leu Ala Asp Ala Arg Gln Ala Asp Ala Ser Arg Ala
    50                  55                  60

Ala Gly Gln Val Lys Gly Pro Leu His Gly Leu Pro Leu Thr Ile Lys
65                  70                  75                  80

Asp Thr Trp Glu Val Ala Gly Met Thr Cys Thr Ala Gly Ala Ser Gln
                85                  90                  95

Leu Arg Asn His Lys Pro Glu Arg His Ala Asp Val Ile Glu Arg Leu
            100                 105                 110

Glu Ser Ala Gly Ala Ile Ile Leu Gly Lys Thr Asn Val Pro Ile Tyr
        115                 120                 125

Ala Thr Asp Leu Gln Ser Tyr Asn Lys Leu Phe Gly Val Thr Asn Asn
    130                 135                 140

Pro His Asn Pro Ala His Thr Pro Gly Gly Ser Ser Gly Gly Ala Ala
145                 150                 155                 160

Ala Ala Leu Ala Ala Gly Met Thr Ala Leu Glu Val Gly Ser Asp Leu
                165                 170                 175

Ala Gly Ser Ile Arg Thr Pro Ala His Phe Cys Gly Val Phe Gly His
            180                 185                 190

Lys Pro Ser Arg Ser Leu Val Ser Phe Arg Gly His Ile Pro Gly Pro
        195                 200                 205

Pro Gly Thr Gln Ser Gln Pro Asp Leu Ala Glu Gly Gly Pro Met Ala
```

Arg Asn Ala Arg Asp Leu Glu Leu Leu Leu Lys Val Ile Ala Gly Pro
225                 230                 235                 240

Arg Ala Asp Gln Glu Arg Ser Trp Ala Leu Lys Leu Ala Pro Ala Thr
            245                 250                 255

Val Asn Ser Leu Asp Gln Ala Arg Ile Gly Leu Trp Leu Glu Asp Pro
        260                 265                 270

Leu Cys Pro Val Glu Pro Glu Leu Thr Glu Ala Tyr Arg Asn Leu Gly
            275                 280                 285

Ile Ala Leu Ala Asp Arg Gly Ala Leu Val Thr Glu Ala Arg His Pro
        290                 295                 300

Leu Leu Thr Leu Glu His Ile Leu Pro Ala Tyr Phe Asn Leu Leu Gly
305                 310                 315                 320

Ser Leu Leu Ser Thr Ser Leu Lys Pro Ser Gln Arg Gln Met Lys
            325                 330                 335

Trp Ile Ala Arg Leu Glu Pro Trp Leu Lys Phe Leu Gly Pro Ala Thr
            340                 345                 350

Ala Cys Ile Gly Glu Tyr Gly Arg Gly Val Asn Gln Pro Val His Gln
            355                 360                 365

Trp Met Ala Trp Ser Glu Met Arg Glu Lys Met Arg Ala Gln Ile Glu
370                 375                 380

Ser Leu Phe Glu Glu Val Asp Val Leu Leu Thr Pro Val Thr Pro Thr
385                 390                 395                 400

Thr Ala Ile Pro His Asp His Ser Asn Pro Val Phe Lys Arg Arg Ile
            405                 410                 415

Thr Val Ala Gly Lys Pro Arg Ala Tyr Leu Asp Gln Phe Cys Trp Ile
            420                 425                 430

Ala Leu Ala Thr Leu Leu Gly Leu Pro Ala Thr Ser Val Pro Leu Gly
            435                 440                 445

Arg Ala Lys Asn Gly Leu Pro Phe Asn Val Gln Val Ile Gly Ala Pro
        450                 455                 460

Gly Met Asp Leu Thr Thr Ile Gly Phe Ala Gly Leu Leu Glu Glu Ala
465                 470                 475                 480

Gly Leu Ala Gly Phe Val Lys Pro Glu Gly Tyr
            485                 490

<210> SEQ ID NO 41
<211> LENGTH: 978
<212> TYPE: DNA
<213> ORGANISM: Candida antarctica (N-terminally truncated) Lipase B
      gene

<400> SEQUENCE: 41
atggccactc ctttggtgaa gcgtctacct tccggttcgg accctgcctt ttcgcagccc     60
aagtcggtgc tcgatgcggg tctgacctgc agggtgcttc gccatcctc ggtctccaaa    120 cccatccttc tcgtccccgg aaccggcacc acaggtccac agtcgttcga ctcgaactgg    180 atcccctct caacgcagtt gggttacaca ccctgctgga tctcaccccc gccgttcatg     240
ctcaacgaca cccaggtcaa cacggagtac atggtcaacg ccatcaccgc gctctacgct    300
ggttcgggca caacaagct tcccgtgctt acctggtccc agggtggtct ggttgcacag    360
tggggtctga ccttcttccc cagtatcagg tccaaggtcg atcgacttat ggcctttgcg    420
cccgactaca agggcaccgt cctgccggc cctctcgatg cactcgcggt tagtgcaccc    480
tccgtatggc agcaaaccac cggttcggca ctcaccaccg cactccgaaa cgcaggtggt    540

```
ctgacccaga tcgtgcccac caccaacctc tactcggcga ccgacgagat cgttcagcct      600
caggtgtcca actcgccact cgactcatcc tacctcttca acggaaagaa cgtccaggca      660
caggccgtgt gtgggccgct gttcgtcatc gaccatgcag gctcgctcac ctcgcagttc      720
tcctacgtcg tcggtcgatc cgccctgcgc tccaccacgg gccaggctcg tagtgcagac      780
tatggcatta cggactgcaa ccctcttccc gccaatgatc tgactcccga gcaaaggtc       840 gccgcggctg cgctcctggc gccggcagct gcagccatcg tggcgggtcc aaagcagaac      900
tgcgagcccg acctcatgcc ctacgcccgc ccctttgcag taggcaaaag gacctgctcc      960
ggcatcgtca ccccctga                                                    978
```

<210> SEQ ID NO 42
<211> LENGTH: 325
<212> TYPE: PRT
<213> ORGANISM: Candida antarctica Lipase B (N-terminally truncated)

<400> SEQUENCE: 42

```
Met Ala Thr Pro Leu Val Lys Arg Leu Pro Ser Gly Ser Asp Pro Ala
1               5                   10                  15

Phe Ser Gln Pro Lys Ser Val Leu Asp Ala Gly Leu Thr Cys Gln Gly
            20                  25                  30

Ala Ser Pro Ser Ser Val Ser Lys Pro Ile Leu Leu Val Pro Gly Thr
        35                  40                  45

Gly Thr Thr Gly Pro Gln Ser Phe Asp Ser Asn Trp Ile Pro Leu Ser
    50                  55                  60

Thr Gln Leu Gly Tyr Thr Pro Cys Trp Ile Ser Pro Pro Pro Phe Met
65                  70                  75                  80

Leu Asn Asp Thr Gln Val Asn Thr Glu Tyr Met Val Asn Ala Ile Thr
                85                  90                  95

Ala Leu Tyr Ala Gly Ser Gly Asn Asn Lys Leu Pro Val Leu Thr Trp
            100                 105                 110

Ser Gln Gly Gly Leu Val Ala Gln Trp Gly Leu Thr Phe Phe Pro Ser
        115                 120                 125

Ile Arg Ser Lys Val Asp Arg Leu Met Ala Phe Ala Pro Asp Tyr Lys
    130                 135                 140

Gly Thr Val Leu Ala Gly Pro Leu Asp Ala Leu Ala Val Ser Ala Pro
145                 150                 155                 160

Ser Val Trp Gln Gln Thr Thr Gly Ser Ala Leu Thr Thr Ala Leu Arg
                165                 170                 175

Asn Ala Gly Gly Leu Thr Gln Ile Val Pro Thr Thr Asn Leu Tyr Ser
            180                 185                 190

Ala Thr Asp Glu Ile Val Gln Pro Gln Val Ser Asn Ser Pro Leu Asp
        195                 200                 205

Ser Ser Tyr Leu Phe Asn Gly Lys Asn Val Gln Ala Gln Ala Val Cys
    210                 215                 220

Gly Pro Leu Phe Val Ile Asp His Ala Gly Ser Leu Thr Ser Gln Phe
225                 230                 235                 240

Ser Tyr Val Val Gly Arg Ser Ala Leu Arg Ser Thr Gly Gln Ala
                245                 250                 255

Arg Ser Ala Asp Tyr Gly Ile Thr Asp Cys Asn Pro Leu Pro Ala Asn
            260                 265                 270

Asp Leu Thr Pro Glu Gln Lys Val Ala Ala Ala Leu Leu Ala Pro
        275                 280                 285
```

Ala Ala Ala Ala Ile Val Ala Gly Pro Lys Gln Asn Cys Glu Pro Asp
290                 295                 300

Leu Met Pro Tyr Ala Arg Pro Phe Ala Val Gly Lys Arg Thr Cys Ser
305                 310                 315                 320

Gly Ile Val Thr Pro
              325

<210> SEQ ID NO 43
<211> LENGTH: 1112
<212> TYPE: DNA
<213> ORGANISM: Cuphea carthagenensis Cc1FatB1 acyl-ACP N-terminally
      truncated thioesterase gene

<400> SEQUENCE: 43
atggcgaacg gtagcgctgt ctctctgaag agcggctcct tgaatacgca agaggacact      60
tcttcttccc caccgccacg cgcgttcatc aaccaattac ccgactggtc catgttattg     120
acggcgatta ccactgtctt tgttgccgca gagaaacagt ggactatgtt agaccgcaag     180
agcaagcgct ccgatatgtt agtggattct tttggcatgg aacgcattgt gcaggatggc     240
ttagtgtttc gtcaatcttt tagcattcgt tcttatgaaa tcggtgcaga tcgtcgtgca     300
tccattgaaa ccttaatgaa ccatctgcag gaaactagct gaatcattg caaatccatt     360 cgcttgttga tgagggtttt ggtcgcacc cccgagatgt gcaaacgtga cttgatctgg     420
gtggttaccc gcatgcacat catggtcaac cgctacccta cctggggtga taccgttgag     480
attaacactt gggtttccca agcggcaag aatggtatgg tcgtgattg gctgatttcc     540 gactgtaata ccggcgaaat cctgatccgc gcgacgtctg catgggcgat gatgaaccaa     600
aagacccgtc gtctgtctaa actgccttac gaagtcagcc aagagattgc tccgcacttc     660
gtcgacagcc ctcccgtgat cgaggacgg gaccgtaagt acacaagtt cgatgtgaaa     720 accggcgaca gcatccgtaa aggtttgact ccgcgttgga atgacttaga tgttaatcag     780
cacgttaaca acgttaagta tatcggctgg atcttagaga gcatgccgac cgaggtcttg     840
gaaactcatg aactgtgttt cttaactctg gagtatcgtc gcgagtgcgg tcgcgatagc     900
gtgctggaat ctgtgaccgc gatggatcct tctaatgaag gtggtcgctc ccactaccag     960
catttactgc gcttggagga cggtactgac atcgttaagg gccgcactga gtggcgtcca    1020
aagaatgccc ggaatattgg tgccattagt accggtaaaa ccagtaatgg taatcccgcc    1080
agttaataat gatcagatcc ggagtttgta ga                                  1112

<210> SEQ ID NO 44
<211> LENGTH: 361
<212> TYPE: PRT
<213> ORGANISM: Cuphea carthagenensis Cc1FatB1 N-terminally truncated
      Cc1FatB1 thioesterase

<400> SEQUENCE: 44

Met Ala Asn Gly Ser Ala Val Ser Leu Lys Ser Gly Ser Leu Asn Thr
1               5                   10                  15

Gln Glu Asp Thr Ser Ser Ser Pro Pro Pro Arg Ala Phe Ile Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
    50                  55                  60

Asp Met Leu Val Asp Ser Phe Gly Met Glu Arg Ile Val Gln Asp Gly
65                  70                  75                  80

```
Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
    130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
    210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Val Lys Tyr Ile Gly Trp Ile Leu
            260                 265                 270

Glu Ser Met Pro Thr Glu Val Leu Glu Thr His Glu Leu Cys Phe Leu
        275                 280                 285

Thr Leu Glu Tyr Arg Arg Glu Cys Gly Arg Asp Ser Val Leu Glu Ser
    290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
        355                 360

<210> SEQ ID NO 45
<211> LENGTH: 220
<212> TYPE: DNA
<213> ORGANISM: Artificial Sequence
<220> FEATURE:
<223> OTHER INFORMATION: TrcE promoter

<400> SEQUENCE: 45
tgttgacaat taatcatccg gctcgtataa tgtgtggaat tgtgagcgga taacaatttc      60
acacaggaaa cagcgccgct gagaaaaagc gaagcggcac tgctctttaa caatttatca    120
gacaatctgt gtgggcactc gaccggaatt atcgattaac tttattatta aaaattaaag    180
aggtatatat taatgtatcg attaaataag gaggaataaa                          220

<210> SEQ ID NO 46
<211> LENGTH: 843
<212> TYPE: DNA
<213> ORGANISM: Unknown
<220> FEATURE:
```

<223> OTHER INFORMATION: P500114 gene

<400> SEQUENCE: 46

```
atgattgcga gaaccggcag cccggattcc gtgagccagg tgtgggacat ccagataccg      60
gctaccaatc cgacgcgcaa cctggcggcg agggtataca ggcccgtgga gattgaggcg     120
gattgtccat tgcctgttgt gctgttcctg cacggcggtg gctttatctg cggagacctg     180
gatacccacg atgtgatgat cgtgccctg gccaaccgca gcggcgccct gatggtgtca     240
ttggcgtacc gccttgcgcc tgaggcgcct ttcccggccg cgctggacga tgtgagcgtg     300
gccttgcagt ggctgtcgag caatgcgtac accctgggcg gtgacccgcg cgcctgctg     360
gtaggggcg acagcgcggg cggtaacctg acggctgcag cgtgcataca agcgcgagat     420
cacggcgggc gcgcgcattgc cggccaactg ctgttctacg ccaacgtgga tggcaatggc     480
gggacggcgt cctgggaagc attggccgat cgctacttcc ccactcgcca ggcgatggag     540
ctgacgttgc aatgctacgt gccgggtgcc cccgaacaac gtcgtaatcc gttggtgtca     600
ccgctgcgcg ccaccttgaa tgatctcccg ccggcattgg tgattaccgc ggggctcgat     660
ccgctcaagg atgaagggca ggcctatgca gagaagttgc gaaaggcggg tgtggcggcg     720
cagtaccagc tgtacgaggg ggtggagcat ggcttcatcg agttttttcaa ggaagcacgg     780
aaccggccca tgggcgagca ggcattggac gaagcggcgg tgtttatcag gcgggtaggg     840
tag                                                                     843
```

<210> SEQ ID NO 47
<211> LENGTH: 280
<212> TYPE: PRT
<213> ORGANISM: Unknown
<220> FEATURE:
<223> OTHER INFORMATION: P500114 protein

<400> SEQUENCE: 47

```
Met Ile Ala Arg Thr Gly Ser Pro Asp Ser Val Ser Gln Val Trp Asp
1               5                   10                  15

Ile Gln Ile Pro Ala Thr Asn Pro Thr Arg Asn Leu Ala Ala Arg Val
            20                  25                  30

Tyr Arg Pro Val Glu Ile Glu Ala Asp Cys Pro Leu Pro Val Val Leu
        35                  40                  45

Phe Leu His Gly Gly Gly Phe Ile Cys Gly Asp Leu Asp Thr His Asp
    50                  55                  60

Val Met Ile Arg Ala Leu Ala Asn Arg Ser Gly Ala Leu Met Val Ser
65                  70                  75                  80

Leu Ala Tyr Arg Leu Ala Pro Glu Ala Pro Phe Pro Ala Ala Leu Asp
                85                  90                  95

Asp Val Ser Val Ala Leu Gln Trp Leu Ser Ser Asn Ala Tyr Thr Leu
            100                 105                 110

Gly Gly Asp Pro Arg Arg Leu Leu Val Gly Gly Asp Ser Ala Gly Gly
        115                 120                 125

Asn Leu Thr Ala Ala Ala Cys Ile Gln Ala Arg Asp His Gly Gly Pro
    130                 135                 140

Arg Ile Ala Gly Gln Leu Leu Phe Tyr Ala Asn Val Asp Gly Asn Gly
145                 150                 155                 160

Gly Thr Ala Ser Trp Glu Ala Leu Ala Asp Arg Tyr Phe Pro Thr Arg
                165                 170                 175

Gln Ala Met Glu Leu Thr Leu Gln Cys Tyr Val Pro Gly Ala Pro Glu
            180                 185                 190
```

```
Gln Arg Arg Asn Pro Leu Val Ser Pro Leu Arg Ala Thr Leu Asn Asp
        195                 200                 205

Leu Pro Pro Ala Leu Val Ile Thr Ala Gly Leu Asp Pro Leu Lys Asp
        210                 215                 220

Glu Gly Gln Ala Tyr Ala Glu Lys Leu Arg Lys Ala Gly Val Ala Ala
225                 230                 235                 240

Gln Tyr Gln Leu Tyr Glu Gly Val Glu His Gly Phe Met Gln Phe Phe
                245                 250                 255

Lys Glu Ala Arg Asn Arg Pro Met Gly Glu Gln Ala Leu Asp Glu Ala
            260                 265                 270

Ala Val Phe Ile Arg Arg Val Gly
        275                 280
```